US011413325B2

(12) United States Patent
He et al.

(10) Patent No.: US 11,413,325 B2
(45) Date of Patent: Aug. 16, 2022

(54) NEURONAL SURVIVAL AND AXONAL REGENERATION THROUGH INCREASING MITOCHONDRIAL MOTILITY

(71) Applicant: THE CHILDREN'S MEDICAL CENTER CORPORATION, Boston, MA (US)

(72) Inventors: Zhigang He, Wellesley, MA (US); Thomas L. Schwarz, Newton, MA (US); Cartoni Romain, Boston, MA (US)

(73) Assignee: THE CHILDREN'S MEDICAL CENTER, Boston, MA (US)

(*) Notice: Subject to any disclaimer, the term of this patent is extended or adjusted under 35 U.S.C. 154(b) by 0 days.

(21) Appl. No.: 16/467,750

(22) PCT Filed: Dec. 7, 2017

(86) PCT No.: PCT/US2017/065113
§ 371 (c)(1),
(2) Date: Jun. 7, 2019

(87) PCT Pub. No.: WO2018/106918
PCT Pub. Date: Jun. 14, 2018

(65) Prior Publication Data
US 2020/0061154 A1 Feb. 27, 2020

Related U.S. Application Data

(60) Provisional application No. 62/431,206, filed on Dec. 7, 2016.

(51) Int. Cl.
| *A61K 38/17* | (2006.01) |
| *A61P 25/00* | (2006.01) |
| *G01N 33/50* | (2006.01) |
| *G01N 33/68* | (2006.01) |
| *A61K 45/06* | (2006.01) |

(52) U.S. Cl.
CPC .......... *A61K 38/1709* (2013.01); *A61K 45/06* (2013.01); *A61P 25/00* (2018.01); *G01N 33/5029* (2013.01); *G01N 33/5058* (2013.01); *G01N 33/6896* (2013.01)

(58) Field of Classification Search
CPC .. A61K 38/1709; A61K 45/06; A61K 31/665; A61K 31/708; A61P 25/00; G01N 33/5029; G01N 33/5058; G01N 33/6896
See application file for complete search history.

(56) References Cited

U.S. PATENT DOCUMENTS

2007/0178535 A1  8/2007  Huang et al.

OTHER PUBLICATIONS

Barnhart EL, Current Opinion in Cell Biology, 38:90-99, (Year: 2016).*
Van Bergeijk et al., Nature, 518: 111-114, Feb. 2015 (Year: 2015).*
Cartoni et al., "The Mammalian-Specific Protein Armcx1 Regulates Mitochondrial Transport during Axon Regeneration", Neuron 92(6): 1294-1307 (2016).
Chang et al., "Mitochondrial trafficking and morphology in healthy and injured neurons", Prog Neurobiol 80(5): 241-268 (2006).
Lopez-Domenech et al., "The Eutherian Armcx genes regulate mitochondrial trafficking in neurons and interact with Miro and Trak2", Nat Common 3(814): 1-12 (2012).

* cited by examiner

*Primary Examiner* — Kimberly Ballard
*Assistant Examiner* — Stacey N MacFarlane
(74) *Attorney, Agent, or Firm* — Nixon Peabody LLP; David S. Resnick; Shayne Y. Huff

(57) ABSTRACT

Disclosed are compositions and methods for promoting survival of or axon regeneration in neurons by increasing mitochondrial motility in the neuron. Also disclosed are methods to treat neuronal injury and disease and disorders characterized by neuronal injury. Agents that increase Armcx1 activity, such as Armcx1 polypeptide or vectors comprising nucleic acid encoding Armcx1 polypeptide, are proposed for use in the methods. Pharmaceutical composition comprising the agents, and methods for identifying additional agents are also disclosed.

15 Claims, 29 Drawing Sheets
Specification includes a Sequence Listing.

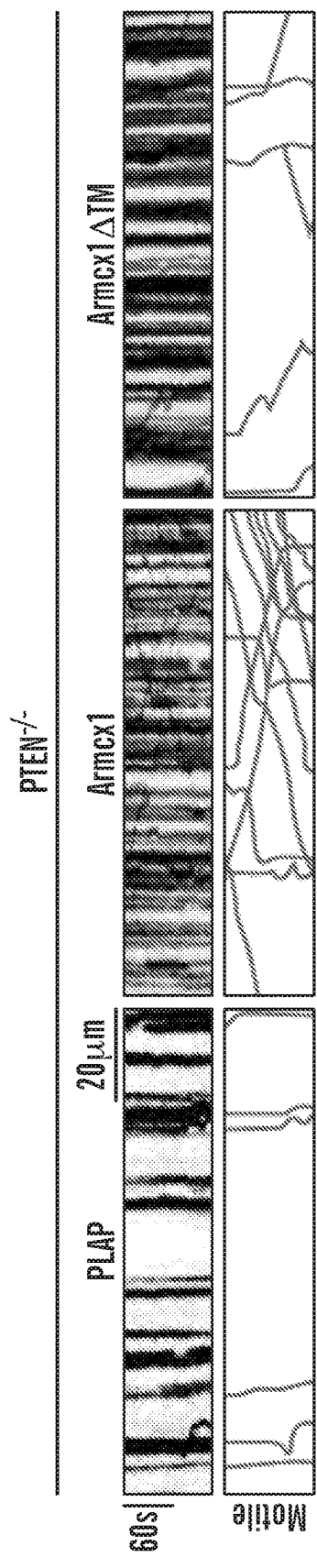
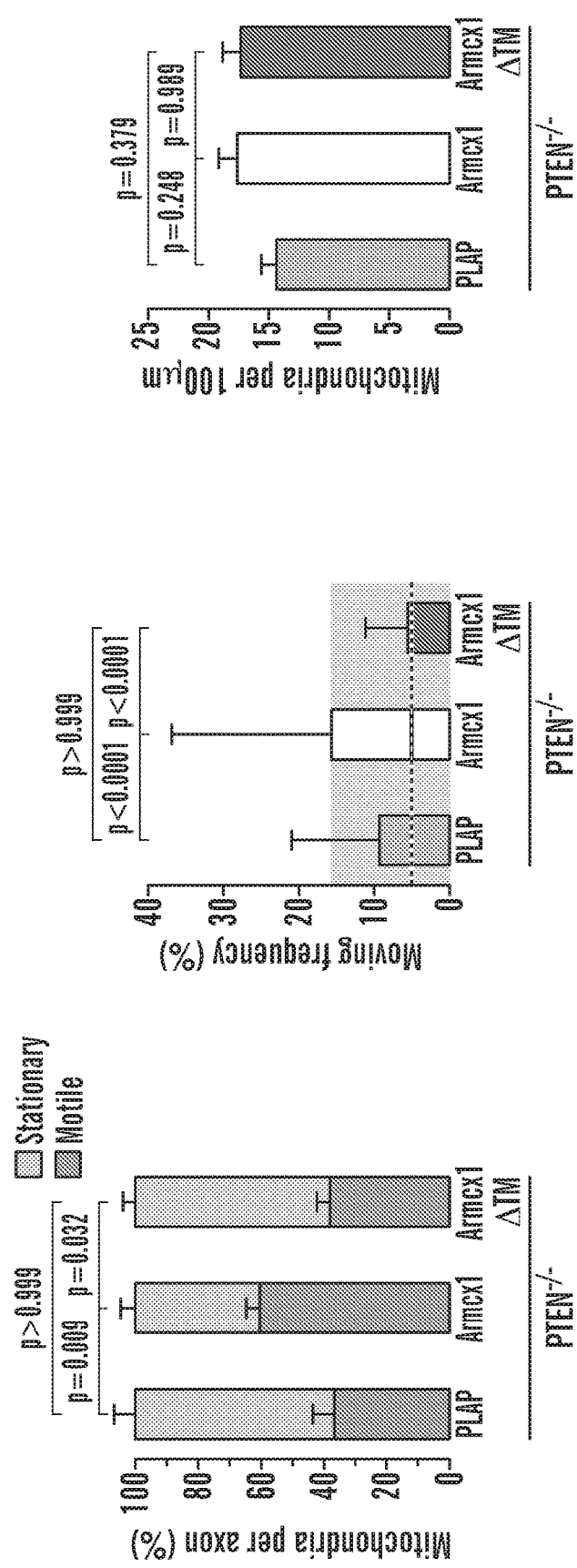
FIG. 2A
FIG. 2B
FIG. 2C
FIG. 2D

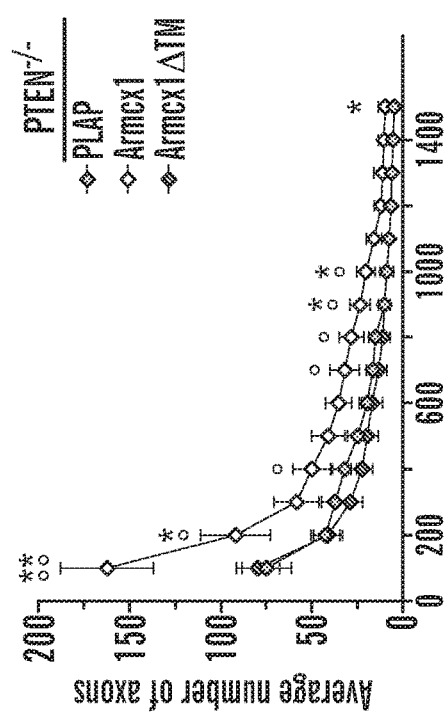
FIG. 2F
FIG. 2G
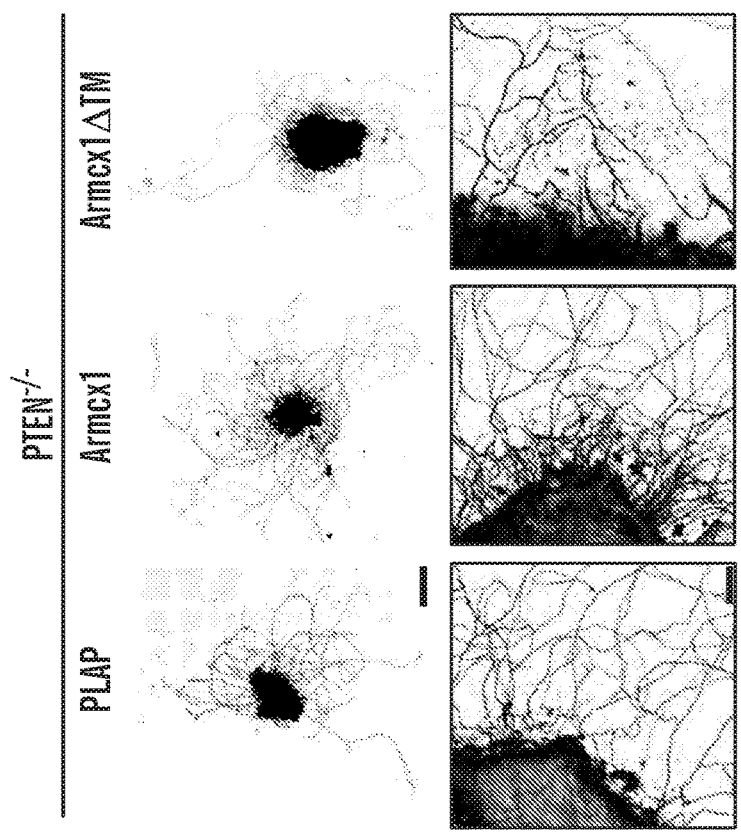
FIG. 2E

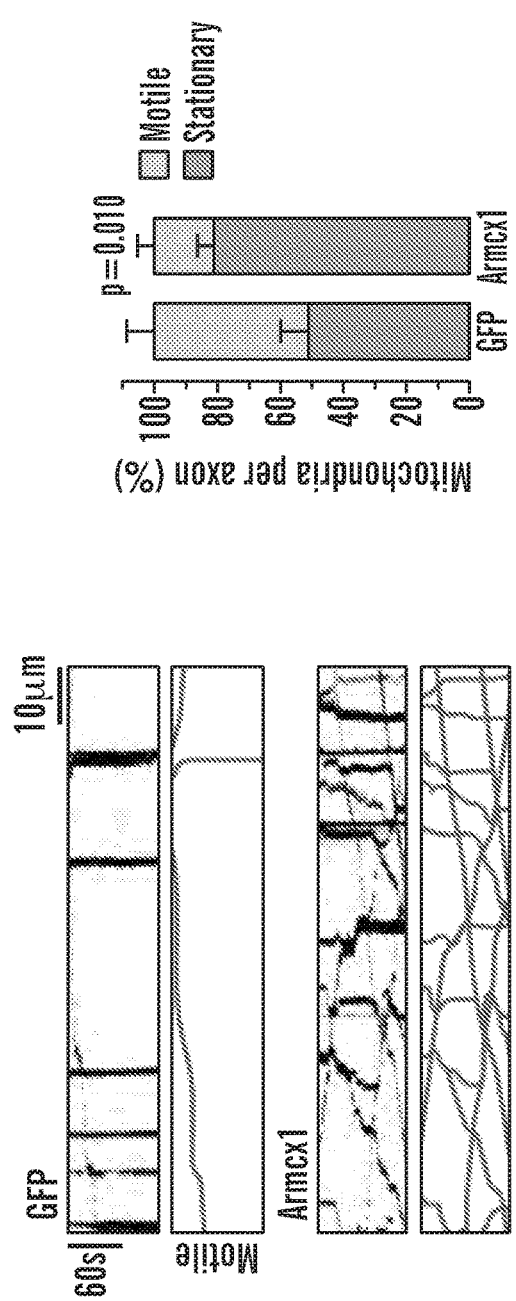
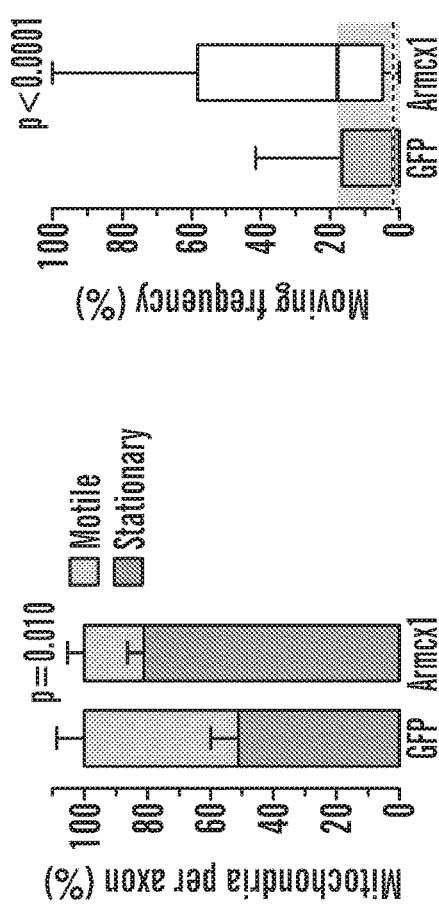
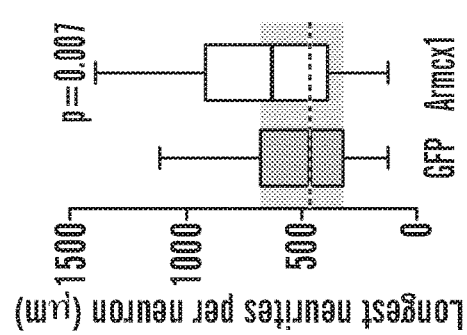
FIG. 3A
FIG. 3B
FIG. 3C
FIG. 3D
FIG. 3E

NEURONAL SURVIVAL AND AXONAL REGENERATION THROUGH INCREASING MITOCHONDRIAL MOTILITY

RELATED APPLICATIONS

This application is a 35 U.S.C. § 371 National Entry Application of International Application No. PCT/US2017/065113, filed Dec. 7, 2017, which designates the U.S. and claims the benefit under 35 U.S.C. § 119(e) of U.S. Provisional Application No. 62/431,206 filed Dec. 7, 2016 the contents of each of which are incorporated herein by reference in their entireties.

GOVERNMENTAL SUPPORT

This invention was made with government support under Grant No. R01EY021242, R01GM069808, P30 HD018655 and P30EY012196 awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Dec. 7, 2017, is named 701039-088421-PCT_SL.txt and is 4,721 bytes in size.

FIELD OF THE INVENTION

The present invention relates to field of neuronal survival and regeneration.

BACKGROUND

After axotomy, a battery of alterations, such as membrane breakdown, cytoskeleton disassembly and calcium influx, occurs in injured axonal stumps. However, it remains poorly understood how injured neurons cope with such stresses and decide their survival and regenerative responses (Abe and Cavalli, 2008; Bradke et al., 2012; Goldberg and Barres, 2000; He and Jin, 2016). In intact conditions, neuronal mitochondria are transported along the axon across considerable distances to meet local needs for ATP and calcium buffering. Whereas mitochondria remain uniformly distributed along axons in non-growing conditions, mitochondrial distribution is biased towards the active growth cone when the axon is growing, suggesting that mitochondrial transport is regulated to support axonal growth (Morris and Hollenbeck, 1993). Thus, it is conceivable that mitochondrial dynamics might be important for regulating axonal and neuronal injury responses.

In all species, axonal mitochondria move bi-directionally along microtubule tracks. Their movement can be continuous or interrupted by pauses (for review see (Schwarz, 2013)). Previous studies revealed that an evolutionarily conserved protein complex that includes the mitochondrial GTPase Miro (also called RhoT1/2) and the adaptor Milton (also called Trak1/2) is essential for regulating the transport of mitochondria. However, considering the complexity of mitochondrial dynamics and its extensive regulation by signaling pathways (Courchet et al., 2013; Pekkurnaz et al., 2014; 3 Wang et al., 2011), it is unknown what regulatory mechanisms might act in fine tuning mitochondrial transport during pathological conditions, such as after an injury. In injured axons of the peripheral nervous system (PNS), it has been shown that regenerating axons increase mitochondrial movement (Mar et al., 2014; Misgeld et al., 2007), but the mechanisms underlying this response remain unclear. In addition, as most injured axons in the adult CNS cannot regenerate spontaneously, the regulation of mitochondrial transport and its relevance to axon regeneration in these axons has not been formally investigated. Therefore, whether increasing mitochondrial movement could have an impact on neuronal survival and axon regeneration remains an open question.

SUMMARY

Aspects of the present invention relate to the discovery that expression of Armcx1 correlates with high axonal regeneration, modulates the transport of the axonal mitochondria and promotes neuronal survival and axonal regeneration. Described herein are compositions and methods to promote survival of neurons and/or axons regeneration of neurons. Provided herein are methods and compositions useful for neuronal injury or a disease or disorder causing neuronal injury or resulting from neuronal injury.

In one aspect provided herein is a method for promoting survival of, or axon regeneration in an injured mature central nervous system (CNS) neuron, the method comprising: contacting the neuron with an effective amount of an agent capable of increasing mitochondrial motility in the injured neuron, thereby promoting survival of, or axon regeneration in the injured neuron.

In some embodiments, the method of the foregoing aspect further comprises detecting the resultant promotion of the survival of, or axon regeneration in the injured neuron in the subject.

In some embodiments, the injured neuron results from traumatic injury, traumatic brain injury, optic nerve injury, acute spinal cord injury, stroke, restorative CNS surgery or CNS degeneration.

In some embodiments, the injured neuron is a sensory neuron.

In some embodiments, the injured neuron is in the spinal cord or the optic nerve.

In some embodiments, the agent is administered intravenously, intracortically, intracerebrally, intrathecally, intranasally, ocularly or locally at the injured neuron.

In some embodiments, the agent is Armcx1 polypeptide. In some embodiments, the Armcx1 polypeptide is recombinant. In some embodiments, the Armxc1 polypeptide comprises a carrier peptide or lipophilic molecular group and/or is encapsulated in a liposome or a nanoparticle.

In some embodiments, the agent is a vector comprising a nucleic acid sequence that encodes an Armcx1 polypeptide.

In some embodiments, the vector is a viral vector or non-viral vector. In some embodiments, the viral vector is selected from the group consisting of retrovirus, lentivirus, adenovirus, herpesvirus, poxvirus, alpha virus, vaccinia virus, and adeno-associated viruses. In some embodiments, the non-viral vector is selected from the group consisting of a nanoparticle, a cationic lipid, a cationic polymer, a metallic nanoparticle, a nanorod, a liposome, microbubbles, a cell penetrating peptide and a liposphere.

In some embodiments, the Armcx1 polypeptide is of human origin. In some embodiments, the Armcx1 polypeptide comprises the sequence of SEQ ID NO:1. In some embodiments the Armcx1 polypeptide has at least 95% amino acid sequence identity to SEQ ID NO:1 and retains at least 80% of the biological activity of human Armcx1 of SEQ ID NO:1.

In some embodiments, the detecting step is effected by an indirect assay of axon regeneration.

In some embodiments, the detecting step is effected by a direct assay of axon regeneration.

In some embodiments, the method of the foregoing aspect further comprises an antecedent step of determining that the neuron is injured, and has axotomy-induced stress.

In some embodiments, the method of the foregoing aspect further comprises contacting the injured neuron with a PTEN inhibitor, inhibitor of suppressor of cytokine signaling 3 (SOCS3), inosine, oncomodulin, BNDF, NGF, CNTF, or combinations thereof.

In some embodiments, the inhibitor of SOCS3 comprises a SOCS3 specific hpRNA or siRNA.

In some embodiments, the PTEN inhibitor is, (a) potassium bisperoxo(bipyridine)oxovanadate (V) (bpV(bipy)); (b) dipotassium bisperoxo(5-hydroxypyridine-2-carboxyl) oxovanadate (V) (bpV(HOpic)); (c) potassium bisperoxo(1, 10-phenanthroline)oxovanadate (V), (bpV(phen)); or (d) dipotassium bisperoxo(picolinato)oxovanadate (V), (bpV (pic)).

In some embodiments, the neuron is human.

In another aspect, technology herein relates to a method of treating a subject for neuronal injury, comprising: administering to the subject an agent that increases mitochondrial motility in injured neurons, wherein the administering results in contacting the injured neurons of the subject with the agent in an amount sufficient to promote survival of, or axon regeneration in the injured neurons, such that the subject is treated.

In some embodiments, the agent is administered intravenously, intracortically, intracerebrally, intrathecally, intranasally, ocularly or locally at the site of neuronal injury.

In some embodiments, the neuronal injury results from a traumatic injury, traumatic brain injury, optic nerve injury, acute spinal cord injury, stroke, restorative CNS surgery or CNS degeneration.

In some embodiments, the neuronal injury results from restorative CNS injury and wherein the agent is administered prior to, during or following restorative CNS surgery.

In some embodiments, the agent is Armcx1 polypeptide.

In some embodiments, the Armcx1 polypeptide is recombinant.

In some embodiments, the Armxc1 polypeptide comprises a carrier peptide or lipophilic molecular group and/or is encapsulated in a liposome or a nanoparticle.

In some embodiments, the agent is a vector comprising a nucleic acid sequence that encodes a Armcx1 polypeptide.

In some embodiments, the vector is a viral vector or non-viral vector. In some embodiments, the viral vector is selected from the group consisting of retrovirus, lentivirus, adenovirus, herpesvirus, poxvirus, alpha virus, vaccinia virus, and adeno-associated viruses. In some embodiments, the non-viral vector is selected from the group consisting of a nanoparticle, a cationic lipid, a cationic polymer, a metallic nanoparticle, a nanorod, a liposome, microbubbles, a cell penetrating peptide and a liposphere.

In some embodiments, the Armcx1 polypeptide is of human origin.

In some embodiments, the Armcx1 polypeptide comprises the sequence of SEQ ID NO:1.

In some embodiments, the Armcx1 polypeptide has at least 95% amino acid sequence identity to SEQ ID NO:1 and retains at least 80% of the biological activity of human Armcx1 of SEQ ID NO:1.

In another aspect, technology herein relates to a method of treating a subject for a disease or disorder characterized by neuronal death or diminished potential for axonal growth, comprising administering to the subject an agent that increases mitochondrial motility, in an amount sufficient to promote survival of, or axonal growth in neurons, such that the subject is treated.

In some embodiments, the disorder is selected from group comprising of glaucoma, stroke, head trauma, spinal injury, optic injury, ischemia, hypoxia, neurodegenerative disease, multiple sclerosis, infectious disease, cancer, and autoimmune disease.

In some embodiments, the agent is Armcx1 polypeptide or a vector comprising a nucleic acid sequence encoding an Armcx1 polypeptide.

In another aspect of the technology herein is a method for promoting survival of, or axon regeneration in an injured mature central nervous system neuron in a subject determined to have a neuronal injury, the method comprising, administering to the subject Armcx1 polypeptide or an analog thereof in an amount sufficient to promote survival of, or axon regeneration of the injured neuron.

In another aspect, technology herein relates to a device for promoting survival of, or axon regeneration in an injured mature central nervous system (CNS) neuron in situ, comprising a therapeutically effective amount of an agent that increases mitochondrial motility in the neuron, and wherein the device locally releases the agent into the CNS for promoting survival of, or axon regeneration in an injured mature central system (CNS) neuron.

In some embodiments, the device of the foregoing aspect comprises a CNS-implantable solid or semi-solid device selected from a biodegradable matrix, fiber, pump, stent, adsorbable gelatin osmotic pump or indwelling catheter.

In another aspect, provided herein is a pharmaceutical composition comprising an effective amount of Armcx1 polypeptide or a vector comprising a nucleic acid sequence encoding the Armcx1 polypeptide and a pharmaceutically acceptable carrier, for use in promoting survival of, or regeneration of axon in injured neurons.

In some embodiments, the Armcx1 polypeptide is of human origin.

In some embodiments, the Armcx1 polypeptide comprises the sequence of SEQ ID NO:1.

In some embodiments, the Armcx1 polypeptide has at least 95% amino acid sequence identity to SEQ ID NO:1 and retains at least 80% of the biological activity of human Armcx1 of SEQ ID NO:1.

In some embodiments, the Armcx1 polypeptide is fused to a carrier polypeptide.

In some embodiments, the vector is a viral or non-viral vector. In some embodiments, the viral vector is selected from the group consisting of retrovirus, lentivirus, adenovirus, herpesvirus, poxvirus, alpha virus, vaccinia virus, and adeno-associated viruses. In some embodiments, the non-viral vector is selected from the group consisting of a nanoparticle, a cationic lipid, a cationic polymer, a metallic nanoparticle, a nanorod, a liposome, microbubbles, a cell penetrating peptide and a liposphere.

In some embodiments, the Armcx1 polypeptide or the vector comprising a nucleic acid sequence encoding the Armcx1 polypeptide is formulated with a lipophilic molecular group and/or encapsulated in a liposome or a nanoparticle.

In some embodiments, the pharmaceutical compositions of the foregoing aspects, are formulated for administration to the brain, spinal cord, or optical nerve.

In some embodiments, the composition is formulated for administration via intracerebroventricular, intranasal, intracranial, intracelial, intracerebellar, or intrathecal administration route.

In some embodiments, the pharmaceutical composition is contained in a delivery device selected from the group consisting of a syringe, a blunt tip syringe, a catheter, an inhaler, a nebulizer, a nasal spray pump, a nasal irrigation pump or nasal lavage pump, and an implantable pump.

In another aspect, the technology herein relates to a pharmaceutical composition comprising an agent that increases mitochondrial motility in injured neuron and a pharmaceutically acceptable carrier, for use in promoting survival of, or regeneration of axon in injured neurons.

In some embodiments, the agent is Armcx1 polypeptide or a vector comprising a nucleic acid sequence encoding the Armcx1 polypeptide.

In another aspect, the technology herein relates to a method for identifying an agent effective in promoting survival of, or axon regeneration in neurons after injury, the method comprising: (a) contacting a neuron with a candidate agent; (b) determining expression level of Armcx1 in the neurons from step (a); and (c) identifying the candidate agent as effective if the expression level of Armcx1 is increased relative to a reference level upon the contact of the neuron with the candidate agent; or identifying the candidate agent as ineffective if the expression level of Armcx1 is not changed relative to a reference level upon the contact of the neuron with the candidate agent.

In some embodiments, the reference level is expression level of Armcx1 in neurons prior to contact with the candidate agent.

In some embodiments, the contacting is in vitro or in vivo.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

As used herein the term "consisting of" refers to compositions, methods, and respective components thereof as described herein, which are exclusive of any element not recited in that description of the embodiment.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

The term "in need thereof" when used in the context of a therapeutic or prophylactic treatment, means having a disease, being diagnosed with a disease, or being in need of preventing a disease, e.g., for one at risk of developing the disease. Thus, a subject in need thereof can be a subject in need of treating or preventing a disease.

As used herein, mitochondrial "motility" refers to mitochondrial movement within a cell. Motility of mitochondria is another aspect of mitochondrial dynamics beyond fusion and fission. This aspect is critically important in highly polarized cells, such as neurons. In some embodiments, increase in mitochondrial motility refers to the fraction of time mitochondria is in motion rather than paused. In some embodiments, increase in mitochondrial motility refers to increase in the motile mitochondrial pool.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically acceptable carrier" means a pharmaceutically-acceptable material, composition or vehicle, such as a liquid or solid filler, diluent, excipient, manufacturing aid or solvent encapsulating material necessary or used in formulating an active ingredient or agent for delivery to a subject. Each carrier must be "acceptable" in the sense of being compatible with the other ingredients of the formulation and not injurious to the patient.

In certain embodiments, Armcx1 polypeptide or vector comprising a nucleic acid sequence encoding an Armcx1 polypeptide or compositions provided herein can be formulated in liposomes to promote delivery across membranes. As used herein, the term "liposome" refers to a vesicular structure having lipid-containing membranes enclosing an aqueous interior. In cell biology, a vesicular structure is a hollow, lamellar, spherical structure, and provides a small and enclosed compartment, separated from the cytosol by at least one lipid bilayer. Liposomes can have one or more lipid membranes. Oligolamellar large vesicles and multilamellar vesicles have multiple, usually concentric, membrane layers and are typically larger than 100 nm. Liposomes with several nonconcentric membranes, i.e., several smaller vesicles contained within a larger vesicle, are termed multivesicular vesicles.

Liposomes can further comprise one or more additional lipids and/or other components such as sterols, e.g., cholesterol. Additional lipids can be included in the liposome compositions for a variety of purposes, such as to prevent lipid oxidation, to stabilize the bilayer, to reduce aggregation during formation or to attach ligands onto the liposome surface. Any of a number of additional lipids and/or other components can be present, including amphipathic, neutral, cationic, anionic lipids, and programmable fusion lipids. Such lipids and/or components can be used alone or in combination. One or more components of the liposome can comprise a ligand, e.g., a targeting ligand.

Liposome compositions can be prepared by a variety of methods that are known in the art. See e.g., patents cited as reference, (25, 26, 27, 28, 29, 30). Niosomes are non-phospholipid based synthetic vesicles that have properties and function like liposomes.

As used herein, the term "nanoparticle" refers to a particle having a size between 1 and 1000 nm which can be manufactured from artificial or natural macromolecular substances. To such nanoparticles can be bound drugs or other biologically active materials by covalent, ionic or adsorptive linkage, or the latter can be incorporated into the material of the nanoparticles. Nanoparticles may or may not exhibit size-related properties that differ significantly from those observed in fine particles or bulk materials. Nanoparticles provide improved bioavailability by enhancing aqueous solubility, increasing resistance time in the body (increasing half-life for clearance/increasing specificity for its cognate receptors and targeting drug to specific location in the body (its site of action). This results in concomitant reduction in quantity of the drug required and dosage toxicity, enabling the safe delivery of toxic therapeutic drugs and protection of non-target tissues and cells from severe side effects. Non-limiting examples of nanoparticles include solid lipid nanoparticles (comprise lipids that are in solid phase at room temperature and surfactants for emulsification, the mean diameters of which range from 50 nm to 1000 nm for colloid drug delivery applications), liposomes, nanoemulsions (oil-in-water emulsions done on a nano-scale), albumin nanoparticles, and polymeric nanoparticles.

Nanoparticles can be surface coated to modulate their stability, solubility, and targeting. A coating that is multivalent or polymeric confers high stability (34). A non-limiting example includes coating with hydrophilic polymer such as polyethylene glycol or polysorbate-80.

As used herein the term "lipophilic molecular group" refers to a lipid moiety, such as a fatty acid, glyceride or phospholipid which when coupled to a therapeutic molecule to be a targeted to the brain, increases its lipophilicity and hence movement across blood brain barrier. The lipophilic molecular group can be attached to the therapeutic molecule through an ester bond. As it relates to the present disclosure a lipophilic molecular group can enable uptake of the agents or compositions herein into the mitochondria of the neurons.

As used herein the term "carrier polypeptide" refers to a peptide which exhibits substantially no bioactivity. In some embodiments, the carrier peptide is a mitochondria targeting peptide and which is capable of targeting the agent to the mitochondria of the neuron. Examples of mitochondria target peptide are known in the art. See e.g., Mitochondrion. 2013 November; 13(6):610-4., Protein Eng. 1990 October; 4(1):33-7., the contents of which are incorporated herein by reference in its entirety). In some embodiments, the carrier peptide capable of passing the blood-brain barrier. The carrier peptide can be an endogenous peptide whose receptor is present on the cerebral capillary endothelial cell, such as insulin, insulin-like growth factor (IGF), leptin and transferrin or fragments thereof (see, e.g., reference 35). The carrier peptide can be, for example, a short cell penetrating peptide of less than 30 amino acids that are amphipathic in nature and are able to interact with lipidic membranes. Non-limiting examples of carrier peptides include SynB3, TAT (HIV-1 trans-activating transcriptor).

As used herein, the term "in combination" refers to the use of more than one prophylactic and/or therapeutic agent simultaneously or sequentially and in a manner such that their respective effects are additive or synergistic.

The term "effective amount" can be used interchangbly with "therapeutically effective amount" as used herein, refers to an amount sufficient to affect a beneficial or desired clinical result upon treatment. Specifically, the term "effective amount" means an amount of an agent e.g., Armcx1 polypeptide, sufficient to measurably increase at least one of; mitochondrial motility in injured neurons, ii. survival of injured neurons, or iii) axon regeneration in injured neurons by at least 3 fold, at least 2.5 fold, at least 2 fold, at least 1.5 fold upon contacting with injured neurons, ex vivo or in vivo with effective amount relative to absence of contacting. The increase in at least one of the desired biological activity can result in a measurable effect in terms of neuronal repair in a treated subject against for e.g., neurodegenerative disease, brain trauma, stroke. The effective amounts may vary, as recognized by those skilled in the art, depending on the number of neurons to be contacted, the duration of contact, the specific underlying disease resulting in neuronal injury, intensity of prior therapy such as chemotherapy or radiotherapy. The effective amount of an active therapeutic agent used to practice the present disclosure for the treatment of a CNS disease or neuronal injury varies depending upon the manner of administration, the age, body weight, and general health of the subject. Ultimately, the attending clinician will decide the appropriate amount and dosage regimen. Such amount is referred to as an "effective" amount.

An effective amount can therefore result in a clinical outcome of at least one selected from; increased survival of injured neurons or increased axon regeneration in injured neurons and cause treatment, reverse, alleviate, ameliorate, inhibit, slow down or stop the progression or severity of the disease characterized by, resulting in, or due to neuronal injury.

By "promoting regeneration of axon" is meant increasing the number of axons or the distance of extension of axons relative to a control condition (e.g., in non-injured neurons). Preferably the increase is by at least 2-fold, 2.5-fold, 3-fold or more.

By "fragment" is meant a portion of a polypeptide that has at least 50% of the biological activity of the polypeptide from which it is derived. This portion contains, preferably, at least 10%, 20%, 30%, 40%, 50%, 60%, 70%, 80%, or 90% of the entire length of the reference nucleic acid molecule or polypeptide. A fragment of a polypeptide or nucleic acid molecule may contain 10, 20, 30, 40, 50, 60, 70, 80, 90, or 100, 200, 300, 400, 500, 600, 700, 800, 900, or 1000 nucleotides or amino acids.

By "neuron" is meant any nerve cell derived from the nervous system of a mammal (e.g., mature neuron of the central nervous system).

By "restorative CNS surgery" is meant any procedure carried out on the central nervous system to enhance neurological function. An exemplary restorative CNS surgery is a peripheral nerve graft or a reinsertion of avulsed nerve roots.

As used herein, the terms "treat," "treatment," "treating," or "amelioration" refer to therapeutic treatments, wherein the object is to reverse, alleviate, ameliorate, inhibit, slow down or stop the progression or severity of a disorder or syndrome, (e.g., neuronal injury, glaucoma, stroke, head trauma, spinal injury, optic injury, ischemia, hypoxia, neurodegenerative disease, multiple sclerosis, infectious disease, cancer, and autoimmune disease) characterized by or making a patient susceptible to neuronal death and or inhibition of axon generation. The term "treating" includes reducing or alleviating at least one adverse effect or symptom of a syndrome. Treatment is generally "effective" if one or more symptoms or clinical markers are reduced. In the case of neuronal death or lack of axon generation, "effective treatment" refers to a treatment that increases the number of surviving neurons and/or increases the number of axons in the neurons) and maintains normal function of the neurons. Alternatively, or in addition, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if the condition is stabilized. The term "treatment" of a disease also includes providing relief from the symptoms or side-effects of the disease (including palliative treatment).

As used herein, the term "gene expression" includes both gene transcription, whereby DNA (or RNA in the case of some RNA-containing viruses) corresponding to a gene is transcribed to generate an RNA molecule and RNA translation, whereby an RNA molecule is translated to generate a protein encoded by the gene. As used herein, the term "protein expression" is used to refer both to gene expression comprising transcription of DNA (or RNA) to form an RNA molecule and subsequent processing and translation of the RNA molecule to form protein and to gene expression comprising translation of mRNA to form protein.

The term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

As used herein, a "subject", "patient", "individual" and like terms are used interchangeably and refers to a vertebrate, preferably a mammal, e.g., a primate, e.g., a human. Mammals include, without limitation, humans, primates, rodents, wild or domesticated animals, including feral animals, farm animals, sport animals, and pets. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish and salmon. The terms, "individual," "patient" and "subject" are used interchangeably herein. In some embodiments, the subject is a human. A subject can be male or female.

A "pharmaceutical composition" refers to a chemical or biological composition suitable for administration to a mammalian subject. Such compositions may be specifically formulated for administration via one or more of a number of routes, including but not limited to, oral, parenteral, intravenous, intraarterial, subcutaneous, intranasal, sublingual, intraspinal, intracerebroventricular, ocular and the like.

Mammals other than humans can be advantageously used as subjects that represent animal models of conditions or disorders disclosed herein. In one embodiment, the subject is a non-human primate animal in a model for neurodegeneration or nervous system (CNS or PNS) injury. Neurons derived from said subjects are also suitable for performance of the methods described herein.

A subject can be one who has been previously diagnosed with or identified as suffering from or under medical supervision for a disorder characterized by neuronal injury. A subject can be one who has undergone or will be undergoing a CNS restorative surgery or axotomy. A subject can be one who is diagnosed and currently being treated for, or seeking treatment, monitoring, adjustment or modification of an existing therapeutic treatment, or is at a risk of developing such a disorder.

As used herein, the term "administering," refers to the placement of an agent (e.g., Armcx1 polypeptide or a vector comprising a nucleic acid sequence encoding the Armcx1 polypeptide) as disclosed herein into a subject by a method or route that results in at least partial delivery of the agent at a desired site (e.g., at or near the site of neuronal injury) such that the administering results in contact of the injured neurons with the agent. Pharmaceutical compositions comprising the agent or cell preparation disclosed herein can be administered by any appropriate route which results in an effective treatment in the subject, e.g., intracerebroventricular ("icv") administration, intranasal administration, intracranial administration, intracelial administration, intracerebellar administration, or intrathecal administration. Administration can be continuous or intermittent. In various aspects, a preparation or an agent can be administered therapeutically; that is, administered to treat an existing disease or condition. In further various aspects, a preparation can be administered prophylactically; that is, administered for prevention of a disease or condition (e.g., neuronal injury).

The term "contacting" as used herein, refers to bringing a disclosed agent (e.g. Armcx1 polypeptide or a vector comprising a nucleic acid sequence encoding the Armcx1 polypeptide) and a cell (e.g., injured neuron), a target receptor, or other biological entity together in such a manner that the agent can affect the activity of the target (e.g., mitochondria, neuronal cell, axon etc.), either directly; i.e., by interacting with the target itself, or indirectly; i.e., by interacting with another molecule, co-factor, factor, or protein on which the activity of the target is dependent.

As used herein, the terms "protein", "peptide" and "polypeptide" are used interchangeably to designate a series of amino acid residues connected to each other by peptide bonds between the alpha-amino and carboxy groups of adjacent residues. The terms "protein", "peptide" and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein", "peptide" and "polypeptide" are used interchangeably herein when referring to a gene product and fragments thereof.

The term "neurodegeneration" refers to a physiological state caused by neuronal injury associated with neuronal loss and/or damage, or loss of axon regeneration. In specific aspects, neurodegeneration refers to neuronal injury resulting in impaired cognitive function.

The term "neuronal injury" as used herein refers to any damage or dysfunction exhibited by neurons, including but not limited to loss of myelin, dendrite retraction, dendritic spine density reduction, axonal damage, loss of axon regeneration and neuronal death.

The term "small molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

As used herein, the term "neurite growth" or "neurite outgrowth" includes the process by which axons or dendrites extend from a neuron. The outgrowth can result in a new neuritic projection or in the extension of a previously existing cellular process. Neurite outgrowth may include linear extension of an axonal process by five cell-diameters or more.

"Central nervous system (CNS) neurons" include the neurons of the brain, the cranial nerves and the spinal cord. The invention relates not only to CNS neurons but also to peripheral neurons that make projections (axons) in CNS, for instance dorsal root ganglion neurons.

As used herein the term "brain injury" is the destruction or degeneration of brain cells is in the brain of a living organism. Brain injuries can result from direct impacts to the head. Such injuries are for example traumatic brain injury and spinal cord injury. The present invention may also be used in treating other neuronal disorders, which include disease, disorder, or condition directly or indirectly affecting the normal functioning or anatomy of a subject's nervous system. The disorder may be a neuronal injury, which can be acute or chronic. Examples of acute injury are those that results from surgery, trauma, compression, contusion, transection or other physical injury, vascular pharmacologic or other insults including hemorrhagic or ischemic damage. Chronic neuronal injury may result from repetitive stress, inflammation/oxidative stress within a neural tissue caused by disease, neurodegenerative or other neurological diseases. The method and compositions provided herein can be beneficial in all diseases where the CSPG matrix is inhibitory for regeneration or maintenance of axons, such as TBI, SCI, multiple sclerosis (MS disease) and amyotrophic lateral sclerosis (ALS).

"Traumatic brain injury, TBI" as used herein includes the condition in which a traumatic blow to the head causes damage to the brain or connecting spinal cord, with or without penetrating the skull. It relates more specifically to the actual mechanical damage that occurs at the type of trauma, such as shearing, tearing and stretching of axons, neurons and blood vessels. Usually, the initial trauma can result in expanding hematoma, subarachnoid hemorrhage, cerebral edema, raised intracranial pressure, and cerebral hypoxia, which can, in turn, lead to severe secondary events due to low cerebral blood flow.

"A spinal cord injury, SCI" as used herein is damage to any part of the spinal cord or nerves at the end of the spinal canal. It often causes permanent changes in strength, sensation and other body functions below the site of the injury. The spinal cord injury may be a complete severing of the spinal cord, a partial severing of the spinal cord, or a crushing or compression injury of the spinal cord. Spinal cord injury SCI proceeds over minutes, hours, days and even months after the initial traumatic insult and can lead to significant expansion of the original damage. These secondary events are a consequence of delayed biochemical, metabolic and cellular changes, which are initiated by the primary injury, and includes inflammation, free radical induced cell death and glutamate excitotoxicity. Axonal sprouting, from surviving neurons, is associated with spontaneous motor and sensory recovery following TBI and SCI. Although the CNS has a limited capacity to regenerate, spontaneous pericontusional axon sprouting does take place approximately 1-2 weeks after trauma. However, this process typically fails due to an inhibitory axonal environment promoted by chon-rioting sulphate proteoglycans (CSPGs). Astrocytes, at the site of injury, produce CSPGs, beyond which the axons cannot regenerate (Silver and Miller, 2004). Inhibition of CSPG activity represents one potential approach to neuroregeneration, following either TBI or SCI. Evidence in support of this theory has been provided through the use of chondroitinase ABC (ChABC, an enzyme that degrades CSPGs) at the site of trauma in rodent models of TBI and SCI. ChABC treatment resulted in an enhanced and prolonged sprouting response with an increase in sensory, motor and autonomic function (Harris et al., 2010, Starkey et al., 2012).

The terms "increased", "increase", "increasing" or "enhance" are all used herein to generally mean an increase by a statically significant amount; for the avoidance of doubt, the terms "increased", "increase", or "enhance", mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. The increase can be, for example, at least 10%, at least 20%, at least 30%, at least 40% or more, and is preferably to a level accepted as within the range of normal for an individual without a given disease.

As used herein the term "reference level" refers to a level of expression of Armcx1 in a "control sample". A control sample can be one that has not been contacted with an agent of the present disclosure. In certain embodiments, a control sample is obtained prior to administration of the inhibitor. In certain embodiments, a reference standard is used as a surrogate for a control sample.

As used herein, the term "vector" is used in reference to a vehicle used to introduce a nucleic acid sequence into a cell. A viral vector is virus that has been modified to allow recombinant DNA sequences to be introduced into host cells or cell organelles. A non-viral vector delivers an amplified amount of agent or nucleic acid to a target tissue, cell or subcellular area, and comprise a lipid based or solid platform suitable for binding a number of substances (e.g., nanoparticle, liposomes etc.).

"Nucleic acid sequence", as used herein, refers to a polymer of nucleotides in which the 3' position of one nucleotide sugar is linked to the 5' position of the next by a phosphodiester bridge. In a linear nucleic acid strand, one end typically has a free 5' phosphate group, the other a free 3' hydroxyl group. Nucleic acid sequences may be used herein to refer to oligonucleotides, or polynucleotides, and fragments or portions thereof, and to DNA or RNA of genomic or synthetic origin that may be single- or double-stranded, and represent the sense or antisense strand.

The terms, "decrease", "reduce", "reduction", "lower" or "lowering," or "inhibit" are all used herein generally to mean a decrease by a statistically significant amount. For example, "decrease", "reduce", "reduction", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

The term "statistically significant" or "significantly" refers to statistical significance and generally means a difference of two standard deviations (2SD) or more.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other than in the operating examples, or where otherwise indicated, all numbers expressing quantities of ingredients or reaction conditions used herein should be understood as modified in all instances by the term "about." The term "about" when used in connection with percentages means ±1% of the value being referred to. For example, about 100 means from 99 to 101.

Although methods and materials similar or equivalent to those described herein can be used in the practice or testing of this disclosure, suitable methods and materials are described below. The abbreviation, "e.g.," is derived from the Latin exempli gratia, and is used herein to indicate a non-limiting example. Thus, the abbreviation "e.g.," is synonymous with the term "for example."

As used in this specification and appended claims, the singular forms "a," "an", and "the" include plural references unless the context clearly dictates otherwise. Thus for example, reference to "the method" included one or more methods, and/or steps of the type described herein and/or which will become apparent to those persons skilled in the art upon reading this disclosure and so forth.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

BRIEF DESCRIPTION OF THE DRAWINGS

(FIG. 1A) In situ hybridization showing Armcx1 mRNA levels in mouse retina cross-sections of wild type and high regeneration mutant PTEN, SOCS3 double KO+CNTF (dKO) and PTEN single KO (PTEN$^{-/-}$) in intact conditions or 3 days post optic nerve crush. Arrow head indicates the retinal ganglion cells layer (GCL). Scale bar: 50 µm. (FIG. 1B) Immunohistochemistry showing the level of endogenous Armcx1 protein in intact retina or 3 days post optic nerve crush in wild type and high regeneration mutant dKO. Tuj1 antibody is used as a RGC marker. Scale bar: 50 µm. (FIG. 1C) Quantification of the percentage of Armcx1 positive RGCs from matched sections of 2-3 animals per condition. One-way ANOVA with Tuckey's multiple comparison test. (FIG. 1D) Scheme of Armcx1 constructs full length and mutant. (FIG. 1E) Immunoblot using anti-HA antibody on HEK cell extract transfected either with Armcx1-HA full length or Armcx1-HA lacking the trans membrane domain (Armcx1ΔTM-HA). Lower panel shows unspecific bands of lower molecular weights used as loading control. (FIG. 1F-1G) Immunohistochemistry using anti-HA antibody of mouse cortical neurons co-transfected with MitoDsRed2 and Armcx1-HA (FIG. 1F) or Armcx1ΔTM-HA (FIG. 1G). Low magnification picture of transfected neurons can be seen in FIG. 7B, discussed below. Lower panel shows signal intensity measured by line scan. Scale bar: 25 µm. c(FIG. 1H) Representative immunoblot showing the specific co-immunoprecipitation (IP) of Miro1-Myc with Armcx1-HA in HEK cells (n=3).

FIGS. 2A-2G show Armcx1 increases mitochondrial transport and axonal outgrowth of adult RGCs. (FIG. 2A) Representative kymographs from live imaging of TMRM labeled mitochondria in RGC axons of adult retina explant from PTEN$^{f/f}$ mice co-injected with AAV-Cre and either AAV-PLAP, AAV-Armcx1 or AAV-Armcx1ΔTM. (FIG. 2B) Percentage of motile and stationary mitochondria in adult RGC axons of the indicated genotypes. n=12-17 axons from 3 independent experiments. Kruskal-Wallis test with Dunn's multiple comparisons test on the number of axons. (FIG. 2C) Box plot showing the moving frequency of mitochondria in RGC axons of adult retina explants from the indicated genotypes. n=221-348 mitochondria from 3 independent experiments (11-16 axons). Kruskal-Wallis test with Dunn's multiple comparisons test (FIG. 2D) Mitochondrial density in adult RGCs axons. n=1116 axons from 3 independent experiments. One-way ANOVA with Tuckey's multiple comparisons test. (FIG. 2E) Tuj1 immunostaining of explants of the indicated genotype. Scale bar: 500 µm (upper row) and 100 µm (lower row). (FIG. 2F) Quantification of the number of axons growing out of the explant normalized by explant's size. n=14-16 explants (21-182 axons) from 2 independent experiments. One-way ANOVA with Tuckey's multiple comparisons test. (FIG. 2G) Quantification of the axonal outgrowth for explants of the indicated genotypes. n=14-16 explants from 2 independent experiments. PTEN$^{-/-}$+Armcx1 vs PTEN$^{-/-}$+PLAP: *$p<0.05$ and **$p<0.01$. PTEN$^{-/-}$+Armcx1 vs PTEN$^{-/-}$+ARMCX1ΔTM: °$p<0.05$ and °°$p<0.01$. One-way ANOVA with Tuckey's multiple.

FIGS. 3A-3D show Effect of Armcx1 overexpression in E18 cortical neurons. (FIG. 3A) Representative kymographs from live imaging of mitochondria in E18 cortical neurons co-transfected with MitoDsRed and either GFP or Armcx1-F2A-GFP. Traces from motile mitochondria were isolated and represented by the bellow kymographs. (FIG. 3B) Percentage of motile and stationary mitochondria per axon of E18 cortical neurons transfected as in A. n=8-10 axons from 3 independent experiments. Two tailed Student's Unpaired t-test on the number of axons. (FIG. 3C) Box plot showing the moving frequency (percentage of time each mitochondria in motion) of mitochondria in axons from cortical neurons of the indicated genotypes. The horizontal line shows the median of the distribution. n=74-137 mitochondria from 3 independent experiments (8-10 axons). Mann-Whitney U test. (FIG. 3D) Representative images of E18 cortical neurons transfected with GFP or Armcx1-F2A-GFP. Scale bar: 100 µm. (FIG. 3E) Box plots showing the distribution of the measurements of the longest neurite in E18 cortical neurons transfected as in (FIG. 3D). N=54-97 neurons from 3 independent experiments ran in duplicate. Mann-Whitney U test.

(FIG. 4A) Optical sections (approximately 14 µm) from whole mount cleared optic nerve from wild type mice injected with AAV-PLAP, AAV-Armcx1 or AAV-Armcx1ΔTM, 15 days post optic nerve crush (dashed line). Axons were labeled with CTB injection. Scale bar: 100 µm. (FIG. 4B) Full nerve thickness z projections of the cleared optic nerves shown in FIG. 4A. (FIG. 4C) Bar plot showing the average total number of axons growing past the injury site based on the z projection of the whole mount cleared optic nerve. Each dot represents one mouse. n=5-8 mice from 2 independent experiments. One-way ANOVA, Tuckey's multiple comparison test. (FIG. 4D) Tuj1 immunohistochemistry on whole mount retina from wild type mice shown in FIG. 4A. The retina from the crushed eye (right) and intact eye (left) of the same animal is shown. Scale bar: 40 µm. (FIG. 4E) Average percentage of RGC survival as measured by Tuj1 staining. Each dot represents one animal. N=5-9 mice from two independent experiments. One-way ANOVA, Tuckey's multiple comparison test.

(FIG. 5A) Optic nerve sections of PTEN$^{f/f}$ mice co-injected with AAV-Cre and the indicated AAVs, 15 days post optic nerve crush (dashed line). Axons were labeled with intraocular CTB injection. Scale bar: 100 µm. Pictures of the full nerve can be seen in FIG. 11, discussed below. (FIG. 5B) Bar plot showing the average estimated number of axons growing past the injury site. Each dot represents one animal (2-6 cryo-sections per animal). n=8-9 mice from 2 independent experiments. One-way ANOVA, Tuckey's multiple comparison test. (FIG. 5C) Tuj1 immunohistochemistry of whole mount retina from PTEN$^{f/f}$ mice shown in FIG. 5A. Retina from the crushed eye (right) and intact eye (left) of the same animal is shown. Scale bar: 40 µm. (FIG. 5D) Average percentage of RGC survival per animal measured by Tuj1 staining. Each dot represents one animal. n=8-9 animals. One-way ANOVA, Tuckey's multiple comparison test. Scale bar: 40 µm. (FIG. 5E) Optic nerve longitudinal sections 15 days post crush of Kcng4-YFP mice injected with CTB and the indicated AAVs. The YFP channel (was visualized as green) shows the axons projecting from the αRGCs (Kcng4-YFP) and the RFP channel (was visualized as red) shows the CTB labeled axons from all RGCs. (FIG. 5F) CTB and YFP axons quantified 0.5 mm from the injury site. n=4 mice per condition. Mann-Whitney Utest. Scale bar: 300 µm.

FIGS. 6A-6F show Armcx1 is necessary for axonal regeneration. (FIG. 6A) Experimental timeline and (left) immunohistochemistry using Armcx1 antibody on retina cross sections of dKO mice injected either with AAV-shScramble or AAV-shArmcx1. Mice were euthanized 3 days post optic nerve crush. (Right) Quantification of the number of Armcx1 positive RGCs 3 days post optic nerve crush in matching sections of the indicated genotypes. Scale bar: 40 µm. n=3 mice randomly chosen from the cohort shown in (FIG. 6B). Two tailed Student's Unpaired t-test. (FIG. 6B) Experimental timeline and (left) optic nerve sections of dKO mice injected with indicated AAVs, 15 days post optic nerve crush (dashed line). Axons were labeled with CTB injection. Scale bar: 100 µm. Pictures of the full nerve are shown in FIG. 12I, discussed below. (Right) Bar plot showing the average estimated number of axons growing past the injury site per animal. Each dot represents one animal (2-6 cryo-sections per mice). n=4 per condition. One-way ANOVA, Tuckey's multiple comparison test. (FIG. 6C) (Left) Tuj1 immunohistochemistry on whole mount retina from dKO mice injected with AAVs as shown in FIG. 6B. Retina from the crushed eye (upper) and intact eye (lower) of the same animal is shown. Scale bar: 40 µm. (Right) Bar plot of the average percentage of RGC survival per animal measured by Tuj1 staining. Each dot represents one animal. N=5 per condition. Two tailed Student's Unpaired t-test.

(FIG. 7A) In situ hybridization showing the mRNA levels of selected members of the Armcx cluster in mouse retina cross-sections of Wt and high regeneration mutant PTEN, SOCS3 double KO+CNTF (dKO) in intact conditions or 3 days post optic nerve crush. Scale bar=50 µm. (FIG. 7B) Immunohistochemistry using anti-HA antibody of mouse cortical neurons co-transfected with MitoDsRed2 and either Armcx1-HA full length or Armcx1ATM-HA. Scale bar=20 µm for the low magnification images and 5 µm for the high magnification images.

(FIG. 8A) Representative images of whole mount retinas from Wt mice injected with the indicated AAVs. 15 days post viral injections, mice were euthanized and immunohistochemistry using indicated antibodies was performed. Scale bar=100 µm. (FIG. 8B) Quantification of the percentage of RGCs infected with AAV-Armcx1-HA (upper) and Armcx1ATM-HA (lower). n=1632-2331 RGCs from 2 retina per conditions. (FIG. 8C) Adult retina explant culture of PTEN$^{f/f}$ mice co-injected with indicated AAVs. Explants were immunostained with Tuj1 antibody. The majority of Cre infected RGCs axons were also infected with MitoDsRed Flex Switch. Scale bar=100 μm.

(FIG. 9A) Quantification of the mitochondrial density in axons of E18 cortical neurons co-transfected with MitoDsRed and either GFP or Armcx1-F2A-GFP. n=8-10 axons from 3 independent experiments. Two tailed Student's Unpaired t-test. (FIG. 9B) Representative kymographs from live imaging experiments of BDNF positive vesicles in E18 cortical neurons co-transfected with BDNF-RFP and either GFP or Armcx1-F2A-GFP. (FIG. 9C) Box plot showing the moving frequency of BDNF positive vesicles in axons from cortical neurons of the indicated genotypes. The horizontal line shows the median of the distribution. n=127-142 vesicles from 9 axons, 3 independent experiments. Mann-Whitney U test.

(FIG. 10A) Tuj1 immunohistochemistry on whole mount retina from mice of the indicated genotypes. Retina from the crushed eye and intact eye of the same animal is shown. Scale bar=40 μm. (FIG. 10B) Average percentage of RGC survival as measured by Tuj1 staining. Each dot represents one animal. n=4-5 animals per condition. One-way ANOVA, Tukey's multiple comparison test. (FIG. 10C) Optical sections (approximately 14 μm) from whole mount cleared optic nerve collected 15 days post optic nerve crush (dashed red line) from Wt mice injected with AAV-PLAP, and Bcl2 mice injected with either AAV-PLAP or AAV-Armcx1. Axons were labeled with intraocular CTB injection. Scale bar=100 μm. (FIG. 10D) Quantification of the average total number of axons growing past the injury site based on the z projection of the whole mount cleared optic nerve. Each dot represents one animal. n=4-5 animals per condition. One-way ANOVA, Holm-Sidak's multiple comparison test.

(FIG. 11A) Optic nerve sections of PTEN$^{f/f}$ mice co-injected with AAV Cre and the indicated AAVs, 15 days post optic nerve crush. Axons were labeled with CTB injection. Scale bar=500 μm. (FIG. 11B) Side by side comparison of optic nerve sections of PTEN$^{-/-}$ mice injected with the indicated AAVs and dKO, 15 days post optic nerve crush (dashed red line). All AAVs were injected and incubated in parallel in all conditions. Axons were labeled with intraocular CTB injection. Scale bar=100 μm. (FIG. 11C) Bar plot showing the average estimated number of axons at 0.2 mm from the injury site. Each dot represents one animal (2-6 cryo-sections per animal). n=4 animals per condition. One-way ANOVA, Tuckey's multiple comparison test.

(FIG. 12A) Immunohistochemistry using the indicated antibody of HEK cells co-transfected with Armcx1-HA and either shRNA-Scramble-GFP, shRNA-Armcx1 #2, shRNA-Armcx1 #5. Scale bar=100 μm (FIG. 12B) Quantification of the intensity ratio from HA and GFP antibody signal. n=5 per conditions from 2 independent experiments with 2-3 technical replicates. One-way ANOVA, Tukey's multiple comparison test. (FIG. 12C) Representative kymographs from live imaging of mitochondria in E18 cortical neurons co-transfected with MitoDsRed and either shRNA Scramble or shRNA Armcx1. (FIG. 12D) Percentage of motile and stationary mitochondria per axon of E18 cortical neurons transfected as in C. n=12-14 axons from 3 independent experiments. Two tailed Student's Unpaired t-test on the number of axons. (FIG. 12E) Box plot showing the moving frequency of mitochondria in axons from cortical neurons transfected as in C. n=142-149 mitochondria from 3 independent experiments (12-14 axons). Mann-Whitney Utest. (FIG. 12F) Quantification of the mitochondrial density in axons of E18 cortical neurons co-transfected with either shScramble or shArmcx1. n=12-14 axons from 3 independent experiments. Two tailed Student's Unpaired t-test (FIG. 12G) Representative images of E18 cortical neurons transfected with shRNA Scramble or shRNA Armcx1 using anti GFP and RFP antibody, respectively. Scale bar=100 μm. (FIG. 12H) Box plots showing the distribution of the measurements of the longest neurites in E18 cortical neurons transfected either with shRNA Scramble or shRNA Armcx1. n=57 neurons per conditions from 3 independent experiments. Mann-Whitney U test. (FIG. 12I) Representative images and quantification of immunohistochemistry on whole mount retinas from Wt mice injected with either shRNA Scramble (upper) or shRNA Armcx1 (lower). Tissues were stained with antibody against Tuj1, GFP (shRNA Scramble) or RFP (shRNA Armcx1). Scale bar=80 μm. (FIG. 12J) Optic nerve sections of dKO mice injected with the indicated AAVs, 15 days post optic nerve crush. Axons were labeled with CTB injection. Images with tissues were stitched and black tiles were added to complete the rectangular shape. Scale bar 500 μm. (FIG. 12K) Experimental time line and (left) CTB-traced optic nerve sections (first column) and Tuj1 immunostaining of whole mount retina (second column) of Wt mice intravitreally injected with either AAV-shScramble or AAV-shArmcx1. Mice were euthanized 5 weeks post injection. Scale bar=100 μm and 40 μm, respectively. (Right) Quantification of RGC survival of mice with the indicated treatment. n=4-5 mice per condition. Mann-Whitney Utest.

DETAILED DESCRIPTION

Figure 1A:
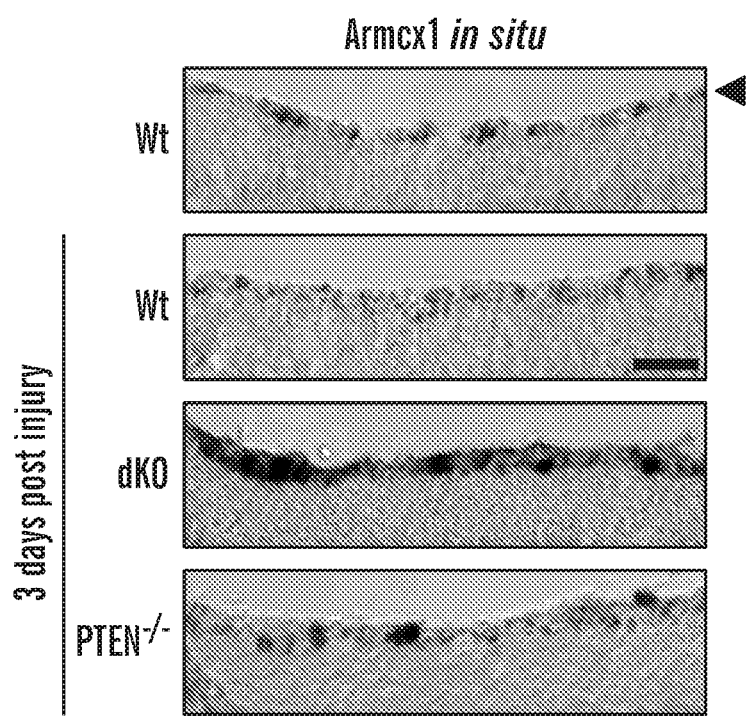
FIGS. 1A-1H show Armcx1 is up-regulated in high regeneration conditions in vivo and localizes to mitochondria.

The present disclosure is based in part on the discovery that expression of Armcx1 correlates with high axonal regeneration, modulates the transport of the axonal mitochondria and promotes neuronal survival and axonal regeneration. Described herein are compositions and methods to promote survival of neurons and/or axons regeneration of neurons. Provided herein are methods and compositions useful for neuronal injury or a disease or disorder causing neuronal injury or resulting from neuronal injury.

The methods and compositions provided herein encompasses contacting neurons with an agent for promoting their survival or axon regeneration. In some embodiments, the agent is a one that is capable of increasing mitochondrial motility in the neurons. In some embodiments, the agent is an Armcx1 polypeptide. In some embodiments, the agent is a vector comprising a nucleic acid sequence encoding an Armcx1 polypeptide.

Armadillo Repeat Containing, X-Linked Protein 1 (Armcx1)

Armcx1 is a protein that is inserted in the mitochondria. As used herein the term "Armcx1" or "Armcx1 protein" or "Armcx1 polypeptide" generally refers to an Armcx1 polypeptide that is similar or identical in sequence to a wild-type Armcx1. In some embodiments, the term "Armcx1 polypeptide" refers to a polypeptide having an amino acid sequence that is at least 80%, at least 85%, at least 90%, at least 95%, at least 97%, at least 99%, or 100%, identical to that of a wild-type Armcx1 and that retains the ability, at a minimum, to increase mitochondrial motility in injured neurons and/or promote survival of injured neurons and/or promote axon regeneration of injured neurons in vivo. Accordingly in some embodiments, "Armcx1 polypeptide" can be full length Armcx1. In some embodiments, "Armcx1" can be a functional fragment of a full length Armcx1, a species homologue and/or functional fragments thereof, an ortholog of Armcx1 and/or functional fragments thereof. The Armcx1 polypeptide can be a mammalian Armcx1 protein. The Armcx1 polypeptide can also be a functional isoform of the full length Armcx1 or functional fragment thereof.

In some embodiments, "Armcx1" is a wild-type Armcx1 of human origin, having the following amino acid sequence, or a functional fragment thereof:

(SEQ ID NO: 1)
```
  1 mgrtreagcv aagvvigaga cycvyrlawg rdenekiwde deestdtsei gvetvkgakt 61 nagagsgakl qgdsevkpev slgledcpgv kekahsgshs gggleakaka lfntlkeqas 121 akagkgarvg tisgnrtlap slpcpggrgg gchptrsgsr aggrasgksk gkarskstra 181 pattwpvrrg kfnfpykidd ilsapdlqkv lnilertndp fiqevalvtl gnnaaysfnq 241 nairelggvp iiakliktkd piirektyna lnnlsvnaen qgkiktyisq vcddtmvcrl 301 dsavqmaglr lltnmtvtnh yqhllsysfp dffallflgn hftkiqimkl iinftenpam 361 trelvsckvp selislfnke wdreillnil tlfenindni kneglassrk efsrsslffl 421 fkesgvcvkk ikalanhndl vvkvkvlkvl tkl
```

(See GenBank Accession No. NP_057692.1, which is incorporated herein by reference in its entirety).

A "functional fragment" refers to fragment of the full length Armcx1 (e.g., corresponding to SEQ ID NO:1) of at least 10, at least 20, at least 30, at least 40, at least 50, at least 60, at least 70, at least 80, at least 90, at least 100, at least 110, at least 120, at least 130, at least 140 consecutive amino acids of full length wild-type Armcx1, that has at least about 70%, 80%, 90%, 100% or more than 100% of the function of wild-type Armcx1 (e.g., of SEQ ID NO:1) at neuronal survival and/or axon regeneration of injured axons in vivo or in vitro. The functional activity can be tested by one of ordinary skill in the art by the assays described in the examples.

The polypeptide and coding nucleic acid sequences of Armcx1 and of other members of the family of human origin and those of a number of animals are publically available, e.g., from the NCBI website and are contemplated for use in the methods and compositions herein. Examples include, but are not limited to, Mouse (GenBank Accession No. AAH21410.1), Rat (GenBank Accession No. AAH85780.1), Bovine (GenBank Accession No. XP_015317042.1).

The nucleic acid sequence of Armcx1 of human origin is known in the art and is available publically for e.g., from genebank Gene ID: 51309, which is incorporated herein by reference in its entirety).

In some embodiments, the Armcx1 polypeptide can be a mammalian homolog of human Armcx1 or a functional fragment thereof. In some embodiments, Armcx1 polypeptide has an amino acid sequence at least 85%, at least 90%, at least 95%, at least 97% or at least 99% identical to the amino acid sequence of SEQ ID NO:1 and increases at least one of i. mitochondrial motility in neurons, ii. survival of injured neurons and iii. axon regeneration of injured neurons. In some embodiments, Armcx1 polypeptide has an amino acid sequence that has at least 85%, at least 90%, at least 95%, at least 97% or at least 99% amino acid sequence homology to amino acid sequence of SEQ ID NO: 1 and increases at least one of i. mitochondrial motility in neurons, ii. survival of injured neurons and iii. axon regeneration of injured neurons. In some embodiments, Armcx1 is a functional fragment of SEQ ID NO:1 of at least 10, at least 20, at least 30, at least 40, at least 50, at least 60, at least 70, at least 80, at least 90, at least 100, at least 110, at least 120, at least 130, at least 140 consecutive amino acids of SEQ ID NO:1, that has at least about 50%, 60%, 70%, 80%, 90%, 100% or more than 100% of the function of wild type Armcx1 (e.g., human Armcx1 of SEQ ID NO:1) of increasing at least one of i. mitochondrial motility in neurons, ii. survival of injured neurons and iii. axon regeneration of injured neurons, in vivo or in vitro. The functional activity can be tested by one of ordinary skill in the art by the assays described in the examples.

Percent (%) amino acid sequence identity for a given polypeptide sequence relative to a reference sequence is defined as the percentage of identical amino acid residues identified after aligning the two sequences and introducing gaps if necessary, to achieve the maximum percent sequence identity, and not considering any conservative substitutions as part of the sequence identity. Percent (%) amino acid sequence homology for a given polypeptide sequence relative to a reference sequence is defined as the percentage of identical or strongly similar amino acid residues identified after aligning the two sequences and introducing gaps if necessary, to achieve the maximum percent homology. Non identities of amino acid sequences include conservative substitutions, deletions or additions that do not affect the biological activity of Armcx1. Strongly similar amino acids can include, for example, conservative substitutions known in the art. Percent identity and/or homology can be calculated using alignment methods known in the art, for instance alignment of the sequences can be conducted using publicly available software software such as BLAST, Align, ClustalW2. Those skilled in the art can determine the appropriate parameters for alignment, but the default parameters for BLAST are specifically contemplated.

In one embodiment, "Armcx1 polypeptide" useful in the methods and compositions described herein consists of, consists essentially of, or comprises an amino acid sequence, or is a fragment thereof derived from SEQ ID NO:1, provided that the polypeptide retains at least one biological activity of full length Armcx1 of SEQ ID NO: 1, the biological activity being selected from at a minimum, increasing i. mitochondrial motility in neurons, ii. survival of injured neurons and iii. axon regeneration of injured neurons, in vivo or in vitro.

The polypeptides described herein can comprise conservative amino acid substitutions at one or more amino acid residues, e.g., at essential or non-essential amino acid residues but will retain a therapeutically or physiologically relevant activity of an inhibitory peptide as that term is described herein. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, in a conservative substitution variant, a nonessential amino acid residue in the polypeptide is preferably replaced with another amino acid residue from the same side chain family.

In some embodiments, Armcx1 can be a variant of wild type Armcx1. The term "variant" as used herein refers to a polypeptide or nucleic acid that is "substantially similar" to a wild-type Armcx1. A molecule is said to be "substantially similar" to another molecule if both molecules have substantially similar structures (i.e., they are at least 50% similar in amino acid sequence as determined by BLASTp alignment set at default parameters) and are substantially similar in at least one therapeutically or physiologically relevant biological activity. A variant differs from the naturally occurring polypeptide or nucleic acid by one or more amino acid or nucleic acid deletions, additions, substitutions or side-chain modifications, yet retains one or more therapeutically relevant, specific functions or desired biological activities of the naturally occurring molecule. (e.g., at least one of i. mitochondrial motility in neurons, ii. survival of injured neurons and iii. axon regeneration of injured neurons, in vivo or in vitro.).

Amino acid substitutions include alterations in which an amino acid is replaced with a different naturally-occurring or a non-conventional amino acid residue. Some substitutions can be classified as "conservative," in which case an amino acid residue contained in a polypeptide is replaced with another naturally occurring amino acid of similar character either in relation to polarity, side chain functionality or size. Substitutions encompassed by variants as described herein can also be "non-conservative," in which an amino acid residue which is present in a peptide is substituted with an amino acid having different properties (e.g., substituting a charged or hydrophobic amino acid with an uncharged or hydrophilic amino acid), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild-type polynucleotide or polypeptide). Polynucleotide changes can result in amino acid substitutions, additions, deletions, fusions and truncations in the polypeptide encoded by the reference sequence. Variants can also include insertions, deletions or substitutions of amino acids in the peptide sequence. To be therapeutically useful, such variants will retain a therapeutically or physiologically relevant activity as that term is used herein.

The Armcx1 polypeptide can be recombinant, purified, isolated, naturally occurring or synthetically produced. The term "recombinant" when used in reference to a nucleic acid, protein, cell or a vector indicates that the nucleic acid, protein, vector or cell containing them have been modified by introduction of a heterologous nucleic acid or protein or the alteration of a native nucleic acid or a protein, or that the cell is derived from a cell so modified. The term "heterologous" (meaning 'derived from a different organism') refers to the fact that often the transferred protein was initially derived from a different cell type or a different species from the recipient. Typically the protein itself is not transferred, but instead the genetic material coding for the protein (often the complementary DNA or cDNA) is added to the recipient cell. Methods of generating and isolating recombinant polypeptides are known to those skilled in the art and can be performed using routine techniques in the field of recombinant genetics and protein expression. For standard recombinant methods, see Sambrook et al, Molecular Cloning: A Laboratory Manual, Cold Spring Harbor Laboratory Press, NY (1989); Deutscher, Methods in Enzymology 182:83-9 (1990); Scopes, Protein Purification: Principles and Practice, Springer-Verlag, NY (1982).

In some embodiments, Armcx1 can be an agonist of wild-type Armcx1, an analog or a derivative thereof. The term "Armcx1 agonist" as defined herein can be a compound that enhances or stimulates the normal biological activity of Armcx1 by increasing transcription or translation of Armcx1-encoding nucleic acid, and/or by inhibiting or blocking activity of a molecule that inhibits Armcx1 expression or Armcx1 activity, and/or by enhancing normal Armcx1 biological activity (including, but not limited to enhancing the stability of Armcx1 or enhancing binding of Armcx1 to a receptor and/or directly binding to and activating a potential Armcx1 receptor. The "biological activity" can be defined herein as including at least one of the activity selected from e.g., increasing i. mitochondrial motility in neurons, ii. survival of injured neurons and iii. axon regeneration of injured neurons, in vivo or in vitro. The activity of the agonist can be for example, at least 80%, at least 85%, at least 90%, at least 95%, at least 97% or at least 99% of the biological activity of human Armcx1 of SEQ ID NO:1.

It is contemplated herein that in the methods and compositions can comprise Armcx1 analogs or Armcx1 derivatives. By "Armcx1 analog" it is meant a peptide whose sequence is derived from that of Armcx1 including insertions, substitutions, extensions, and/or deletions, having at least some amino acid identity to Armcx1 or region of an Armcx1 polypeptide. Analogs may have at least 50 or 55% amino acid sequence identity with a native Armcx1 (e.g., human Armcx1, SEQ ID NO: 1) or at least 70%, 80%, 90%, or 95% amino acid sequence identity with a native Armcx1. In one embodiment, such analogs may comprise conservative or non-conservative amino acid substitutions (including non-natural amino acids and L and D forms). Armcx1 agonist analogs are analogs as herein described and function as an Armcx1 agonist.

An "Armcx1 derivative" is defined as a molecule having the amino acid sequence of a wild-type Armcx1 (e.g., human Armcx1, SEQ ID NO: 1) or analog thereof, but additionally having a chemical modification of one or more of its amino acid side groups, alpha.-carbon atoms, terminal amino group, or terminal carboxylic acid group for example by ubiquitination, labeling, pegylation (derivatization with polyethylene glycol) or addition of other molecules. A chemical modification includes, but is not limited to, adding chemical moieties, creating new bonds, and removing chemical moieties. Such modifications can improve the molecule's solubility, absorption, biological half-life, etc. The modifications can alternatively decrease the toxicity of the molecule, or eliminate or attenuate an undesirable side effect of the molecule, etc. Moieties capable of mediating such effects are disclosed in Remington's Pharmaceutical Sciences, 18th edition, A. R. Gennaro, Ed., MackPubl., Easton, Pa. (1990). Furthermore, one or more side groups, or terminal groups, may be protected by protective groups known to the ordinarily-skilled synthetic chemist. The term "functional" when used in conjunction with "derivative" or "variant" refers to a polypeptide which possesses a therapeutically or physiologically relevant biological activity that is substantially similar to a biological activity of the entity or molecule of which it is a derivative or variant. By "substantially similar" in this context is meant that at least 50% of the relevant or desired biological activity of a corresponding wild-type peptide is retained. In some embodiments, the derivative retains at least 60%, at least 70%, at least 80%, at least 90%, at least 95%, or more, including 100% or even more (i.e., the derivative or variant has improved activity relative to wild-type) of the Armcx1.

In some embodiments, the agonist of wild-type Armcx1, an analog or a derivative thereof, retains at least one biological activity of full length ANG of SEQ ID NO: 1, the biological activity being selected from at a minimum, at least one of i. mitochondrial motility in neurons, ii. survival of injured neurons and iii. axon regeneration of injured neurons, in vivo or in vitro. In some embodiments, the agonist of wild-type Armcx1, an analog or a derivative thereof, retains at least 50%, at least 60%, at least 70%, at least 80%, at least 90%, at least 100% or more than 100% of the biological activity of full length Armcx1 of SEQ ID NO:1.

In some embodiments, an agent of the methods and compositions herein, is a vector comprising a nucleic acid sequence encoding for an Armcx1 polypeptide. In some embodiments, the vector is a viral vector. In some embodiments, the vector is non-viral vector. In some embodiments, the vector is an expression vector comprising a nucleic acid sequence encoding an Armcx1 polypeptide. Viral and non-viral-based gene transfer methods can be used to introduce nucleic acids encoding Armcx1 polypeptides to cells or target tissues of the subject. Such methods can be used to administer nucleic acids encoding Armcx1 polypeptides to cells in vitro. Alternatively, or in addition, such polynucleotides can be administered for in vivo or ex vivo gene therapy uses. Non-viral vector delivery systems include DNA plasmids, naked nucleic acid, and nucleic acid complexed with, for example, a liposome or other delivery vehicle. Viral vector delivery systems include both DNA and RNA viruses, and can have either episomal or integrated genomes after delivery to the cell. Gene therapy procedures are described, for example, in Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described, e.g., in U.S. Pat. Nos. 5,049,386, 4,946,787; and 4,897,355, and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res.52: 4817-4820 (1992); U.S. Pat. Nos. 4,186,183, 4,217,344, 4,235,871, 4,261,975, 4,485,054, 4,501,728, 4,774,085, 4,837,028, and 4,946,787).

RNA or DNA viral based systems can be used to target the delivery of polynucleotides carried by the virus to specific cells in the body and deliver the polynucleotides to the nucleus. Viral vectors can be administered directly to patients (in vivo) or they can be used to transfect cells in vitro. In some cases, the transfected cells are administered to patients (ex vivo). Conventional viral based systems for the delivery of polypeptides of the invention could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene, and high transduction efficiencies.

Biological Activity of Agent

The technology herein is partly based on the discovery that protein Armcx1 increases mitochondrial motility, survival of injured neurons and regeneration of axon post injury. Accordingly the minimum set of biological activity of an agent (e.g., Armcx1) is at least one or combination of; i. increasing mitochondrial motility, ii. promoting survival of neurons (e.g. injured neurons) or iii. promoting regeneration of axons in the neurons (e.g., injured neurons).

Increased mitochondrial motility can be e.g., increase in the total pool of motile mitochondria or increase in the fraction of time mitochondria is in motion in neurons contacted by the agents, compared to that in absence of contact with the agent. The increase can be e.g., at least 10%, 20%, 30%, 40%, 50%, 55%, 60%, 65%, 70%, 75% or more relative to in neurons not contacted with the agent.

Increased survival of neurons is indicated by the number of neurons surviving from a specific injury or condition upon contact with an agent disclosed herein (e.g., Armcx1 polypeptide), as compared to the number of neurons surviving in absence of said contact, and also by the length of time the survival persists upon contact with an agent disclosed herein (e.g., Armcx1 polypeptide), as compared to that in absence of contact. Survival is considered to be sustained if it persists for an extended period of time post-injury (e.g., greater than 2 weeks post-injury, greater than 3 weeks, and greater than 4 weeks postinjury). In one embodiment, greater than 10% of neurons (e.g., 15%, 20%, 25%, 30%, 35%, 0%, 45%, 50%, 55%, 60%, 65%, 70% and 75%), survive upon contact with one or more agents disclosed herein. In one embodiment, greater than 20% of neurons (e.g., 25%, 30%, 35%, 0%, 45%, 50%, 55%, 60%, 65%, 70% and 75%), survive for an extended period of time post-injury.

Increased regeneration or outgrowth is indicated by the number of neurons (injured and also uninjured) and by extended length of the axonal outgrowth of the neurons upon contact with the agent disclosed herein (e.g., Armcx1), as compared to that in absence of the said contact, and by the time frame post-injury that the outgrowth occurs upon contact with an agent disclosed herein (e.g. Armcx1), as compared to the time frame postinjury that outgrowth occurs in absence of said contact. Increased regeneration and axonal outgrowth occurs if greater than 10% or greater than 20% (e.g., 15%, 20%, 25%, 30%, 35%, 0%, 45%, 50%, 55%, 60%, 65%, 70% and 75%) of the neurons regenerate injured axons or generate new axons. In some embodiments, the regenerated axons extend at least 0.5 mm distal to the lesion epicenter. In one embodiment, greater than 10% or greater than 20% (e.g., 15%, 20%, 25%, 30%, 35%, 0%, 45%, 50%, 55%, 60%, 65%, 70% and 75% of neurons regenerate injured axons or generate axons over 1 mm distal to the lesion site. In one embodiment, greater than 10% (e.g., 15%, 20%, 25%, 30%, 35%, 0%, 45%, 50%, 55%, 60%, 65%, 70% and 75%) or greater than 20% of neurons regenerate or generate new axons that extend at least 2 mm distal from the lesion site.

Other Agents

An activator of protein translation (e.g., a mTOR pathway activator; a PTEN inhibitor; a TSC1/2 inhibitor; an Akt activator; a Ras/MEK pathway activator; or a PRAS40 inhibitor can promote the survival of, or axon regeneration in the neuron. See for e,g, US 20090305333 A1, the contents of which are incorporated herein in its entirety. PTEN inhibitors e.g., in US 20090305333 A1, U.S. Pat. No. 8,367,352 B2, US 20140213609 A1 (the contents of which are incorporated herein by reference in their entireties) can be useful in the methods and compositions herein, in combination with the agents disclosed herein (e.g., agents increasing mitochondrial motility, Armcx1 polypeptide). Inhibition of SOCS3 was reported to promote neuron regeneration (US20110124706 A1, the contents of which are incorporated by reference herein in its entirety).

The inventors discovered that when combined with PTEN deletion and/or inhibition of SOCS3, overexpression of Armcx1, significantly increased the survival of or, axon regeneration in neurons compared to inhibition of PTEN or SOCS3 alone. It has been reported that a combination of PTEN inhibitor and inhibitor of SOCS3, promoted sustained survival of, and/or axon regeneration in injured neurons in comparison to PTEN inhibitor or SOCS3 inhibitor alone (See for example reference US 20140256795 A1, the contents of which are incorporated herein in its entireties.) Accordingly, in one aspect, the methods described herein further comprises contacting injured neurons with other agents that can promote at least one of; i. mitochondrial motility, ii. survival of injured axons, or iii. axon regeneration in injured neurons in combination with the agents disclosed herein (e.g., agents that increase mitochondrial motility, Armcx1).

The agents of the present disclosure (e.g., agents that increase mitochondrial motility, Armcx1 polypeptide, or vector comprising a nucleic acid sequence encoding Armcx1 polypeptide).

In some embodiments, the methods and compositions of the present disclosure can comprise contacting the injured neurons or administering to the subject, an effective amount of one or more other agents selected from activator of protein translation, PTEN inhibitor, inhibitor of suppressor of cytokine signaling 3 (SOCS3) in combination with the agents disclosed herein (e.g., e.g., agents increasing mitochondrial motility, Armcx1 polypeptide, vector comprising a nucleic acid sequence encoding an Armcx1 polypeptide). In some embodiments, the methods and compositions herein comprises of contacting neurons with effective amounts of combination of Armcx1 polypeptide, inhibitor of PTEN and inhibitor of SOCS3. In some embodiments, the neurons can also be contacted with nerve growth factor, trophic factor, or hormone that promotes neural cell survival, growth, and/or differentiation, such as brain-derived neurotrophic factor (BDNF), ciliary neurotrophic factor (CNTF), nerve growth factor (NGF), inosine, oncomodulin, NT-3, etc, in addition to the agents disclosed herein (e.g., Armcx1 polypeptide), and/or one of the other agents disclosed above (e.g., activator of protein translation, PTEN inhibitor, inhibitor of SOCS3).

In one embodiment, the injury results from acute spinal cord injury and the method additionally comprises contacting the neuron with methylprednisolone sufficient to reduce inflammation of the spinal cord. In one embodiment, the agents are administered in combination with trophic and/or growth factors (e.g., denervation-induced cytokines) known in the art to promote or enhance neuronal survival/regeneration, growth and/or differentiation. Examples include, without limitation, brain-derived neurotrophic factor (BDNF), ciliary neurotrophic factor (CNTF) (WO2011/066182), fibroblast growth factor (FGF), chondroitiniase, nerve growth factor (NGF), NT-3 (Piantino et al, Exp Neurol. 2006 October; 201(2):359-67), inosine (Chen et al, Proc Natl Acad Sci USA. (2002) 99:9031-6; U.S. Pat. No. 6,551,612 to Benowitz; U.S. Pat. No. 6,440,455 to Benowitz; and US Pat Publ 20050277614 to Benowitz), oncomodulin (Yin et al, Nat Neurosci. (2006) 9:843-52; US Pat Publ 20050054558 to Benowitz; US Pat Publ 20050059594 to Benowitz; and U.S. Pat. No. 6,855,690 to Benowitz). Another such agent is an agent to remove extracellular matrix molecules (e.g., chondroitin sulphate proteoglycans) that are inhibitory to neuronal outgrowth, such as chondroitenase ABC (ChABC), which breaks up chondroitin sulphate proteoglycans.

In one embodiment, the agents are administered in combination with one or more factors that facilitate neuronal synapse formation. Examples of such factors include, without limitation, activators of Rab3A, NMDA-I, synapsin-1, tetanus toxin receptor, BDNF-receptor and a GABA receptor. Such factors are described in U.S. Patent Application Publication 2008/0214458. Neuronal synapse formation can be modulated, for example, by modulating the activity of the transcriptional factor myocyte enhancer factor 2 (MEF2) (e.g., MEF2A), MEF2C, MEF2D, dMEF2, CeMEF2, Activating transcription factor 6 beta.

(ATF6), Estrogen related receptor alpha (ERR1), Estrogen related receptor beta (ERR2), Estrogen related receptor gamma (ERR3), Erythroblastosis virus E26 oncogene homolog 1 (ETS1), Forkhead box protein C2 (FOXC2), Gata binding factor 1 (GATA-1), Heat shock factor 1 (HSF1), HSF4, MLL3, Myeloblastosis oncogene homolog (MYB), Nuclear receptor coactivator 2 (NCOA2), Nuclear receptor corepressor 1 (NCOR1), Peroxisome proliferative activated receptor gamma (PPARg), SMAD nuclear interacting protein 1 (SNIP1), SRY-box containing protein 3 (SOX3), SOX8, SOX9, Sterol regulatory element-binding transcription factor 2 (SREBP2), or Thyroid hormone receptor beta-1 (THRB1) (described in U.S. Patent Application Publication 20100112600).

The other agent(s) can be administered to the same site or to a different site as the agents of the present disclosure (e.g., agents that increase mitochondrial motility, Armcx1 polypeptide or a vector comprising a nucleic acid sequence encoding an Armcx1 polypeptide). The other agent may be contacted to the same site of the neuron or to a different site of the neuron. In one embodiment, the agents of the present disclosure (e.g., agents that increase mitochondrial motility, Armcx1 polypeptide or a vector comprising a nucleic acid sequence encoding an Armcx1 polypeptide) is contacted to the neuron(s) at the neuron's region of origin in the brain (e.g., by administration to cortical neurons at the cerebral ventricle) and the other agent is contacted to the neuron at the site of injury (e.g., the lesioned axon such as a cortical spinal tract axon). Other combinations of site of contact and routes of administration discussed herein are also envisioned.

The contacting with one or more of the other agents (e.g., activator of protein translation, PTEN inhibitor, inhibitor or SOCS3, BDNF, CNTF, inosine, oncomodulin, NT-3) can occur prior to, with or after the contacting with the agents disclosed herein (e.g., Armcx1 polypeptide). An effective amount of the inhibitors are contacted with the neuron using a suitable method sufficient to promote sustained survival of the neuron and/or regeneration and/or sustained compensatory outgrowth of the neuronal axon. An effective amount is the amount required to produce statistically significant and reproducible sustained survival, sustained regeneration, or a combination of both, as compared to an appropriate control. For in vitro methods, the inhibitors are, for example, added to the culture medium, usually at nanomolar or micromolar concentrations. The respective inhibitors can be added in the same formulation, or in different formulations.

For in vivo applications, one or more other agents can be administered to the subject by any method that results in contacting both a therapeutically effective amount of each to the neuron at relatively the same time, or in some embodiments, separately at different times. The respective other agents can be administered at the same time or at different times, depending upon various factors associated with each inhibitor (e.g., half-life, administration route, etc.). The respective other agents can be administered by the same route of administration or through different routes of administration e.g., orally, by intravenous (i.v.) bolus, by i.v. infusion, subcutaneously, intramuscularly, ocularly (intraocularly, periocularly, retrobulbarly, intravitreally, subconjunctivally, topically, by subtenon administration, etc., intracranially, intraperitoneally, intraventricularly, intrathecally, by epidural, etc. The administration of the respective other agents can be for differing prolonged periods, or for the same length of period such that their activities on the contacted neurons completely or substantially overlap. The respective other agents can be administered in a formulation which contains one or more of other agents (a pharmaceutical composition, as described herein), or they can be in separate formulations (separate pharmaceutical compositions) for separate administration.

It is contemplated herein, that contacting the neurons with a combination of agents disclosed herein and those known in the art results in increased survival of, and/or axon regeneration of injured neurons compared to when the neurons are contacted with individual agents alone.

Increased survival of neurons is indicated by the number of neurons surviving from a specific injury or condition, as compared to the number of neurons surviving as a result of the effects of the individual agent (either Armcx1, PTEN or SOCS3), and also by the length of time the survival persists, as compared to the length of time survival persists as a result of the effects of the individual agent (either Armcx1, PTEN or SOCS3). Survival is considered to be sustained if it persists for an extended period of time post-injury (e.g., greater than 2 weeks post-injury, greater than 3 weeks, and greater than 4 weeks postinjury). In one embodiment, greater than 10% of neurons (e.g., 15%, 20%, 25%, 30%, 35%, 0%, 45%, 50%, 55%, 60%, 65%, 70% and 75%), survive upon contact with one or more agents disclosed herein. In one embodiment, greater than 20% of neurons (e.g., 25%, 30%, 35%, 0%, 45%, 50%, 55%, 60%, 65%, 70% and 75%), survive for an extended period of time post-injury.

Increased regeneration or outgrowth is indicated by the number of neurons (injured and also uninjured) and by extended length of the axonal outgrowth of the neurons, as compared to the number of neurons and extended length of the axonal outgrowth of the neurons that results from the effects of the individual agent (e.g., either Armcx1, PTEN or SOCS3), and by the time frame post-injury that the outgrowth occurs, as compared to the time frame postinjury that outgrowth occurs resulting from the effects of the individual agent (e.g., either PTEN or SOCS3). Increased regeneration and axonal outgrowth occurs if greater than 10% or greater than 20% (e.g., 15%, 20%, 25%, 30%, 35%, 0%, 45%, 50%, 55%, 60%, 65%, 70% and 75%) of the neurons regenerate injured axons or generate new axons. In some embodiments, the regenerated axons extend at least 0.5 mm distal to the lesion epicenter. In one embodiment, greater than 10% or greater than 20% (e.g., 15%, 20%, 25%, 30%, 35%, 0%, 45%, 50%, 55%, 60%, 65%, 70% and 75%) of neurons regenerate injured axons or generate axons over 1 mm distal to the lesion site. In one embodiment, greater than 10% (e.g., 15%, 20%, 25%, 30%, 35%, 0%, 45%, 50%, 55%, 60%, 65%, 70% and 75%) or greater than 20% of neurons regenerate or generate new axons that extend at least 2 mm distal from the lesion site.

Sustained regeneration and axonal outgrowth can be indicated by a significant amount of outgrowth occurs on or after 2 weeks post-injury. For example significant outgrowth occurs for up to 3 weeks or 4 weeks post-injury.

Neurons

The methods and compositions described herein are suited for the promotion of survival of, and/or axon regeneration in and sustained axonal outgrowth of CNS (central nervous system) neurons. It is contemplated herein that the methods and compositions of the present disclosure are not limited to neurons of the CNS, but can also be adapted for PNS (peripheral nervous system) neurons. CNS neurons include, without limitation, a cerebellar granule neuron, or an ocular neuron. In one embodiment, the neuron is the optic nerve. In one embodiment, the neuron is a sensory neuron (e.g., dorsal root ganglion (DRG) sensory neuron). As used herein, the term "PNS neurons" is intended to include the neurons commonly understood as categorized in the peripheral nervous system, including sensory neurons and motor neurons. The present invention provides methods and compositions for preventing and/or treating peripheral nerve damage (peripheral neuropathy) in a subject. Peripheral nerves such as dorsal root ganglia, otherwise known as spinal ganglia, are known to extend down the spinal column. These nerves can be injured as a result of spinal injury. Such peripheral nerve damage associated with spinal cord injury can also benefit from neuron axonal outgrowth produced by the methods described herein. In some embodiments, the neurons are in the spinal cord. In some embodiments, the neurons are in the optic nerve. In some embodiments, the neurons are axotomized neurons (for example during surgery). In some embodiments, the neuron is human. In one embodiment, the neuron is a terminally differentiated neuron. In one embodiment, the neuron is an adult neuron (e.g., in a subject that has reached maturity, such as in humans older than 18 years). In one embodiment, the neuron is non-embryonic. In one embodiment, the neuron is in an immature organism (e.g., embryo, infant, child). All mammals are suitable subjects for performance of the methods described herein. In one embodiment, the mammal is a human, non-human primate, companion animal (e.g., dog, cat), livestock animal (e.g., horse, cow, pig, sheep), or rodent (mouse, rat, rabbit). In one embodiment, the subject is a non-human primate animal in a model for neurodegeneration or nervous system (CNS or PNS) injury. Neurons derived from said subjects are also suitable for performance of the methods described herein. In some embodiments, the neurons are injured neurons.

Neuronal Injury

As used in the art, the term injury refers to damage (e.g., to a system or a cell). Damage to a system is evidenced by aberrant function, reduction of function, loss of function of the system, or loss of essential components (e.g., specialized cells such as neurons). Damage or injury to a specific neuron is also evidenced by aberrant function, loss of function, reduced function, and/or cell death. Some forms of injury to a neuron can be directly detected (e.g., by visualization as with a severed or crushed neuronal axon). Accordingly, in some embodiments, the methods disclosed herein comprises an antecedent step of determining that the neuron is injured and/or has axotomy-induced stress. Neuronal injury can result from a variety of insults, including, but not limited to physical injury (e.g., severing, crushing), toxic effects, atrophy (e.g., due to lack of trophic factors).

The term "neuronal injury" as used herein refers to any damage or dysfunction exhibited by neurons, including but not limited to loss of myelin, dendrite retraction, dendritic spine density reduction, axonal damage, loss of axon regeneration and neuronal death. Neuronal injury may be complete loss of a neuron, or loss of a part of the neuron (e.g., an axon). Such damage may results from acute or traumatic injury to the neuron (e.g., crush, severing) such as the result of external physical trauma to the subject (e.g., contusion, laceration, acute spinal cord injury, traumatic brain injury, cortical impact, etc.). Acute or traumatic injury to a neuron can also result from an acute condition, such as stroke, that results in acute ischemia to the neuron resulting in acute injury. The specific location of neuronal injury will vary with the specific cause of the injury, and the specific individual. In one embodiment, the injured CNS neuron is located in CNS white matter, particularly white matter that has been subjected to traumatic injury. The specific location of a lesion to a specific neuron will vary with respect to the injury. In one embodiment, the injury is in the axon or dendrite of a neuron. In on embodiment, the injured neuron is in the spinal cord. In one embodiment, the injured neuron is in the optic nerve.

Injury to a neuron may also be incurred from a chronic injury (e.g., repetitive stress injury) or condition (e.g., chronic inflammation or disease). Chronic injury leads to neurodegeneration such as caused by neurotoxicity or a neurological disease or disorder (e.g. Huntington's disease, Parkinson's disease, Alzheimer's disease, multiple system atrophy (MSA), etc.).

In one embodiment of the methods disclosed herein, injured neurons results from an ocular injury or disorder (e.g. toxic amblyopia, optic atrophy, higher visual pathway lesions, disorders of ocular motility, third cranial nerve palsies, fourth cranial nerve palsies, sixth cranial nerve palsies, internuclear ophthalmoplegia, gaze palsies, eye damage from free radicals, etc.), or an optic neuropathy (e.g. ischemic optic neuropathies, toxic optic neuropathies, ocular ischemic syndrome, optic nerve inflammation, infection of the optic nerve, optic neuritis, optic neuropathy, papilledema, papillitis, retrobulbar neuritis, commotio retinae, glaucoma, macular degeneration, retinitis pigmentosa, retinal detachment, retinal tears or holes, diabetic retinopathy, iatrogenic retinopathy, optic nerve drusen, etc.). Injury to a neuron can be detected by the skilled practitioner through a variety of assays known in the art. Loss of function assays can be used to determine neuronal injury. Physical damage to the neuron (e.g., axonal crushing or severing) can sometimes be observed diagnostically through routine methods. One way to detect a lesion is through detection of axotomy-induced stress.

Diseases and Disorders

The methods and compositions disclosed herein are useful for the treatment of neuronal injury. The methods and compositions of the invention are useful for treatment of diseases or disorders resulting from or leading to the neuronal injury described herein. In some embodiments, the disorder is selected from the group consisting of glaucoma, stroke, head trauma, spinal injury, optic injury, ischemia, hypoxia, neurodegenerative disease, multiple sclerosis, infectious disease, cancer, and autoimmune disease.

In some embodiments, the methods and compositions described herein can be used specifically to treat damage associated with peripheral neuropathies including, but not limited to, the following: diabetic neuropathies, virus-associated neuropathies, including acquired immunodeficiency syndrome (AIDS) related neuropathy, infectious mononucleosis with polyneuritis, viral hepatitis with polyneuritis; Guillian-Barre syndrome; botulism-related neuropathy; toxic polyneuropathies including lead and alcohol-related neuropathies; nutritional neuropathies including subacute combined degeneration; angiopathic neuropathies including neuropathies associated with systemic lupus erythematosis; sarcoid-associated neuropathy; carcinomatous neuropathy; compression neuropathy (e.g. carpal tunnel syndrome) and hereditary neuropathies, such as Charcot-Marie-Tooth disease, peripheral nerve damage associated with spinal cord injury can also be treated with the present method. The subject is treated in accordance with the present method for CNS or peripheral nerve damage as the result injury, including those listed above. Subjects at risk for developing such CNS or damage are also so treated.

Administration

Agent of the present disclosure is contacted with the neuron using a suitable drug delivery method and treatment protocol sufficient to promote regeneration of the axon. For in vitro methods, the agent is added to the culture medium, usually at nanomolar or micromolar concentrations. For in vivo applications, the agent can be administered orally, by intravenous (i.v.) bolus, by i.v. infusion, subcutaneously, intramuscularly, ocularly (intraocularly, periocularly, retrobulbarly, intravitreally, subconjunctivally, topically, by subtenon administration, etc.), intracranially, intraperitoneally, intraventricularly, intrathecally, by epidural, etc. Depending on the intended route of delivery, the agent or compositions comprising the agent may be administered in one or more dosage form(s) (e.g. liquid, ointment, solution, suspension, emulsion, tablet, capsule, caplet, lozenge, powder, granules, cachets, douche, suppository, cream, mist, eye drops, gel, inhalant, patch, implant, injectable, infusion, etc.). The dosage forms may include a variety of other ingredients, including binders, solvents, bulking agents, plasticizers etc. In a specific embodiment, the agent is contacted with the neuron using an implantable device that contains the activator and that is specifically adapted for delivery to a CNS axon of neuron. Examples of devices include solid or semi-solid devices such as controlled release biodegradable matrices, fibers, pumps, stents, adsorbable gelatin (e.g. Gelfoam), etc. The device may be loaded with premeasured, discrete and contained amounts of the activator sufficient to promote regeneration of the axon. In a particular embodiment, the device provides continuous contact of the neuron with the activator at nanomolar or micromolar concentrations, preferably for at least 2, 5, or 10 days.

Administration is to a subject by a route that results in contacting an effective amount of the agents disclosed herein (e.g., agent that increases mitochondrial mobility, Armcx1 polypeptide or a vector comprising a nucleic acid sequence encoding an Armcx1 polypeptide) to the target neuron(s). As the term is used herein, the target neuron is the neuron which is intentionally contacted by the administered agent. A target neuron can be an injured neuron or a non-injured neuron (e.g., for compensatory axonal outgrowth to a region of denervation, or used as a control in the methods herein). The target neuron may be contacted at one or more specific target sites of the neuron. As the term is used herein, the target site of the neuron is the region of the neuron to which the agent is intentionally contacted. Regions of the neuron include the dendrites, cell body, and the axon. In some embodiments, the target site of the neuron is the mitochondria of the neuron. Methods for targeting the agents to mitochondria of a cell are known in the art. See for e.g., AAPS J. 2006 June; 8(2): E277-E283., Antioxid Redox Signal. 2011 Dec. 15; 15(12):3021-38, Biochim Biophys Acta. 2008 July-August; 1777(7-8):1028-31, the contents of which are incorporated herein by reference in their entireties. Non-limiting exemplary methods for targeting the agents and compositions disclosed herein to the mitochondria of a neuron can include for e.g., conjugation of an agent with a lipohilic molecular group, encapsulation of agents in a liposome or nanoparticle.

Since regeneration and axonal generation in the treatment of a neuronal injury includes compensatory promotion of axonal outgrowth of uninjured neurons, benefit is expected from mere delivery of the inhibitors and/or other agents to an injury site. As such, suitable target neurons are actual damaged neurons, and also neurons that are in the immediate area of an injury site or an area of dennervation. The specific location and extent of an injury site can be determined by the skilled practioner. Examples of injury sites are the site of physical damage or disruption of neuronal activity. The immediate area of an injury site will vary with respect to the specific injury, the nature of the injury, and the nature of the injured neurons (e.g., axonal length, specific function, etc.) and can be determined by the skilled practitioner. Typically a lesion is in the axon of the injured neuron. In one embodiment, the immediate area of the injury site is within about 1-10 mm of identified damaged neurons (e.g., 1, 2, 3, 4, 5, 6, 7, 8, 9, or 10 mm). In one embodiment, the administration is localized so as to be highly targeted to a specific site. In one embodiment, the administration is systemic, and results in delivery of the appropriate concentration to the specific site.

Depending on the intended route of delivery, the compositions may be administered in one or more dosage form(s) (e.g. liquid, ointment, solution, suspension, emulsion, tablet, capsule, caplet, lozenge, powder, granules, cachets, douche, suppository, cream, mist, eye drops, gel, inhalant, patch, implant, injectable, infusion, etc.). The dosage forms may include a variety of other ingredients, including binders, solvents, bulking agents, plasticizers etc.

In a specific embodiment, the inhibitors are contacted with the neuron using an implantable device that contains the inhibitors and that is specifically adapted for delivery to a neuron. Examples of devices include solid or semi-solid devices such as controlled release biodegradable matrices, fibers, pumps, stents, adsorbable gelatin (e.g. Gelfoam), etc. The device may be loaded with premeasured, discrete and contained amounts of the inhibitors sufficient to promote sustained regeneration or sustained survival of the neuron. In one embodiment, the device provides continuous contact of the neuron with the inhibitors at nanomolar or micromolar concentrations, (e.g., for at least 2, 5, or 10 days, or for at least 2, 3, or 4 weeks, or for greater than 4 weeks, e.g., 5, 6, 7, or 8 weeks).

In one embodiment, administration of an agent disclosed herein to a subject (e.g., in a single or in different pharmaceutical compositions, with or without other agents described herein) results in the inhibitors directly contacting an injured neuron in need of regeneration. In one embodiment, administration results in contacting neurons proximal to a site of neuronal injury. Neurons can be contacted at any point along their length (e.g., at the axon, dendrite and/or the cell body).

Administration to the subject can be by any one or combination of a variety of methods (e.g., intravenously, intracortically, intracerebrally, intrathecally, intranasally, ocularly, parenterally, enterally and/or topically or locally at the injured neuron.). The appropriate method(s) will depend upon the circumstances of the individual (e.g. the location of the target neuron(s), the condition of the individual, the desired duration of the contact, whether local or systemic treatment is desired). The administration can be by any methods described herein that will result in contact of sufficient agent(s) to the target neuron to promote survival of neuron, axon regeneration, or a combination of both. For instance, parenteral, enteral and topical administration can be used. The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, intracortical, intracerebral, intranasal, ocular, sub capsular, subarachnoid, intraspinal, intracerebro spinal, and intrastemal injection and infusion. Enteral administration involves the esophagus, stomach, and small and large intestines (i.e., the gastrointestinal tract). The phrases "systemic administration," "administered systemically", "peripheral administration" and "administered peripherally" as used herein mean the administration of a compound other than directly into the central nervous system, such that it enters the animal's system and, thus, is subject to metabolism and other like processes, for example, subcutaneous administration. Administration may be topical (including ophthalmic, vaginal, rectal, intranasal, epidermal, and transdermal), oral or pulmonary administration, e.g., by inhalation or insufflation, or intracranial, e.g., intrathecal or intraventricular, administration, topically to the eye, or by intraocular injection.

Specific routes of administration and the dosage regimen will be determined by skilled clinicians based on factors such as the exact nature of the condition being treated, the severity of the condition, and the age and general physical condition of the patient. Provided herein are methods for promoting survival of neuron, axon regeneration, or a combination of both in an injured neuron of central nervous system neurons following an injury. The method involves administering to a subject an agent that increases mitochondrial motility (e.g., Armcx1 polypeptide or a vector comprising a nucleic acid sequence encoding Armcx1 polypeptide to thereby contact the site of injury.

The term "administering" to a subject includes dispensing, delivering or applying an active compound in a pharmaceutical formulation to a subject by any suitable route for delivery of the active compound to the desired location in the subject to thereby contact the desired portion(s) of the neuron(s), (e.g., the injury, the injured neuron, or the site of desired outgrowth of the neuron). This includes, without limitation, delivery by either the parenteral or oral route, intramuscular injection, subcutaneous/intradermal injection, intravenous injection, buccal administration, transdermal delivery and administration by the rectal, colonic, vaginal, intranasal or respiratory tract route, intraocular, ocular. Another form of administration suitable for treatment of spinal cord injury is injection into the spinal column or spinal canal. In one embodiment, the agent(s) is contacted in vivo by introduction into the central nervous system of a subject, e.g., into the cerebrospinal fluid of the subject. In certain aspects of the invention, the agent(s) is introduced intrathecally, e.g., into a cerebral ventricle, the lumbar area, or the cisterna magna. In another aspect, the agent(s) is introduced intraocullarly, to thereby contact retinal ganglion cells or the optic nerve. Modes of administration are described in U.S. Pat. No. 7,238,529.

In one embodiment, administration occurs following neuronal injury in the subject, not prior to or at the time of neuronal injury. In another embodiment of the invention, the agent(s) formulation is administered into a subject intrathecally. As used herein, the term "intrathecal administration" is intended to include delivering an inhibitor(s) formulation directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of an agent(s) to any of the above mentioned sites can be achieved by direct injection of the agent(s) formulation or by the use of infusion pumps. For injection, the agent(s) formulation of the invention can be formulated in liquid solutions, preferably in physiologically compatible buffers such as Hank's solution or Ringer's solution. In addition, the inhibitor(s) formulation may be formulated in solid form and re-dissolved or suspended immediately prior to use. Lyophilized forms are also included. The injection can be, for example, in the form of a bolus injection or continuous infusion (e.g., using infusion pumps) of the agent(s) formulation.

In one embodiment of the methods and compositions disclosed herein, said agent(s) formulation is administered by lateral cerebroventricular injection into the brain of a subject in the inclusive period from the time of the injury to a time determined by the skilled practitioner (e.g., 100 hours). The injection can be made, for example, through a burr hole made in the subject's skull. In another embodiment, said encapsulated therapeutic agent is administered through a surgically inserted shunt into the cerebral ventricle of a subject in the inclusive period from the time of the injury to a time determined by the skilled practitioner (e.g., 100 hours thereafter). For example, the injection can be made into the lateral ventricles, which are larger, even though injection into the third and fourth smaller ventricles can also be made.

In yet another embodiment, said agent(s) formulation is administered by injection into the cisterna magna, or lumbar area of a subject in the inclusive period from the time of the injury to a time determined by the skilled practitioner (e.g., 100 hours thereafter). Administration can be continuous, or can be by repeated doses. In one embodiment, the repeated doses are formulated so that an effective amount of the inhibitors is continually present at the injury site.

Viral and non-viral-based gene transfer methods can be used to introduce nucleic acids encoding Armcx1 polypeptides to cells or target tissues of the subject. Such methods can be used to administer nucleic acids encoding Armcx1 polypeptides to cells in vitro. Alternatively, or in addition, such polynucleotides can be administered for in vivo or ex vivo gene therapy uses. Non-viral vector delivery systems include DNA plasmids, naked nucleic acid, and nucleic acid complexed with, for example, a liposome or other delivery vehicle. Viral vector delivery systems include both DNA and RNA viruses, and can have either episomal or integrated genomes after delivery to the cell. Gene therapy procedures are described, for example, in Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Böhm (eds) (1995); and Yu et al., Gene Therapy 1:13-26 (1994).

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described, e.g., in U.S. Pat. Nos. 5,049,386, 4,946,787; and 4,897,355, and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

RNA or DNA viral based systems can be used to target the delivery of polynucleotides carried by the virus to specific cells in the body and deliver the polynucleotides to the nucleus. Viral vectors can be administered directly to patients (in vivo) or they can be used to transfect cells in vitro. In some cases, the transfected cells are administered to patients (ex vivo). Conventional viral based systems for the delivery of polypeptides of the invention could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene, and high transduction efficiencies.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any of the following numbered paragraphs:
1. A method for promoting survival of, or axon regeneration in an injured mature central nervous system (CNS) neuron comprising contacting the neuron with an effective amount of an agent capable of increasing mitochondrial motility in the injured neuron, thereby promoting survival of, or axon regeneration in the injured neuron.
2. The method of paragraph 1, further comprising detecting the resultant promotion of the survival of, or axon regeneration in the injured neuron in the subject.
3. The method of any one of paragraphs 1-2, wherein the injured neuron results from traumatic injury, traumatic brain injury, optic nerve injury, acute spinal cord injury, stroke, restorative CNS surgery or CNS degeneration.
4. The method of any one of paragraphs 1-3, wherein the injured neuron is a sensory neuron.
5. The method of any one of paragraphs 1-4, wherein the injured neuron is in the spinal cord.
6. The method of any one of paragraphs 1-4, wherein the injured neuron is in the optic nerve.
7. The method of any one of paragraphs 1-6, wherein the agent is administered intravenously, intracortically, intracerebrally, intrathecally, intranasally, ocularly or locally at the injured neuron.
8. The method of any one of paragraphs 1-7, wherein the agent is Armcx1 polypeptide.
9. The method of paragraph 8, wherein the Armcx1 polypeptide is recombinant.
10. The method of any one of paragraphs 8-9, wherein the Armxc1 polypeptide comprises a carrier peptide or lipophilic molecular group and/or is encapsulated in a liposome or a nanoparticle.
11. The method of any one of paragraphs 1-7, wherein the agent is a vector comprising a nucleic acid sequence that encodes a Armcx1 polypeptide.
12. The method of paragraph 11, wherein the vector is a viral vector or non-viral vector.
13. The method of paragraph 12, wherein the viral vector is selected from the group consisting of retrovirus, lentivirus, adenovirus, herpesvirus, poxvirus, alpha virus, vaccinia virus, and adeno-associated viruses.
14. The method of paragraph 12, wherein the non-viral vector is selected from the group consisting of a nanoparticle, a cationic lipid, a cationic polymer, a metallic nanoparticle, a nanorod, a liposome, microbubbles, a cell penetrating peptide and a liposphere.
15. The method of any one of paragraphs 8-14, wherein the Armcx1 polypeptide is of human origin.
16. The method of any one of paragraphs 8-15, wherein the Armcx1 polypeptide comprises the sequence of SEQ ID NO:1.
17. The method of any one of paragraphs 8-16, wherein the Armcx1 polypeptide has at least 95% amino acid sequence identity to SEQ ID NO:1 and retains at least 80% of the biological activity of human Armcx1 of SEQ ID NO:1.
18. The method of any one of paragraphs 2-17, wherein the detecting step is effected by an indirect assay of axon regeneration.
19. The method of any one of paragraphs 2-17, wherein the detecting step is effected by a direct assay of axon regeneration.
20. The method of any one of paragraphs 1-19, further comprising an antecedent step of determining that the neuron is injured, and has axotomy-induced stress.
21. The method of any one of paragraphs 1-20, further comprising contacting the injured neuron with a PTEN inhibitor, inhibitor of suppressor of cytokine signaling 3 (SOCS3), inosine, oncomodulin, BNDF, NGF, CNTF, or combinations thereof.

22. The method of paragraph 21, wherein the inhibitor of SOCS3 comprises a SOCS3 specific hpRNA or siRNA.
23. The method of paragraph 21, wherein the PTEN inhibitor is,
   (a) potassium bisperoxo(bipyridine)oxovanadate (V) (bpV (bipy));
   (b) dipotassium bisperoxo(5-hydroxypyridine-2-carboxyl) oxovanadate (V) (bpV(HOpic));
   (c) potassium bisperoxo(1,10-phenanthroline)oxovanadate (V), (bpV(phen)); or
   (d) dipotassium bisperoxo(picolinato)oxovanadate (V), (bpV(pic)).
24. The method of any one of paragraphs 1-23, wherein the neuron is human.
25. A method of treating a subject for neuronal injury, comprising:
   administering to the subject an agent that increases mitochondrial motility in injured neurons, wherein the administering results in contacting the injured neurons of the subject with the agent in an amount sufficient to promote survival of, or axon regeneration in the injured neurons, such that the subject is treated.
26. The method of paragraph 25, wherein the agent is administered intravenously, intracortically, intracerebrally, intrathecally, intranasally, ocularly or locally at the site of neuronal injury.
27. The method of any one of paragraphs 1-26, wherein the neuronal injury results from a traumatic injury, traumatic brain injury, optic nerve injury, acute spinal cord injury, stroke, restorative CNS surgery or CNS degeneration.
28. The method of paragraph 27, wherein the neuronal injury results from restorative CNS injury and wherein the agent is administered prior to, during or following restorative CNS surgery.
29. The method of any one of paragraphs 25-28, wherein the agent is Armcx1 polypeptide.
30. The method of paragraph 29, wherein the Armcx1 polypeptide is recombinant.
31. The method of any one of paragraphs 28-30, wherein the Armxc1 polypeptide comprises a carrier peptide or lipophilic molecular group and/or is encapsulated in a liposome or a nanoparticle.
32. The method of any one of paragraphs 25-28, wherein the agent is a vector comprising a nucleic acid sequence that encodes a Armcx1 polypeptide.
33. The method of paragraph 32, wherein the vector is a viral vector or non-viral vector.
34. The method of paragraph 33, wherein the viral vector is selected from the group consisting of retrovirus, lentivirus, adenovirus, herpesvirus, poxvirus, alpha virus, vaccinia virus, and adeno-associated viruses.
35. The method of paragraph 33, wherein the non-viral vector is selected from the group consisting of a nanoparticle, a cationic lipid, a cationic polymer, a metallic nanoparticle, a nanorod, a liposome, microbubbles, a cell penetrating peptide and a liposphere.
36. The method of any one of paragraphs 29-35, wherein the Armcx1 polypeptide is of human origin.
37. The method of any one of paragraphs 29-36, wherein the Armcx1 polypeptide comprises the sequence of SEQ ID NO:1.
38. The method of any one of paragraphs 29-37, wherein the Armcx1 polypeptide has at least 95% amino acid sequence identity to SEQ ID NO:1 and retains at least 80% of the biological activity of human Armcx1 of SEQ ID NO:1.
39. A method of treating a subject for a disease or disorder characterized by neuronal death or diminished potential for axonal growth, comprising administering to the subject an agent that increases mitochondrial motility, in an amount sufficient to promote survival of, or axonal growth in neurons, such that the subject is treated.
40. The method of paragraph 39, wherein the disorder is selected from group comprising of glaucoma, stroke, head trauma, spinal injury, optic injury, ischemia, hypoxia, neurodegenerative disease, multiple sclerosis, infectious disease, cancer, and autoimmune disease.
41. The method of paragraph 39-40, wherein the agent is Armcx1 polypeptide or a vector comprising a nucleic acid sequence encoding an Armcx1 polypeptide.
42. A method for promoting survival of, or axon regeneration in an injured mature central nervous system neuron in a subject determined to have a neuronal injury, the method comprising, administering to the subject Armcx1 polypeptide or an analog thereof in an amount sufficient to promote survival of, or axon regeneration of the injured neuron.
43. A device for promoting survival of, or axon regeneration in an injured mature central nervous system (CNS) neuron comprising a therapeutically effective amount of an agent that increases mitochondrial motility in the neuron, and wherein the device locally releases the agent into the CNS for promoting survival of, or axon regeneration in an injured mature central system (CNS) neuron.
44. The device of paragraph 43, comprising a CNS-implantable solid or semi-solid device selected from a biodegradable matrix, fiber, pump, stent, adsorbable gelatin osmotic pump or indwelling catheter.
45. A pharmaceutical composition comprising an effective amount of Armcx1 polypeptide or a vector comprising a nucleic acid sequence encoding the Armcx1 polypeptide and a pharmaceutically acceptable carrier, for use in promoting survival of, or regeneration of axon in injured neurons.
46. The pharmaceutical composition of paragraph 45, wherein the Armcx1 polypeptide is of human origin.
47. The pharmaceutical composition of any one of paragraphs 45-46, wherein the Armcx1 polypeptide comprises the sequence of SEQ ID NO:1.
48. The pharmaceutical composition of any one of paragraphs 45-47, wherein the Armcx1 polypeptide has at least 95% amino acid sequence identity to SEQ ID NO:1 and retains at least 80% of the biological activity of human Armcx1 of SEQ ID NO:1.
49. The pharmaceutical composition of any one of paragraphs 45-48, wherein the Armcx1 polypeptide is fused to a carrier polypeptide.
50. The pharmaceutical composition of any one of paragraphs 45-49, wherein the vector is a viral or non-viral vector.
51. The pharmaceutical composition of paragraph 50, wherein the viral vector is selected from the group consisting of retrovirus, lentivirus, adenovirus, herpesvirus, poxvirus, alpha virus, vaccinia virus, and adeno-associated viruses.
52. The pharmaceutical composition of paragraph 50, wherein the non-viral vector is selected from the group consisting of a nanoparticle, a cationic lipid, a cationic polymer, a metallic nanoparticle, a nanorod, a liposome, microbubbles, a cell penetrating peptide and a liposphere.
53. The pharmaceutical composition of any one of paragraphs 45-52, wherein the Armcx1 polypeptide or the vector comprising a nucleic acid sequence encoding the Armcx1 polypeptide is formulated with a lipophilic molecular group and/or encapsulated in a liposome or a nanoparticle.
54. The pharmaceutical composition of any one of paragraphs 45-53, formulated for administration to the brain, spinal cord, or optical nerve.
55. The pharmaceutical composition of any one of paragraphs 45-54, wherein the composition is formulated for administration via intracerebroventricular, intranasal, intracranial, intracelial, intracerebellar, or intrathecal administration route.
56. The pharmaceutical composition of any one of paragraphs 45-55, wherein the composition is contained in a delivery device selected from the group consisting of a syringe, a blunt tip syringe, a catheter, an inhaler, a nebulizer, a nasal spray pump, a nasal irrigation pump or nasal lavage pump, and an implantable pump.
57. A pharmaceutical composition comprising an agent that increases mitochondrial motility in injured neuron and a pharmaceutically acceptable carrier, for use in promoting survival of, or regeneration of axon in injured neurons.
58. The pharmaceutical composition of paragraph 57, wherein the agent is Armcx1 polypeptide or a vector comprising a nucleic acid sequence encoding the Armcx1 polypeptide.
59. A pharmaceutical composition formulated for ocular administration to a subject in need thereof, comprising an effective amount of Armcx1 polypeptide or a vector comprising nucleic acid sequence encoding the Armcx1 polypeptide, wherein the effective amount is the amount required for promoting survival of, or axon regeneration of axon in an injured mature CNS neuron in the subject.
60. A method for identifying an agent effective in promoting survival of, or axon regeneration in neurons after injury, the method comprising:
(a) contacting a neuron with a candidate agent;
(b) determining expression level of Armcx1 in the neurons from step (a); and
(c) identifying the candidate agent as effective if the expression level of Armcx1 is increased relative to a reference level upon the contact of the neuron with the candidate agent; or identifying the candidate agent as ineffective if the expression level of Armcx1 is not changed relative to a reference level upon the contact of the neuron with the candidate agent.
61. The method of paragraph 59, wherein the reference level is expression level of Armcx1 in neurons prior to contact with the candidate agent.
62. The method of any one of paragraphs 59-60, wherein the contacting is in vitro or in vivo.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the invention. Further, all patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology described herein is further illustrated by the following examples which in no way should be construed as being further limiting.

Experimental Procedure

Mouse Strains. $PTEN^{f/f}$; $SOCS3^{f/f}$ mice were obtained by breeding $PTEN^{f/f}$ (Park et al., 2008) and $SOCS3^{f/f}$ (Smith et al., 2009). Kcng4-cre; Thy1-stop-YFP line was a kind gift from Josh Sanes laboratory (Duan et al., 2015). For Bcl-2 experiments, because of mouse strain availability we used the Bcl-2/$PTEN^{f/f}$/$SOCS3^{f/f}$ line (Bei et al. 2016). Without expressing the Cre recombinase this line show no axon regeneration ((Bei et al. 2016) and FIG. S4D) and is considered as base line controls. Throughout all paper dKO conditions used as a model of high regeneration refers to $PTEN^{f/f}$; $SOCS3^{f/f}$ mice+AAV Cre+AAV CNTF (Sun et al., 2012). CNTF is used to potentiate the effect of SOCS3 deletion alone (Smith et al., 2009).

Constructs. The Armcx1-HA, Armcx1ΔTM-HA, PLAP and Armcx1F2AGFP vectors were generated from the pAAV-MCS constructs (Stratagene). For shRNA Armcx1 constructs, two targeting sequences against Armcx1 (shRNA2; targeting sequence GAGAGGCAAACCTCAAGATGACTC and shRNA5; TCAGTCAAGTGTGTGACGATACC were cloned into pAAV-Armcx1-2in-shRNA-mCherry vector from ViGene Biosciences. The construct was generated by ViGene Sciences, Inc. Control shRNA Scramble construct was generated from the pAAV-U6-GFP (Cellbiolabs).

Retina Explant culture. P21 $PTEN^{f/f}$ mice were injected with AAV2-Cre and AAV2-PLAP (placental phosphatase alkaline) as control, AAV2-Armcx1HA or AAV2-Armcx1HAΔTM. 2 weeks after, retinas were dissected out in Hibernate-A (Brain Bits). Retina explants were then plated onto Poly-L-Lysin (Sigma) and Laminin (Sigma) coated glass bottom dishes (MatTek) in Neurobasal-A (Life Technology) supplemented with B-27 (Life Technology), L-Glutamine (Life Technology) and Penicillin/Streptomycin (Life Technology). To evaluate axonal outgrowth, explants were fixed in PFA 4%/Sucrose 1,5% in PBS after 2 weeks and labeled with primary antibody anti-Tuj1 (Covance Research Products Inc Cat #MMS-435P, RRID: AB_2313773 or Covance Research Products Inc Cat #MRB-435P-100, RRID:AB_10175616), secondary antibody Alexa-488 (1/400-Life Technology). For live imaging experiments, explant were incubated with tetramethylrhodamine methyl ester (TMRM) (Life Technologies) as described in (Verburg and Hollenbeck, 2008).

In situ hybridization and Immunohistochemistry. Animals were perfused intracardially with PBS followed by paraformaldehyde (PFA-Sigma) 4% in PBS (w/v). After dissection, tissues were post fixed in PFA 4% in PBS overnight at 4° C. and then incubated in Sucrose (Sigma) 15% in PBS for 48 h at 4° C. Samples were embedded in Tissu-Tek and frozen at −80° C. Eyes were sectioned by cryostat at 20 um. In situ hybridization was performed following classical protocol as described in (Nawabi et al., 2010). For Immunohistochemistry of whole mount retina, retinas from perfused animals were washed in PBS and blocked in 96 wells plates with PBS-Triton 0.3%—BSA 2% during one hour. Antibodies against HA (Roche Cat #11867431001, RRID:AB_390919) and Tuj1 (Covance Research Products Inc Cat #MRB-435P-100, RRID: AB_10175616) were apply on retina in blocking buffer and apply on retina overnight at 4° C. After PBS wash, retinas were incubated for a minimum of 2 hours at room temperature with Alexa secondary antibodies, washed with PBS and mount with fluoromount (SouthernBiotech). Retinas cross sections for immunohistochemistry study of Armcx1 was prepared as described above. Immunohistochemistry using Armcx1 antibody (Abeam Cat #ab65144, RRID: AB_1141088) was performed using Tyramide Signal Amplification system (TSA, Perkin Elmer) following manufacturer protocol. Tuj1 positive RGCs (Covance Research Products Inc Cat #MMS-435P, RRID:AB_2313773) were determined positive for Armcx1 when signal intensity was minimum 60% above background.

Cortical neurons culture and transfection. Cortical neurons were isolated from E18 mouse embryo (Charles River). Briefly, cortices were chemically dissociated in papain solution (Worthington Biochemicals) for 10 mn at 37° C. followed by two wash in trypsin inhibition solution (Sigma T9253) and mechanical dissociation using P1000 plastic tip in plain Neurobasal medium (Life Technology). Dissection, dissociation and wash were done in HBSS (Gibco 1470-112) with 45% glucose and kynurenic acid (Sigma K3375) solution (HBSS, kyuneric acid 10 mM, 100 mM Hepes, 100 mM MgCl2). Cells were plated on poly-1-lysine hydrobromide (Sigma) coated 35 mm glass bottom dish (MatTek, (90'000 cells/wells). Neurons were cultured in Neurobasal medium (Life Technology) supplemented with B-27 (Life Technology), L-Glutamine (Life Technology) and Penicillin/Streptomycin (Life Technology). Half of the medium was replaced every other day. Plasmid DNA transfections were performed using Lipofectamin 2000 (Invitrogen) following manufacturer procedure. We used 0.3 µg of vector GFP, AAV-Armcx1F2AGFP, MitoDsred2 (Promega) and 0.5 µg of shRNA plasmids. To study mitochondrial and BDNF positive vesicles transport neurons were transfected at DIV 5. At DIV7 the culture medium was replaced by Hibernate E low fluorescence (BrainBites) to maintain cell viability in CO2− free conditions during live imaging. For neurites outgrowth experiments, neurons were transfected at DIV1.

Cortical Neurons Immunohistochemistry. For immunohistochemistry of cortical neurons, DIV 5-7 neurons were fixed with 4% PFA/1.5% Sucrose in PBS and immunostained using standard procedure (Glater et al., 2006). Briefly, fixed neurons in glass bottom dish were incubated for 5 mn in PBS-Triton 0.3% followed by 1 hour in blocking solution (NGS 10%, Triton 0.1% in PBS). Primary antibodies against HA (Roche Cat #11867431001, RRID:AB_390919), GFP (Abcam Cat #ab13970, RRID:AB_300798) or RFP (Abcam Cat #ab62341, RRID:AB_945213) were incubated overnight. After PBS wash, secondary anti-rat antibody (1/400, Life Technologies) was added for 1 hour. Cover slips were mounted using Fuoromount-G (SouthernBiotech).

Protein analyses and Co-immunoprecipitation. For Western blot analyzing of Armcx1 constructs, proteins were extracted from Lipofectamin transfected HEK cells (0.5 µg of DNA) and immunoblot was performed as described in (Cartoni et al., 2005) with minor modifications. Co-immunoprecipation was performed as described in (López-Doménech et al., 2012). Briefly, HEK cells were transfected with 2.5 µg of each plasmid. 3 days later, cells were lysed in lysis buffer (Tris-HCl pH: 7.5, NaCl 150 mM, MgCl2 1.5 mM, EDTA 5 mM Triton 1%, Glycerol 10% and protease inhibitor cocktail). Immunoprecipitation was performed using Dynabeads Protein G (Novex 10003D) and following manufacturer protocol including mixing beads with 20 µg of antibody (Roche Cat #11867431001, RRID:AB_390919) for 10 mn on wheels at room temperature and a 1 hour incubation at room temperature with the cell homogenate. For elution a wash buffer was used (TrisHCl pH: 8, NaCl 500 mM, EDTA 1 mM, EGTA 1 mM, Triton 1%, NP-40 0.5%).

Live imaging. Adult retina explants. Time-lapse movies were acquired on a PerkinElmer Spinning Disc confocal microscope equipped with a temperature-controlled chamber at 37° C. and with a 20× oil objective. Each frame was captured every 2 s. and 60 frames were acquired in total for each recording with laser power set to 30% for each channel to minimize damage. A portion of 80-120 µm of axon located 150 µm from the tip was selected for analysis. Volocity software (PerkinElmer) was used for live recording. For both the retina explant and the cortical neuron images, a custom-made Image J macro was used for kymograph based motility analysis as described in (Pekkurnaz et al., 2014). Image J raw data were extracted as excel spreadsheets (Microsoft Excel) and statistical analysis was performed with GraphPad Prism version 6.0 for Mac OS X (GraphPad Software, Inc., La Jolla, Calif., USA). E18 cortical neurons. Neurons were transferred into pre-warmed Hibernate medium without phenol red, which buffers CO2 (Brain Bits). Transfected axons were detected using the GFP channel. Single axons were imaged on an inverted Nikon Eclipse Ti-U microscope and 1 frame was captured every 2 s. 60 frames were acquired in total for each recording.

Mitochondrial transport analysis. From the kymograph generated by the live imaging files, mitochondrial transport was analyzed as in (Pekkurnaz et al., 2014). Briefly, mitochondria were defined as motile when the average of the instantaneous velocity was higher than 0.05 µm/s (Wang and Schwarz, 2009). Mitochondria whose velocity was equal or lower than this threshold were considered as stationary. The moving frequency was defined as the percentage of time each mitochondrion spent in motion during the time of the recording and was calculated by dividing the time spent in motion by the total recording time. Hence, the motile pool of mitochondria were the mitochondria with a moving frequency higher than 0. The moving frequency of the motile mitochondria was calculated by excluding the stationary mitochondria. The moving frequency of individual mitochondria was used for statistical analysis. For the percentage of mitochondria in motion per axons, statistics were done on the number of axons. The density of mitochondria in axons was calculated by counting the number of mitochondria on the first frame of the recording used for mitochondrial transport analysis normalized by the length of the axons.

Surgical procedures. All experiments procedures were performed in compliance with animal protocols approved by the IACUC at Boston Children's Hospital. For all procedures, mice were anaesthetized with ketamine and pyrazine.

Eye ointment containing atropine sulfate was applied to protect the cornea during surgery. Animals received Buprenorphine (0.05 mg/kg, Bedford lab) for 24 hours as post-operative analgesic. Surgical procedures were achieved as described in (Park et al., 2008). AAV virus injection: 1 uL of AAV2 viruses were injected into the right eye of the different mice lines. A glass micropipette was inserted to peripheral retina, behind or a serrate in a way to avoid damage to the lens. When two viruses were injected, viruses were mixed and injected at the same time. The following viruses were used: AAV2-Cre, AAV2-PLAP, AAV2-Armcx1HA, AAV2-Armcx1HAΔTM, AAV2-CNTF, AAV2-shRNA Scramble and AAV2-shRNA Armcx1. The titers of the viruses were comprised between $10^{12}$-$10^{13}$ gc/mL. Viruses were produced at the Boston Children's Hospital viral core. Optic nerve injury: Four weeks following AAV2 injection (5 weeks for AAV-shRNAs), the right optic nerve was exposed intraorbitally and crushed with forceps (Dumont #5 FST) for 5 seconds approximately 1 mm behind the eye ball. RGC anterograde labeling: 2-3 days before animals were euthanized, 1.5 ul of cholera toxin β subunit (CTB-2 ug/ul, in sterile PBS-Life Technologies) coupled with Alexa-555 (CTB-Alexa-555) was injected into the vitreous with Hamilton syringe (Hamilton) to label axons in optic nerve.

Axon regeneration imaging and quantification. Optic nerves cryo-sections of 14 μm thick were imaged with a 20× objective using a PerkinElmer Spinning Disc confocal microscope equipped with a motorized stage and Volocity software (Perkin Elmer). For each nerve section, Z-projected to maximum intensity stacked images were stitched together with a 20% of overlap between each image to generate a single picture of the whole optic nerve. Regenerating axons were quantified as described in (Park et al., 2008). For whole mount optic nerve imaging, the protocol described in (Pernet et al., 2013) was followed with minor modifications. Briefly, optic nerves from perfused mice were post-fixed overnight washed three times 10 mn in PBS and incubated at room temperature for 20 min in increasing concentration of ethanol (50%, 80%, 95%, 100%). Nerves were kept at 4° C. overnight in ethanol 100% with constant agitation. Nerves were then put in Hexan (Sigma) for 3 hours at room temperature on a shaker. The clearing was completed by replacing Hexan by a solution of Benzyl alcohol/Benzyl Benzoate (1:2). Nerves were stored in the dark at room temperature in this final solution. For imaging, we used PerkinElmer Spinning Disc confocal microscope equipped with 20× objective and a motorized stage and Volocity software (Perkin Elmer). The whole nerve was acquired using optical sections of 2 μm and stitched images of the Z stacks projections to maximum intensity.

RGC survival imaging and quantification. Whole mount retinas were immunostained with anti-Tuj1 antibody (Covance Research Products Inc Cat #MMS-435P, RRID: AB_2313773 or Covance Research Products Inc Cat #MRB-435P-100, RRID:AB_10175616). Because of the layering pattern of the retina with the RGCs layer sitting on the top of a whole mount preparation, Tuj1 staining efficiently labeled RGCs (Belin et al., 2015; Nawabi et al., 2015; Park et al., 2008; Smith et al., 2009). Pictures from 10 regions per retina were taken under an epifluorescence microscope (Nikon 80i-20× objective). Tuj1 positive RGCs were counted in intact and injured eye for each animal. The number of Tuj1 positive RGCs in intact eye of each animal was considered as 100% for this particular animal and was compared to its injured eye to quantify the survival.

Statistical Analysis. Statistical analysis was performed with GraphPad Prism v6.0. Normality tests were run to assess the distribution of the data to be statistically analyzed. Non normal distributions were analyzed using non-parametric test: Mann-Whitney U test was used to determine the significance of differences between two conditions and the Kruskal-Wallis nonparametric ANOVA test when multiple conditions were compared. Normal distributions were analyzed using parametric test: Student's t-test was used to determine the significance of differences between two conditions and the one-way ANOVA test with Tuckey's multiple comparison test unless otherwise specified. $p<0.05$ was considered significant. For box plot graph, whiskers represent the maximum and minimum of the distribution and the horizontal bar in the box the median. For bar plots, all data are shown as mean+/−SEM.

Results

Armcx1 Expression is Up-Regulated in RGCs with High Regenerative Capacity

Because of the essential role of mitochondria in axonal physiology, using a loss of function approach to determine how regulators of mitochondrial dynamics influence axon regeneration might be difficult to interpret. Instead, that neurons characterized by a high regenerative capacity after axonal injury were thought to constitute an ideal starting point to identify mitochondrial transport regulators involved in axon regeneration. In previous studies (Sun et al., 2012), gene expression profiles were compared in injured RGCs with poor regenerative ability (wild type mice) and with induced high regenerative ability, referred to in this paper as the dKO model (PTENf/f; SOCS3f/f mice with vitreous injection of AAVs expressing Cre (AAV-Cre) and CNTF (AAV-CNTF), CNTF being used to further elevate the Jak/STAT signaling after SOCS3 deletion, Smith et al., 2009; Sun et al., 2012). From these datasets, no genes that have previously been implicated in mitochondrial transport, such as Milton or Miro, were found to be differentially expressed in these neurons with different regenerative ability. However, Armcx1, a member of a cluster of genes in which a family member, Armcx3, had been implicated in regulating mitochondrial transport (López-Doménech et al., 2012), appeared to be highly expressed in injured RGCs with induced regenerative ability (Sun et al., 2012).

Figure 1B:
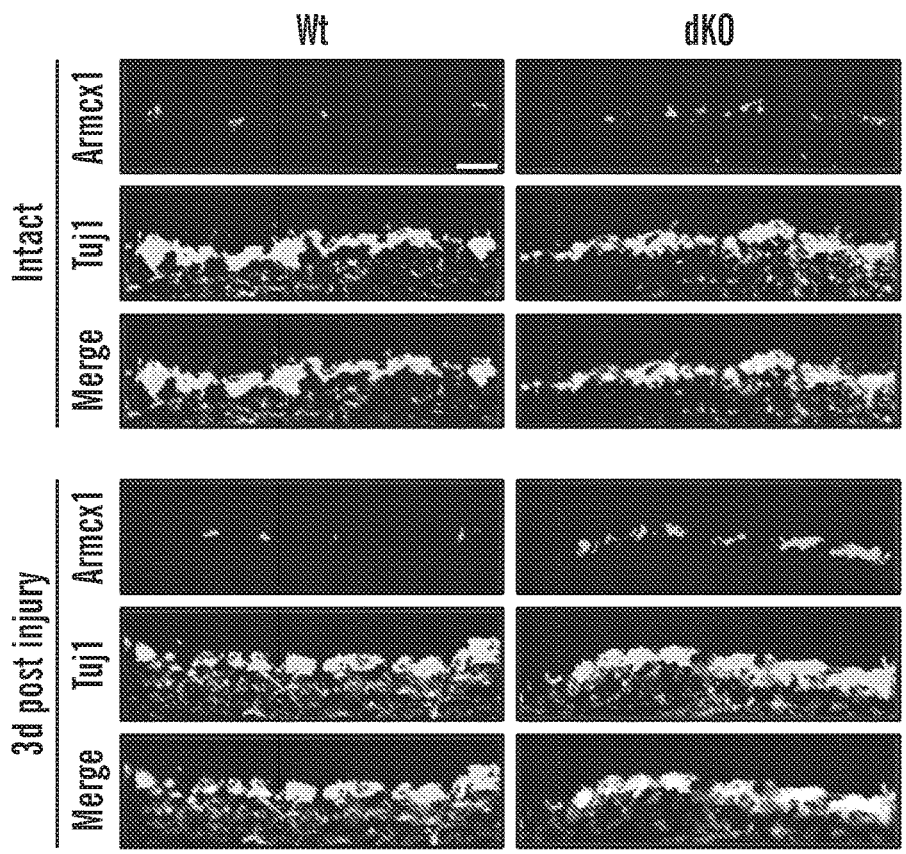
Figure 1C:
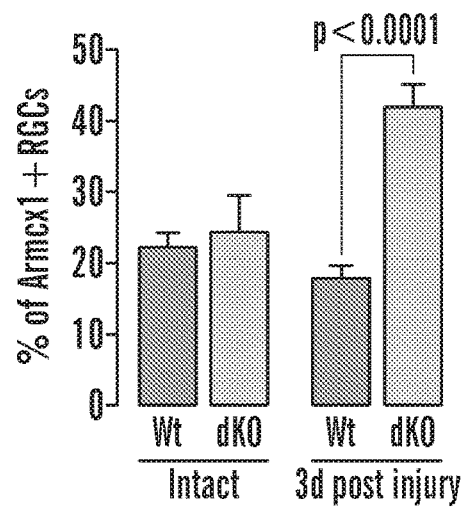
Figure 7A:
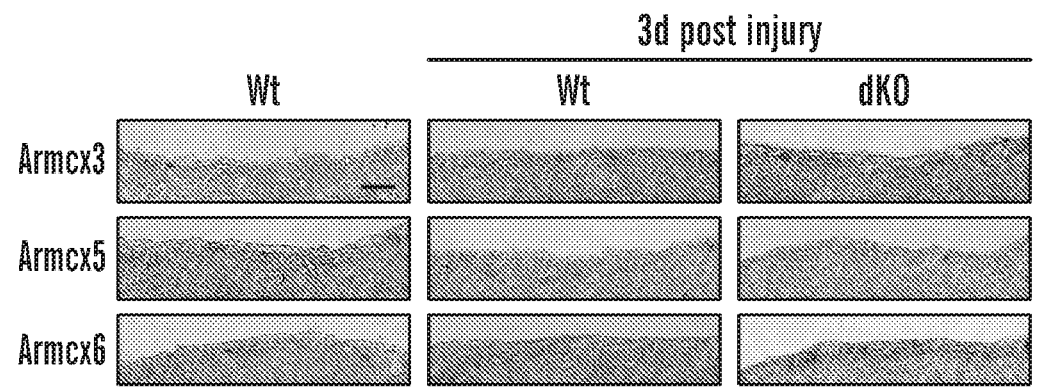
FIGS. 7A-7B show expression of Armcx1 homologues in high regeneration capacities RGCs and Armcx1 co-localization with mitochondria.

The expression of Armcx1 and its paralogs in RGCs was first verified by in situ hybridization. As shown in FIG. 1A, low levels of Armcx1 signal were detected in some RGCs of wild type mice, which were not affected by injury. In stark contrast, 3 days after injury, Armcx1 signal was significantly increased in the RGCs of the PTENf/f; SOCS3f/fmice with vitreous injection of AAV-Cre and CNTF (dKO), but not of PTENf/fmice with vitreous injection of AAV-Cre (PTEN−/−), consistent with the gene profiling results (Sun et al., 2012). In comparison, other Armcx members, including 3, 5, and 6, were expressed at low levels in all conditions (FIG. 7). The up-regulation of Armcx1 in dKO injured RGCs was further supported by immunohistochemistry (FIGS. 1B and 1C), which showed that RGCs positively stained with anti-Armcx1 increased approximately two-fold in the dKO after injury compared to other conditions (FIG. 1C; 40% in injured dKO compared to 20% in other conditions). Based on these results, Armcx1 was selected for further studies.

Figure 1D:
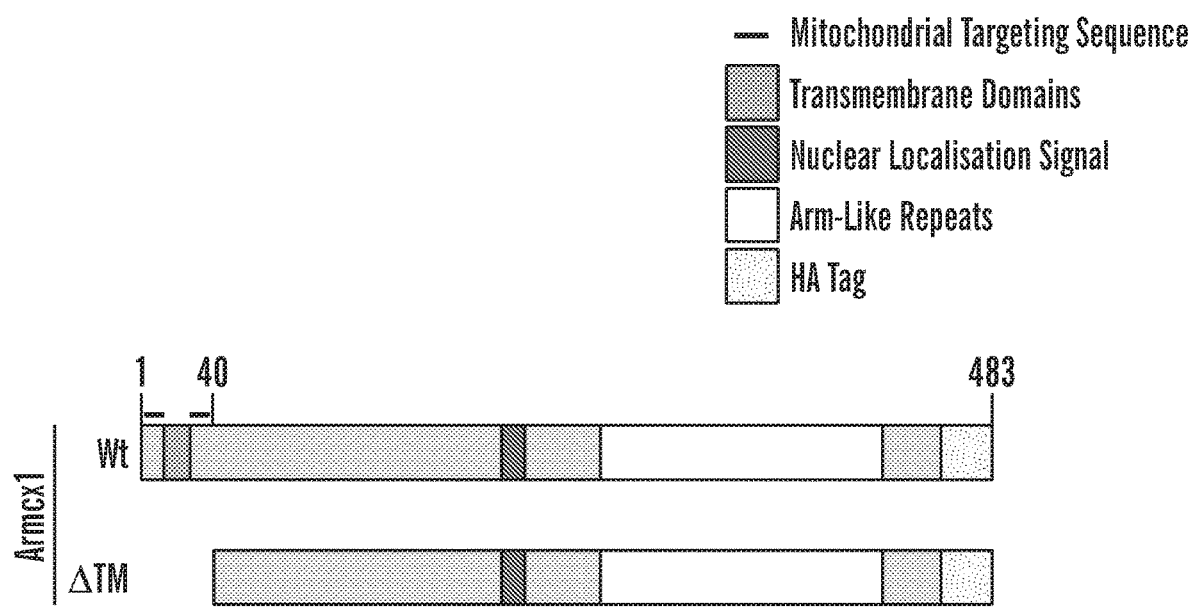
Figure 1E:
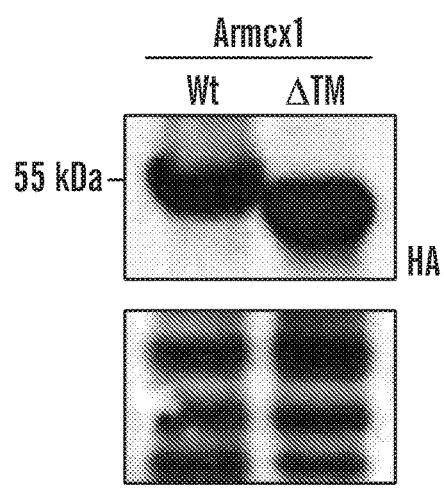
Figure 1G:
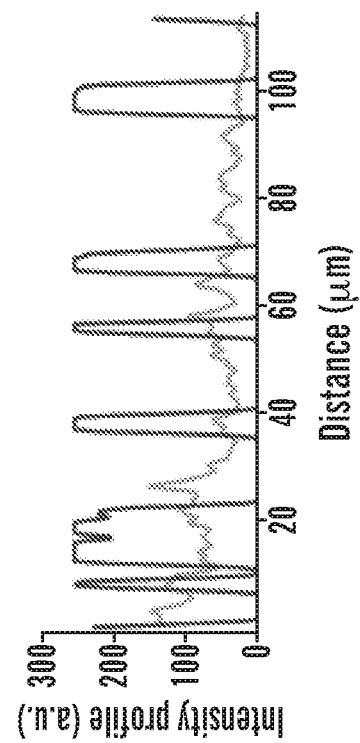
Figure 1G:
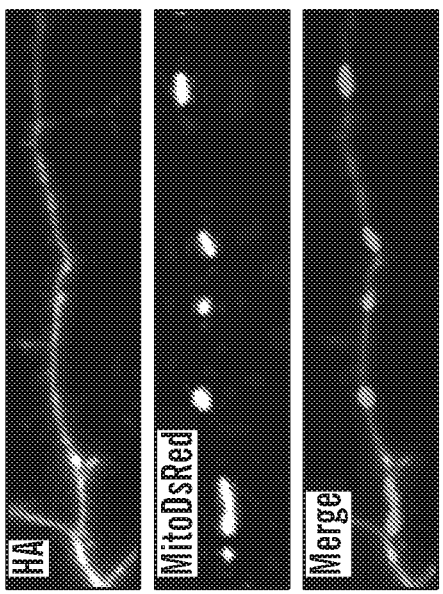
Figure 1F:
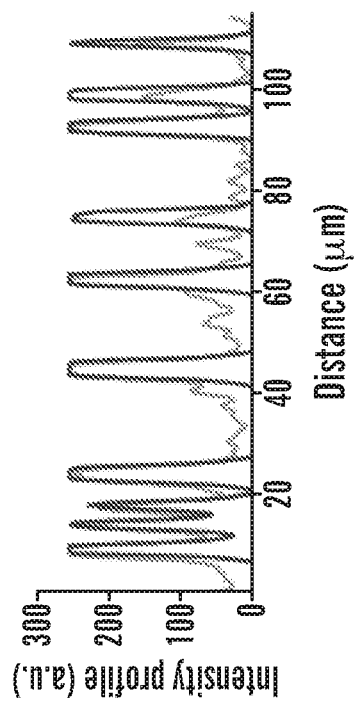
Figure 1F:
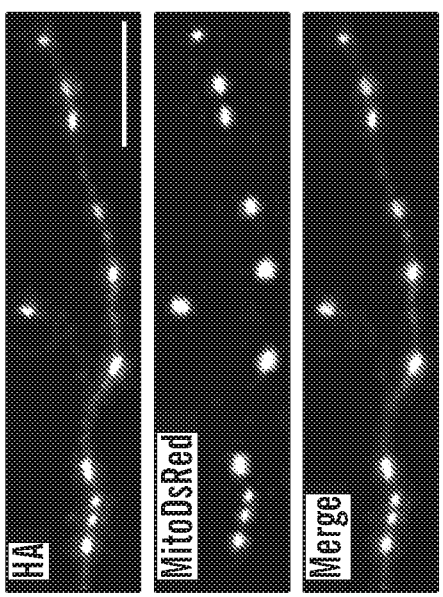
Figure 7B:
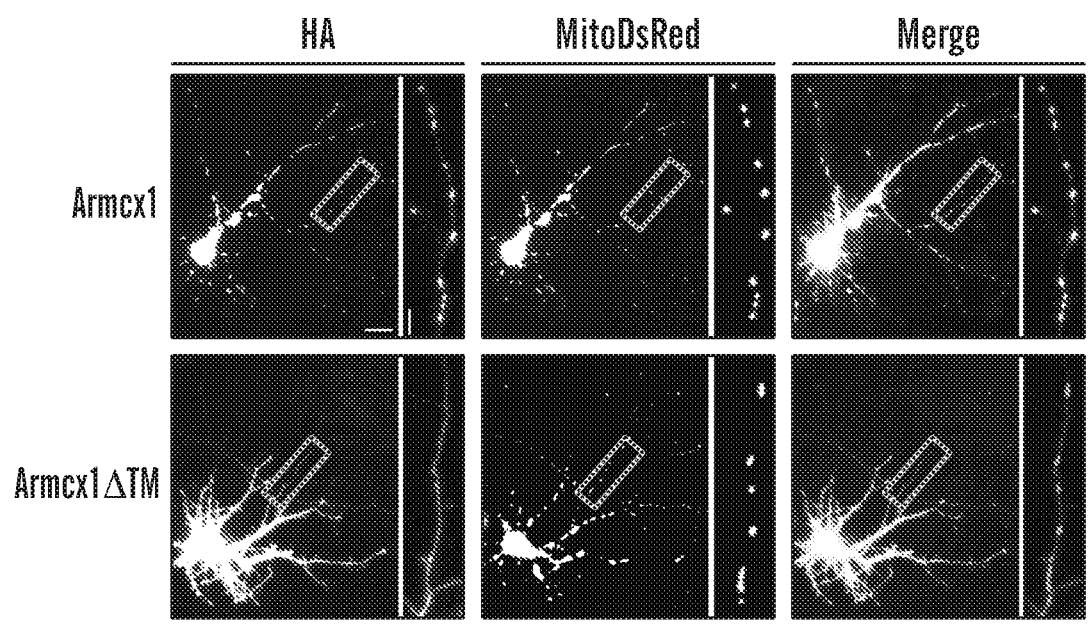

Armcx1 Localizes to Mitochondria and Interacts with Mitochondrial Transport Machinery Similar to other members of the Armcx cluster, Armcx1 has a putative mitochondrial outer membrane-targeting sequence flanking the trans-membrane (TM) domain (FIG. 1D) (Mou et al., 2009). A mutant of Armcx1 was designed that lacks its transmembrane domain, Armcx1ΔTM (FIGS. 1D and 1E) and assessed the localization of Armcx1 and Armcx1ΔTM by co-transfecting HA-tagged Armcx1 or Armcx1ΔTM with the mitochondrial marker MitoDsRed in mouse cortical neurons. The vast majority of Armcx1 protein was shown to be was targeted to mitochondria (FIG. 1F and FIG. 7B), while the absence of the TM domain of Armcx1 prevented its mitochondrial localization (FIG. 1G and FIG. 7B).

Figure 1H:
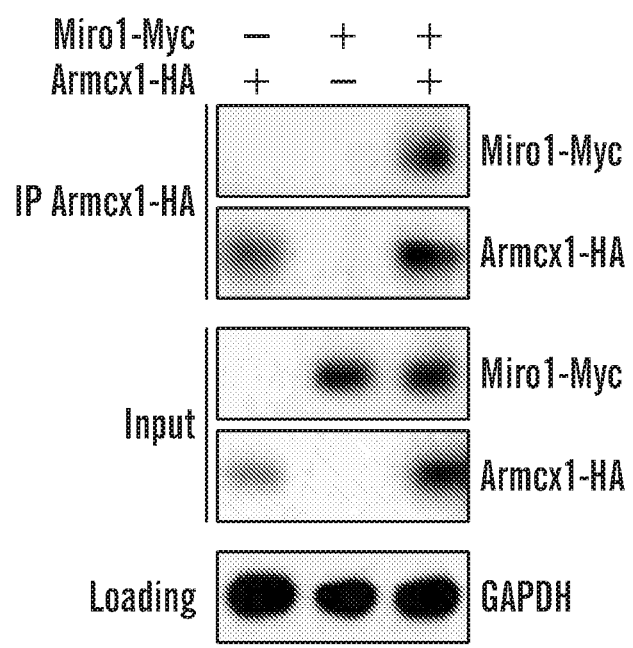

Armcx3 was recently shown to regulate mitochondrial transport by interacting with the mitochondria trafficking regulatory complex that connects mitochondria to the motor proteins (López-Doménech et al., 2012), but the role of Armcx1 is unknown. Co-immunoprecipitation using Armcx1-HA and Miro1-Myc showed that Armcx1 interacted with Miro1 (FIG. 1H), the protein linking mitochondria to the Trak1-Kinesin motor complex. Together, these results indicate that the mitochondria-localized Armcx1 protein is up-regulated in RGCs with induced regenerative ability and suggest that Armcx1 might be a candidate in regulating mitochondrial trafficking.

Armcx1 Overexpression Enhances Mitochondrial Transport in Adult RGC Axons

Figure 8B:
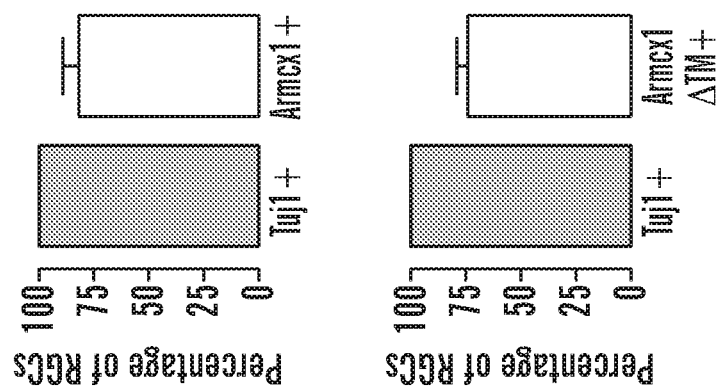
FIGS. 8A-8C shows characterization of AAV infected adult retina explants.
Figure 8A:
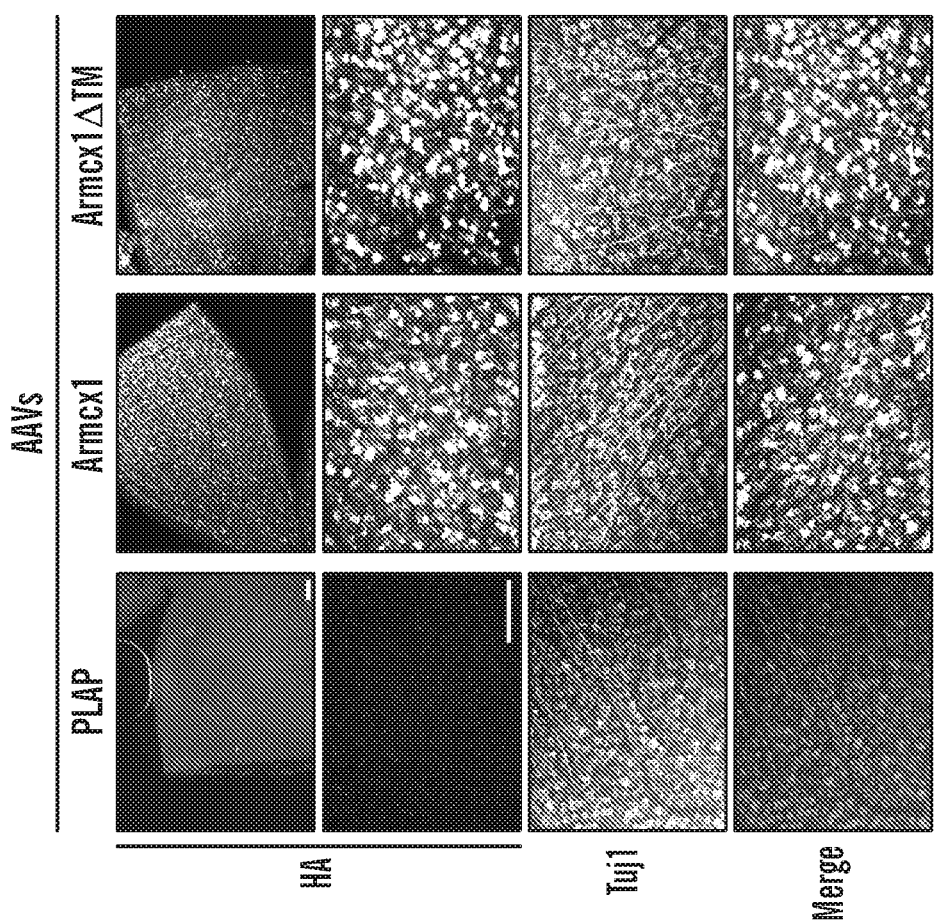
Figure 8D:
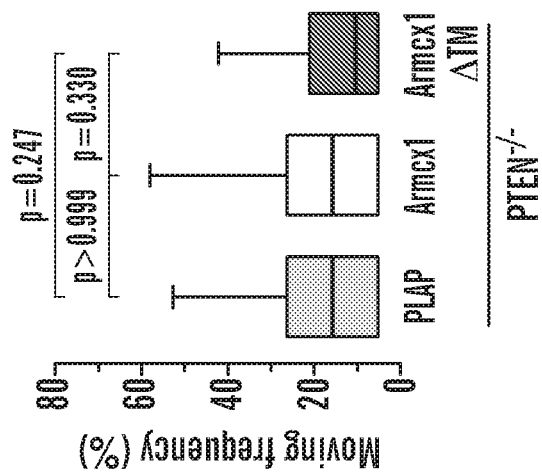
(FIG. 8D) Box plot showing the moving frequency of motile mitochondria in axons from adult retina explants of PTEN$^{f/f}$ mice injected with the indicated AAVs. The horizontal line indicates the median and the whiskers the maximum and minimum of the distribution. n=221-348 mitochondria from 11-16 axons, from 3 independent experiments. Kruskal-Wallis test with Dunn's multiple comparisons test.
Figure 8C:
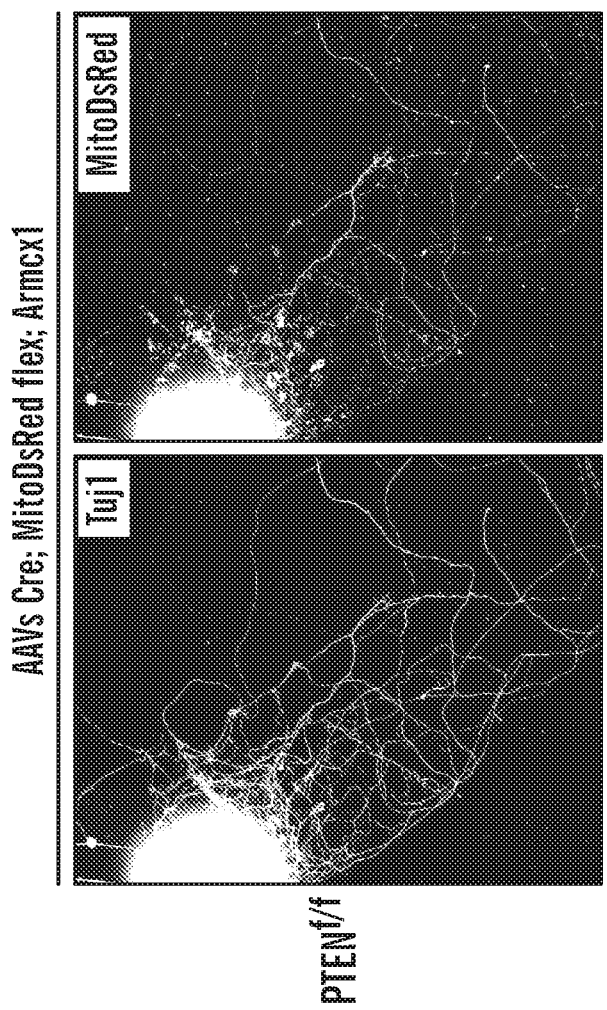

Axonal mitochondria are distributed in two pools: the motile pool, which can move bi-directionally and may pause before resuming movement, and the stationary pool, which is fixed in position typically for the observable duration of an experiment. The proportion of these two pools has been suggested as an important indicator of mitochondrial trafficking in axons (Schwarz, 2013). As a first step to assess the role of Armcx1 in the injury responses of adult RGCs, we examined whether enhancing the expression of Armcx1 would increase mitochondrial transport in adult RGC axons using retina explant cultures coupled with live imaging microscopy. Because of the poor neuronal survival and neurite growth of adult wild type retinal explants, we took advantage of the PTEN−/−mice whose RGCs showed better survival and axonal outgrowth in explant cultures (Nawabi et al., 2015). Since PTEN deletion alone did not significantly increase Armcx1 levels (FIG. 1A), this mutant is suitable for assessing the effects of overexpressed Armcx1. PTENf/f adult mice were intravitreally injected with AAV-Cre and AAVs expressing either full length Armcx1 or the Armcx1ΔTM mutant. As a control, AAV expressing placental alkaline phosphatase (PLAP), a well-established non-fluorescent and inert control for viral injection (Bei et al.; Belin et al., 2015; Nawabi et al., 2015), was used. Immunohistochemistry on whole mount retina confirmed the efficient infection of RGCs by AAVs encoding Armcx1 full length and mutant (FIGS. 8A and 8B). To confirm that multiple viral co-injections allowed efficient targeting of RGCs in explant culture, AAV expressing a mitochondrial protein (Cre-dependent MitoDsRed; AAV2-FLEX-MitoDsRed) was co-injected with AAV-Cre to the vitreous body of PTENf/fmice. This showed that the vast majority of the neurites growing out of the resultant explants were MitoDsRed positive (FIG. 8C).

The proportion of motile versus stationary mitochondria in axons overexpressing Armcx1 was assessed using live recording of mitochondrial transport. Unlike dissociated neuronal culture in which the morphology of mitochondria in the soma is used to confirm neuronal health prior to imaging, explant culture does not allow access to RGC cell bodies. To circumvent this issue, mitochondrial membrane potential was used as a marker of axonal health by labeling mitochondria with tetramethylrhodamine methyl ester (TMRM), a membrane potential dependent fluorescent dye (Trushina et al., 2012; Verburg and Hollenbeck, 2008; Zhang et al., 2016). Armcx1 overexpression induced a significant increase of the motile mitochondria pool compared to the PLAP control (FIGS. 2A and 2B). In contrast, the mutant Armcx1ΔTM failed to do so (FIGS. 2A, 2B), suggesting that the effect of Armcx1 on mitochondrial motility is dependent on its mitochondrial localization. Consistent with the increase of the motile mitochondrial pool, Armcx1 overexpression increased the moving frequency of the total pool of mitochondria, i.e. the fraction of time mitochondria in motion rather than paused (FIG. 2C). To further determine whether the overexpression of Armcx1 increased the transport of mitochondria from the motile pool, we specifically analyzed the moving frequency of this pool and did not observe any difference between control and Armcx1 overexpression (FIG. 8D). Since Armcx1 overexpression increased the proportion of motile mitochondria with no accompanying changes of mitochondrial density (FIG. 2D), Armcx1 was concluded to likely increase mitochondrial transport by recruiting stationary mitochondria into the motile pool.

Armcx1 Promotes Retinal Neurite Outgrowth

In addition to mitochondrial movement, the effects of Armcx1 on neurite outgrowth was also assessed from these retinal explants. Immunohistochemistry against the neuronal marker Tuj1 revealed that Armcx1 overexpression triggered a substantial increase in axons growing out of the explants (FIGS. 2E-2G) independent of their size (FIG. 2F). Detailed analysis showed that the Armcx1-induced axonal outgrowth was more evident at short distances (FIG. 2E lower panel and FIG. 2G). Consistent with the mitochondrial transport data, the overexpression of the non-mitochondrial Armcx1 mutant (Armcx1ΔTM) failed to reproduce the outgrowth phenotype observed with full length Armcx1 (FIGS. 2E-2G), suggesting a direct link between Armcx1 localization on mitochondria and enhanced axonal outgrowth.

Figure 9A:
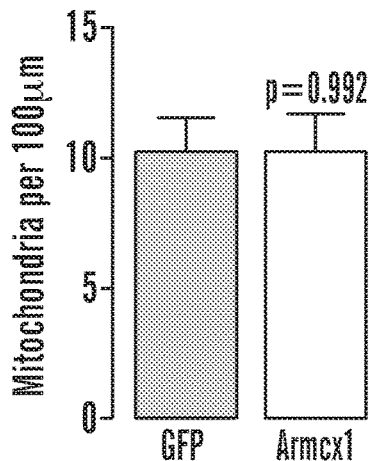
FIGS. 9A-9C shows Armcx1 overexpression does not affect mitochondrial density and transport of BDNF positive vesicles.
Figure 9B:
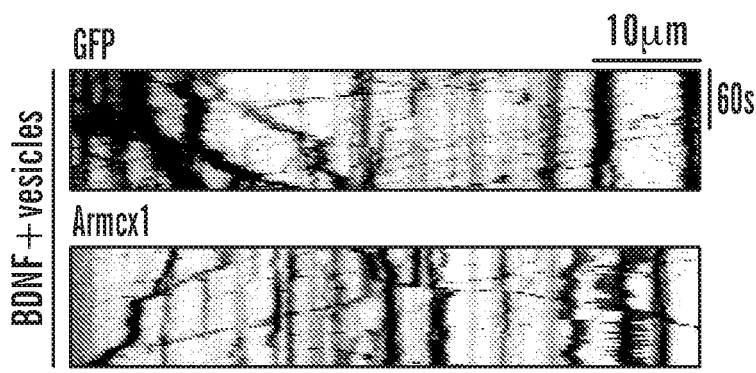
Figure 9C:
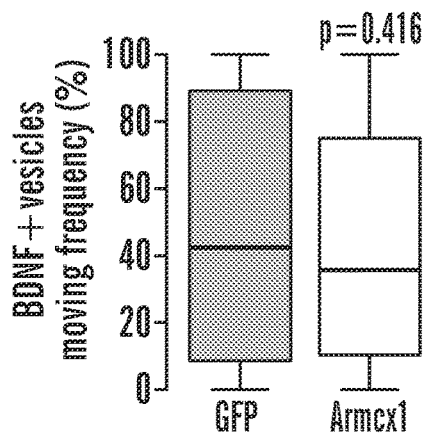

Armcx1 Regulates Mitochondrial Transport and Neurite Outgrowth in Embryonic Neurons In order to test whether Armcx1 overexpression has a general effect on mitochondrial transport and neurite outgrowth, similar analyses were performed as described above in cultured E18 cortical neurons, a well-established system for investigating mitochondrial trafficking (Pekkurnaz et al., 2014; Wang and Schwarz, 2009; Wang et al., 2011). Whether Armcx1 overexpression could alter the proportion of motile versus stationary mitochondria in these neurons was first addressed. The mitochondrial marker MitoDsRed was co-transfected with either Armcx1 or GFP as a control. Armcx1 expression was coupled with a GFP reporter linked by an F2A sequence allowing the identification of transfected neurons. Whereas in wild type axons around 50% of mitochondria were motile, Armcx1 overexpression significantly increased the percentage of motile mitochondria up to 80% (FIGS. 3A and 3B). Consistently, Armcx1 overexpression also significantly increased the moving frequency of mitochondria (FIG. 3C) with no effect on mitochondrial density (FIG. 9A). In contrast to its effect on mitochondria trafficking, overexpressing Armcx1 did not affect the transport of BDNF positive vesicles (FIGS. 9B and 9C), consistent with a specific localization of Armcx1 to mitochondria. In addition, Armcx1 overexpression significantly increased the average length of the longest neurites of embryonic cortical neurons (FIGS. 3D and 3E). These results together suggest that Armcx1 overexpression leads to similar effects on enhancing mitochondria movement and neurite growth in both adult RGC axons and embryonic cortical neurons.

Figures 4A, 4B:
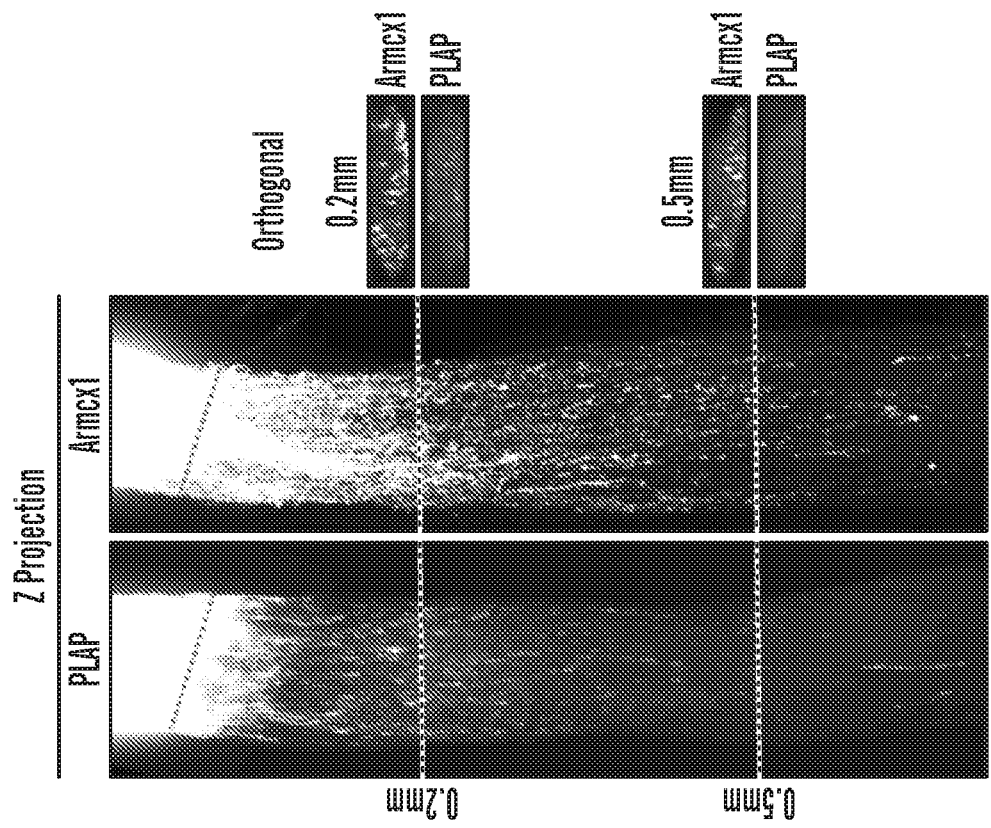
FIGS. 4A-4E shows Armcx1 promotes axonal regeneration and neuronal survival.
Figure 4C:
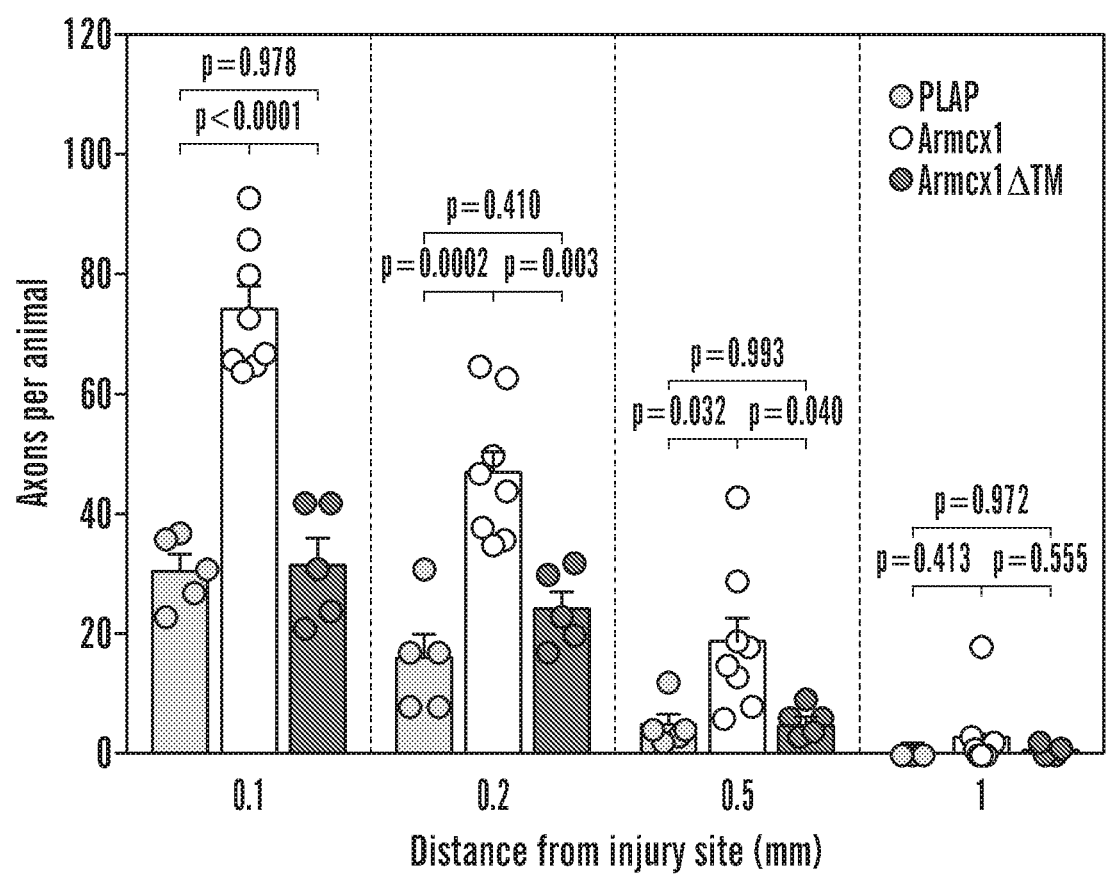
Figure 4D:
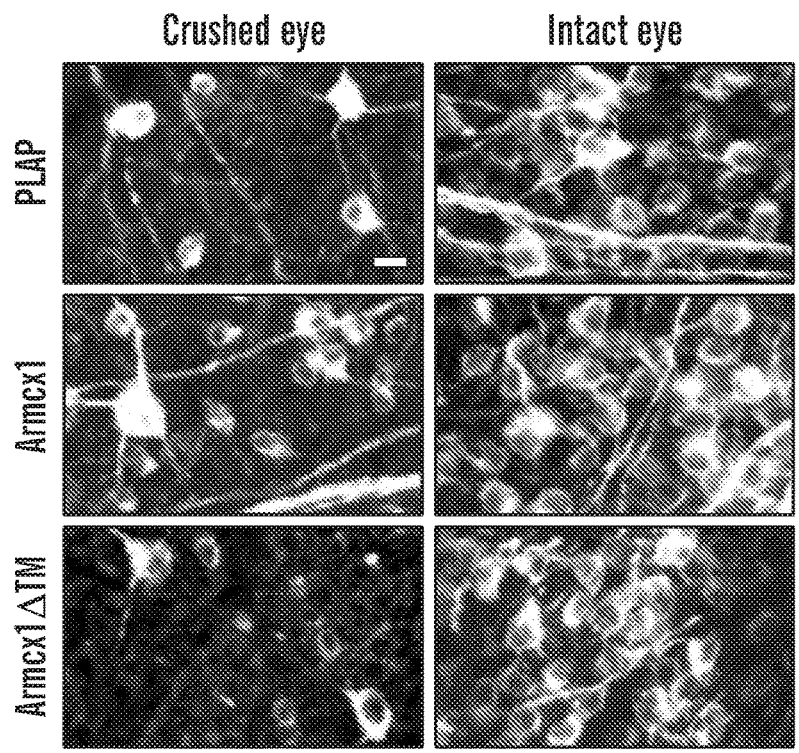
Figure 4E:
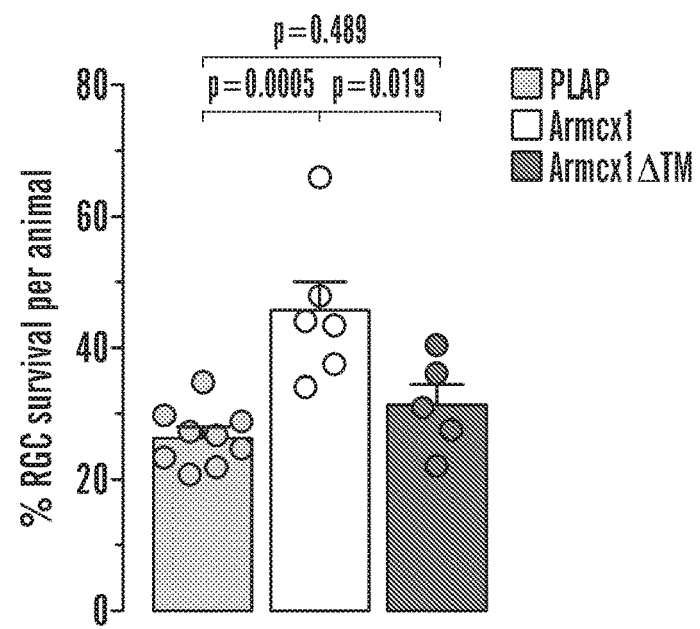

Armcx1 Promotes Neuronal Survival and Axon Regeneration after Optic Nerve Injury The above results suggest that Armcx1 might have a role in promoting neurite outgrowth. We hypothesized that this role could be important to promote axonal regeneration after an injury. To directly test this hypothesis, the effects of Armcx1 overexpression on axon regeneration and neuronal survival in adult RGCs was examined after an optic nerve crush injury. AAVs encoding Armcx1, Armcx1ΔTM or PLAP were injected into the vitreous body of adult wild type mice and optic nerve crush was performed one month after viral injection. 15 days after injury, the regenerating axons were labeled with the anterograde tracer CTB. Armcx1 overexpression induced a significantly higher number of regenerating axons in comparison to PLAP control (FIGS. 4A-4C). Consistent with in vitro data, this effect was dependent on Armcx1 mitochondrial localization since the overexpression of Armcx1ΔTM failed to recapitulate the enhanced regeneration (FIGS. 4A-4C). The effect of Armcx1 overexpression on the survival of RGCs (FIGS. 4D and 4E) was also analyzed. Consistent with previous studies (Belin et al., 2015; Nawabi et al., 2015; Park et al., 2008; Smith et al., 2009), about 25% of RGCs survived in the control group (FIGS. 4D and 4E). Strikingly, overexpressing Armcx1, but not the non-mitochondrial mutant Armcx1ΔTM, led to an increase of approximatively 45% of neuronal survival compared to the control group (FIGS. 4D and 4E), suggesting that Armcx1 may not only promote axon regeneration but also protect injured neurons from cell death.

Figure 10B:
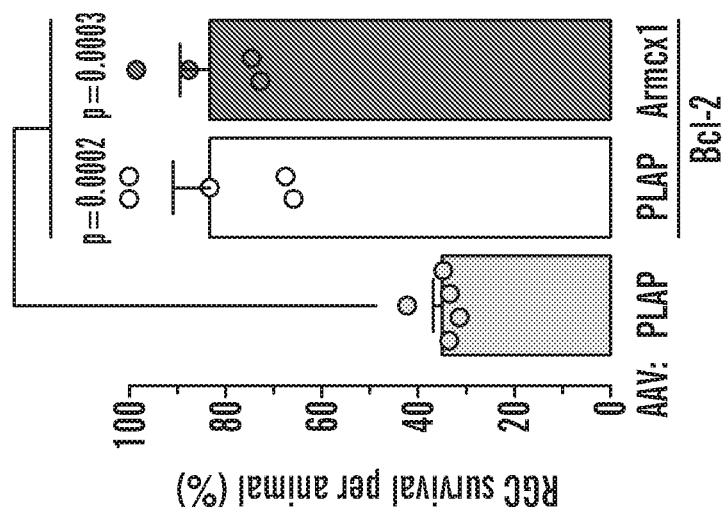
FIGS. 10A-10D show Armcx1 improve axonal regeneration independently of its survival effect.
Figure 10A:
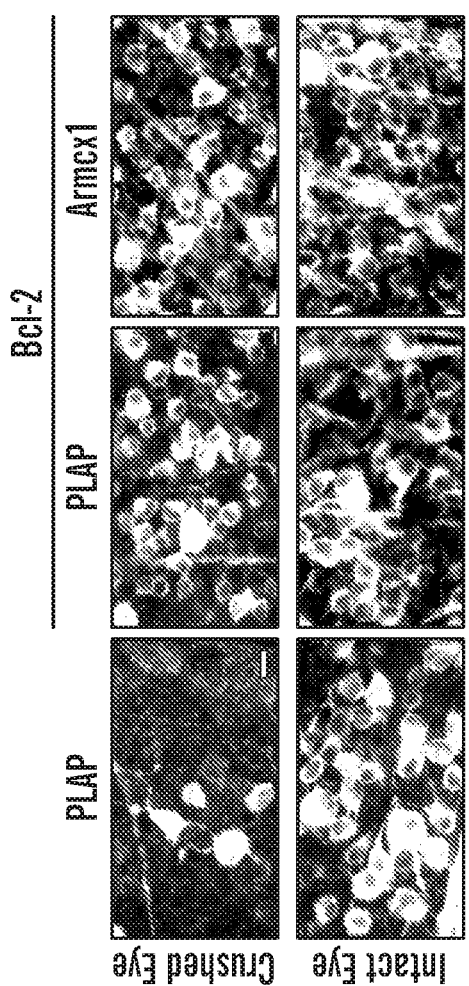
Figure 10D:
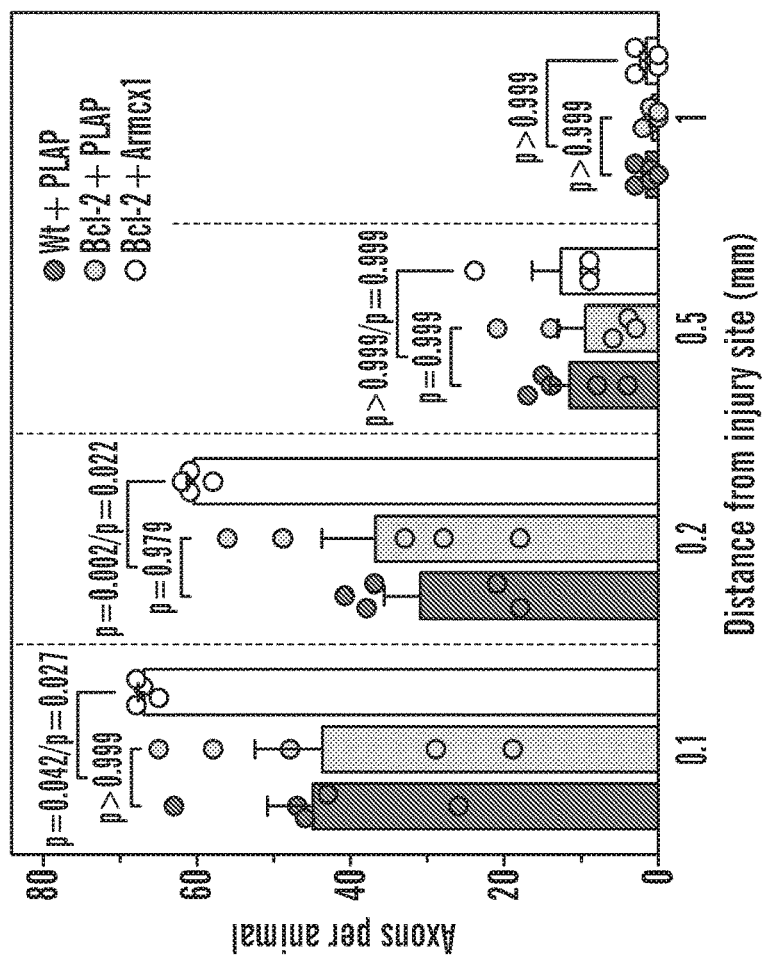
Figure 10C:
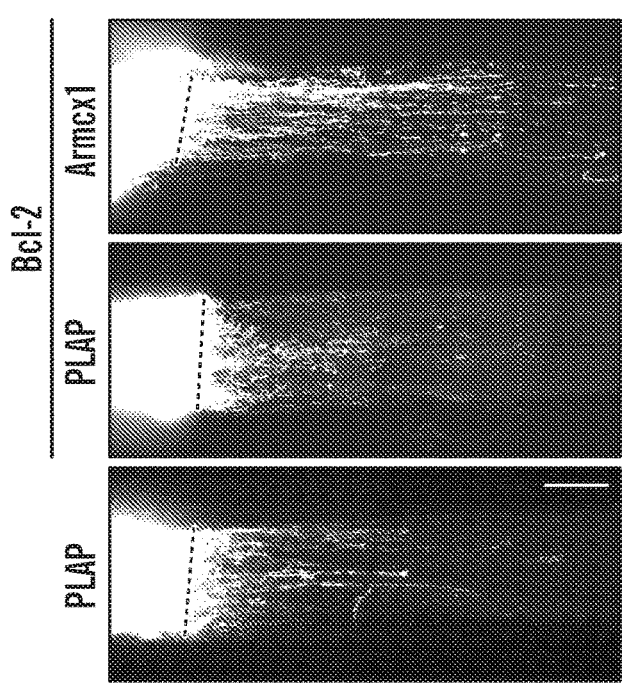

In principle, the observed regenerative effects of Armcx1 overexpression might reflect a direct effect of Armcx1 on axon regeneration or be merely secondary to increased neuronal survival. Several strategies such as p53 deletion (Park et al., 2008), manipulating ER stress pathways (Hu et al., 2012), and Apaf1-deleted mice are able to increase neuronal survival but not axon regeneration in the same optic nerve injury model, suggesting that axon regeneration requires an independent mechanism. To directly test this in the context of Armcx1, a transgenic mouse line was used in which Bcl-2 is overexpressed under a pan neuronal promoter (Martinou et al., 1994). Consistent with previous results using Bcl-2 transgenic mice (Bei et al.; Bonfanti et al., 1996; Goldberg et al., 2002), about 80% of RGCs survived but no significant increase in axon regeneration occurred 2 weeks after injury (FIG. 10). With Armcx1 overexpression, high neuronal survival remained at 15 days after injury in these mice (FIGS. 10A and 10B). Importantly, even with this high survival rate, Armcx1 overexpression improved axon regeneration of Bcl-2 mice (FIGS. 10C and 10D) but did not further enhance the extent of axon regeneration beyond what was observed by Armcx1 overexpression in the absence of Bcl-2 (FIGS. 10C and 10D compare to the results in FIGS. 4A-4C). Therefore, these findings substantiate the notion that, in addition to promoting neuronal survival, Armcx1 is also directly involved in regulating the process of axon regeneration after injury.

Armcx1 Potentiates the Regeneration of PTEN Deleted RGCs

Figure 5A:
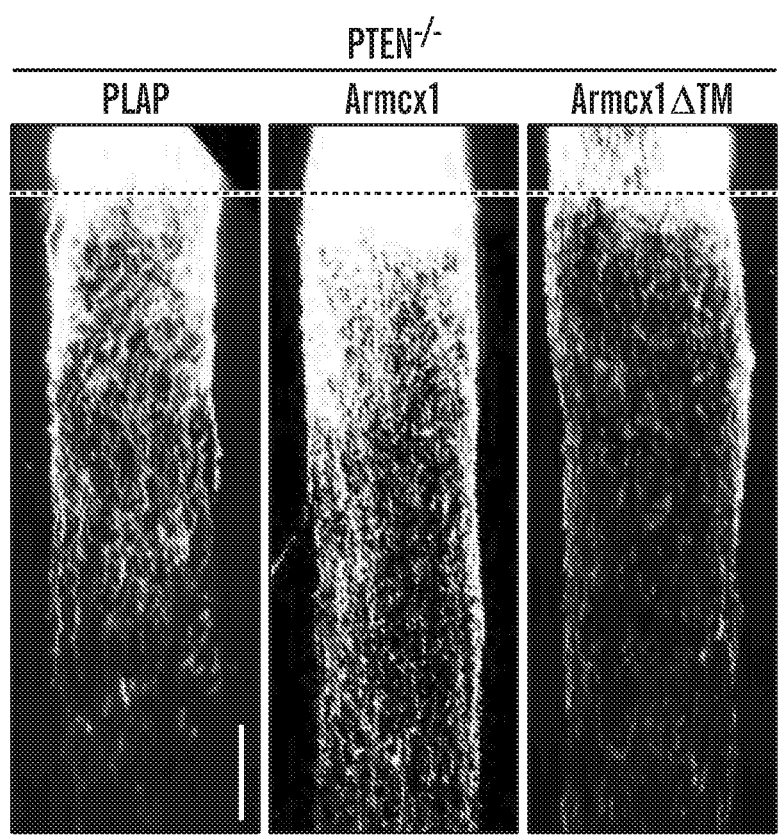
FIGS. 5A-5F show Armcx1 potentiates axonal regeneration of PTEN deleted RGCs.
Figure 5B:
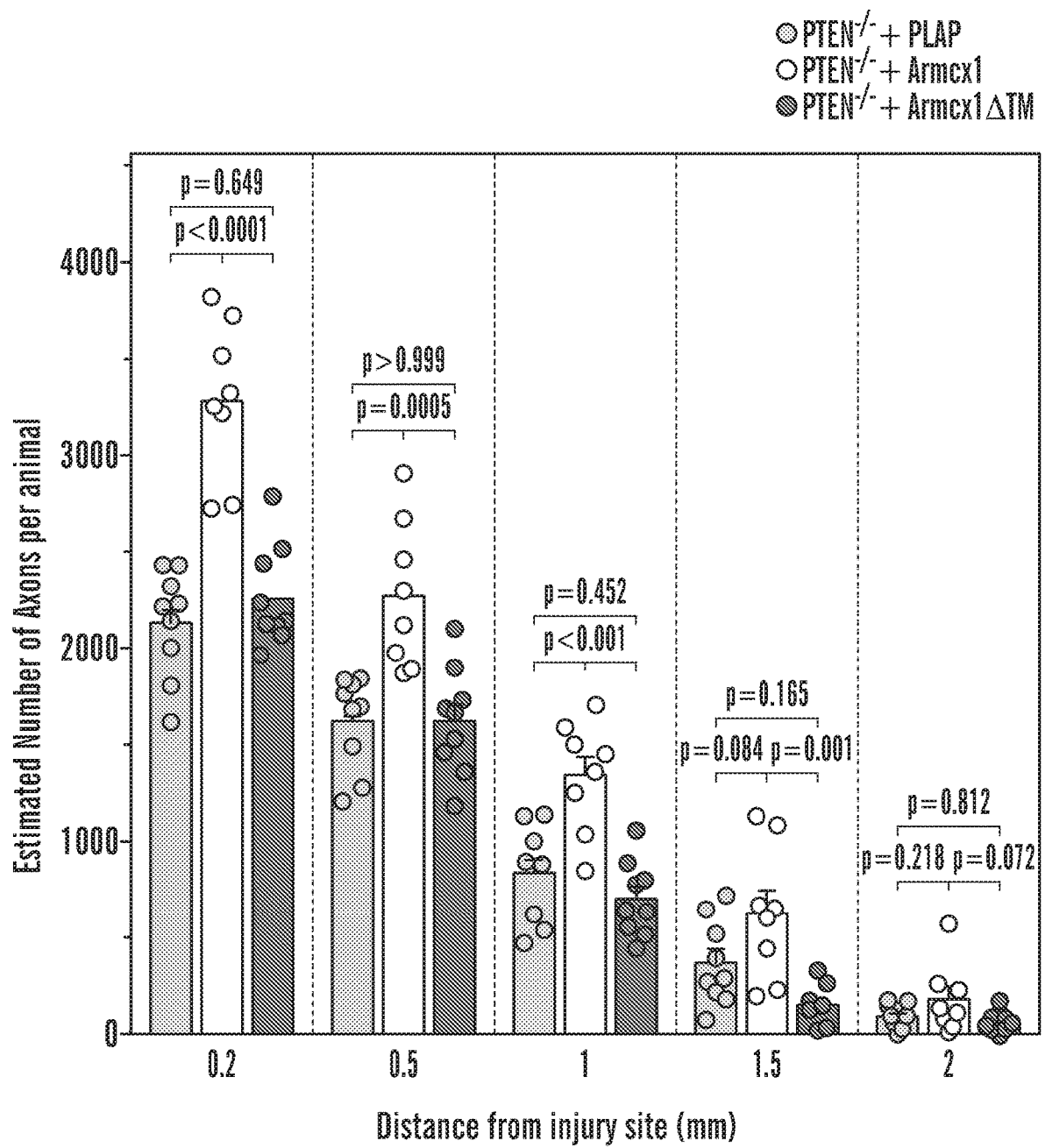
Figure 5D:
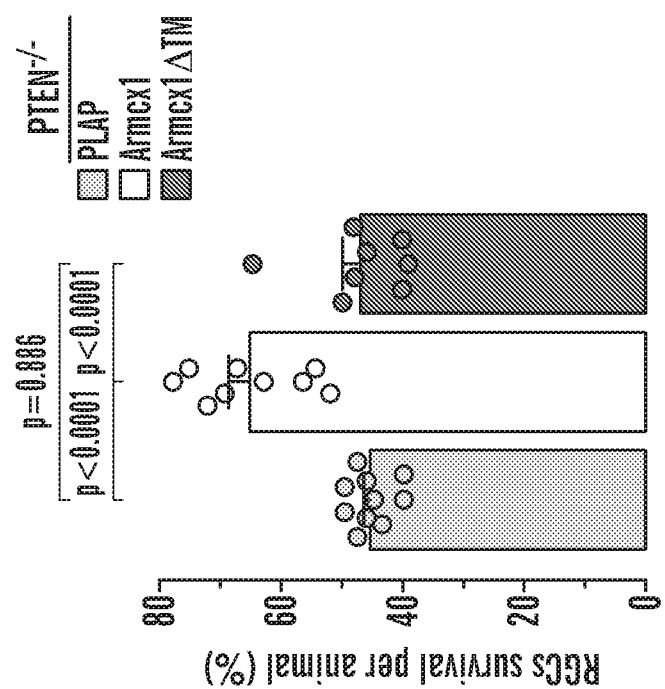
Figure 5C:
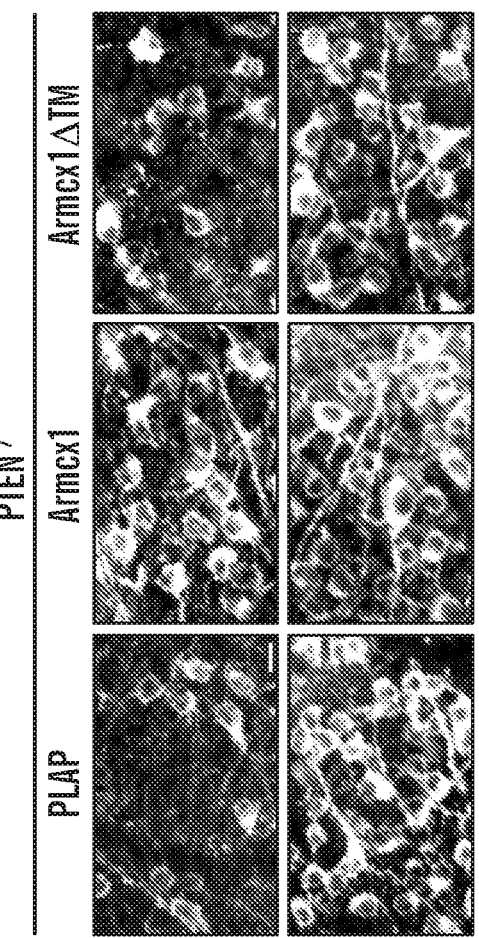
Figure 11A:
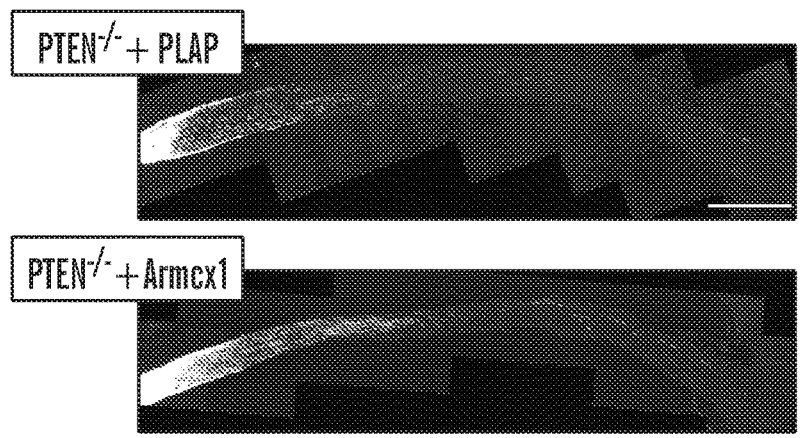
FIGS. 11A-11C shows Armcx1 overexpression in PTEN$^{-/-}$ potentiates regeneration phenotype and partially recapitulates axonal regeneration phenotype of dKO. Related to FIG. 5.
Figure 11B:
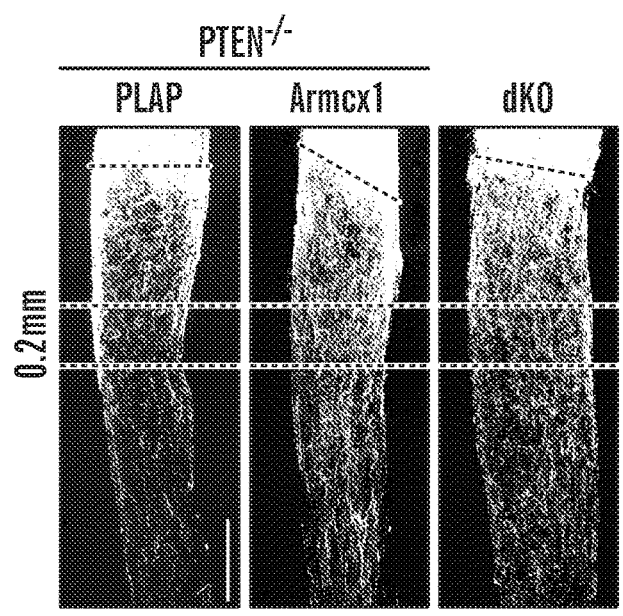
Figure 11C:
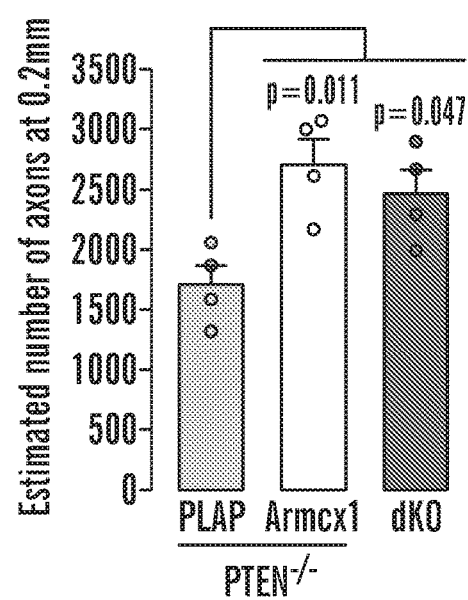

Although Armcx1 has a positive effect on axon regeneration in wild type mice, the limited numbers of regenerating axons might reflect compromised regenerative ability associated with injured RGCs. As our previous studies showed that PTEN deletion in adult RGCs is able to increase neuronal survival and axon regeneration by elevating mTOR activity in injured RGCs (Park et al., 2008), we tested the effect of Armcx1 in this regeneration-permissive background. AAVs expressing Cre together with AAVs expressing Armcx1, Armcx1ΔTM or PLAP as a control, were co-injected to the vitreous body of adult PTENf/f mice and optic nerve crush was performed 4 weeks after viral injection. After an additional 15 days, the regenerating fibers were labeled with the anterograde tracer CTB and examined in optic nerve cross-sections. In this PTEN-deleted background, Armcx1 overexpression induced a significant increase in the number of regenerating axons in comparison with PTEN deletion alone (FIGS. 5A and 5B and 11A). This increase is most striking for the short-regenerating axons, consistent with the results of neurite outgrowth in retinal explants (FIGS. 2E-2G). In a side-by-side study the high regeneration capacity of PTEN deleted RGCs overexpressing Armcx1 fell within the same range as the dKO phenotype (FIGS. 11B and 11C). In addition, Armcx1 overexpression also further increased RGC survival induced by PTEN deletion (FIGS. 5C and 5D). As expected, the mutant Armcx1ΔTM failed to alter either neuronal survival or axon regeneration (FIGS. 5A-5D).

Figure 5F:
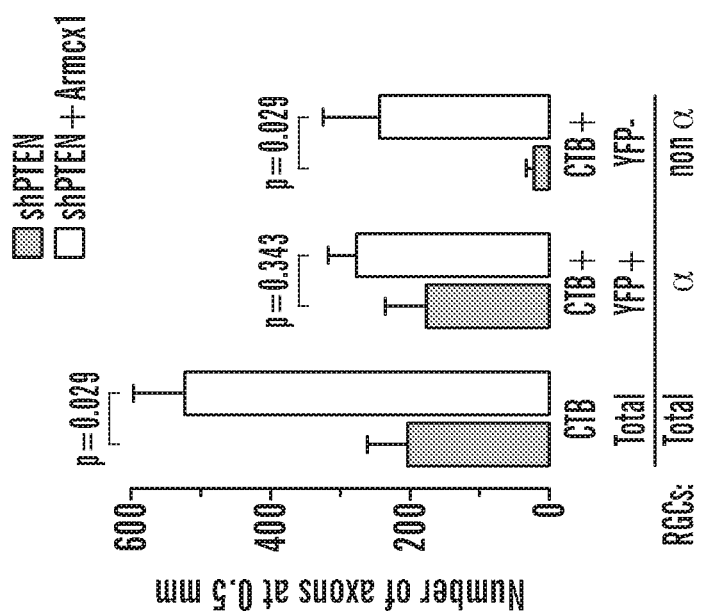
Figure 5E:
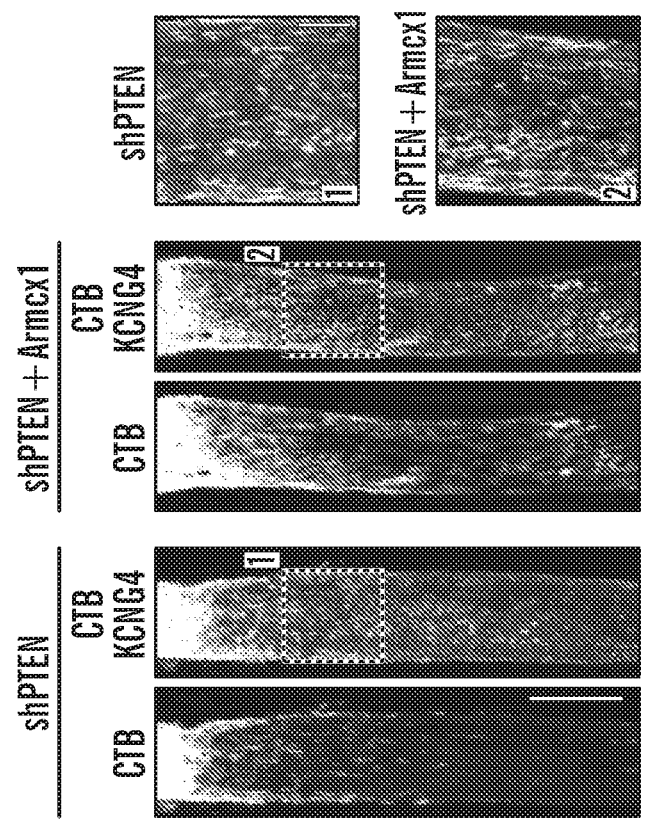

Previous studies demonstrated that among different RGC subtypes analyzed, PTEN inhibition selectively promotes regeneration from αRGCs (Duan et al., 2015). The high number of injured axons growing beyond the injury site when Armcx1 was overexpressed in PTEN deleted mice (FIGS. 5A and 5B) prompted us to test the effects of Armcx1 on promoting the regeneration of different RGC subtypes. To this end, the mouse line Kcng4-Cre; Thy1-stop-YFP line 1 (Kcng4-YFP) that labels αRGCs and their axons (Duan et al., 2015; 2014) was used. To inhibit PTEN expression, AAVs expressing shRNA against PTEN (Duan et al., 2015; Zukor et al., 2013) were injected with or without AAV-Armcx1 to the Kcng4-YFP mice. At 15 days post injury, CTB injection was performed in order to label all regenerating axons from both αRGCs and non-αRGCs. Therefore, YFP+/CTB+ axons should be derived from αRGCs, while the YFP−/CTB+ axons are likely to be from non-αRGCs. As shown in FIGS. 5E and 5F, Armcx1 overexpression induced a significant increase in regenerating axons from non-αRGCs as quantified at 0.5 mm distal from the lesion sites. αRGC-derived regenerating axons also showed a trend of increase, but did not reach statistical significance (FIG. 5F). These results suggest that in contrast to the selective effects of PTEN inhibition on αRGCs, Armcx1 is likely to promote axons regeneration from non-αRGCs and possibly from αRGCs to some extent.

Figure 12A:
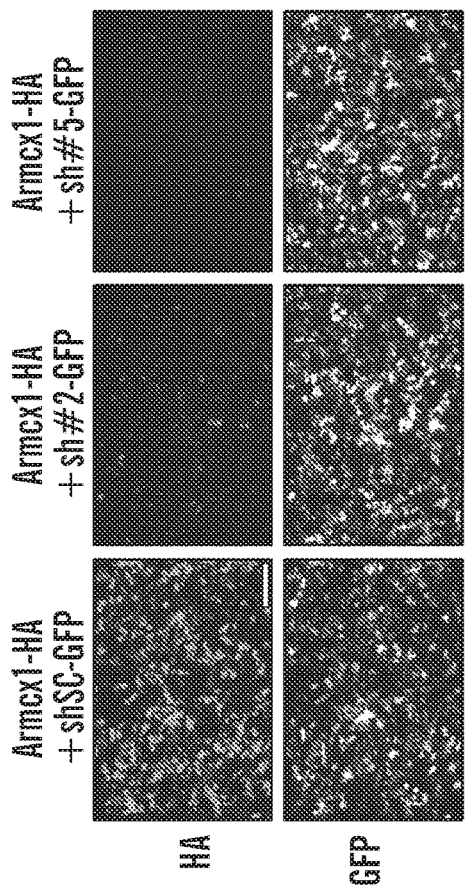
FIGS. 12A-12K Armcx1 is necessary for dKO high regeneration phenotype.
Figure 12B:
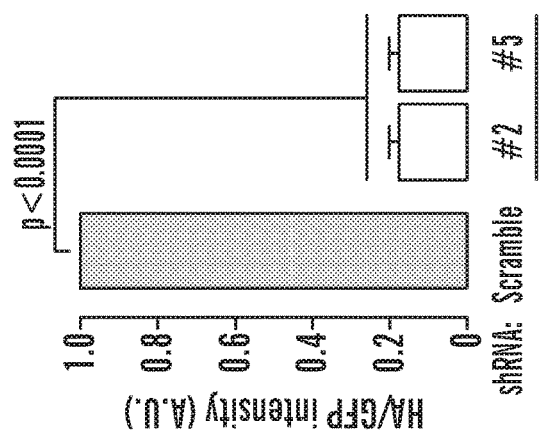
Figure 12C:
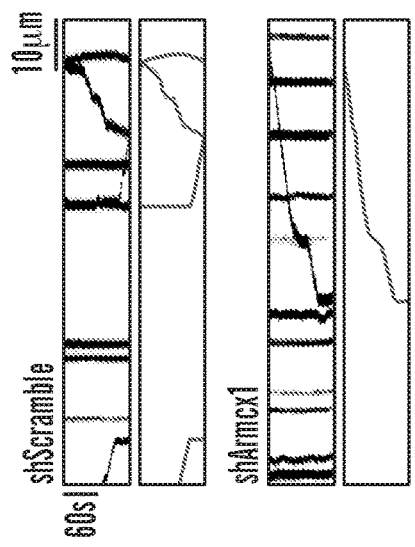
Figure 12D:
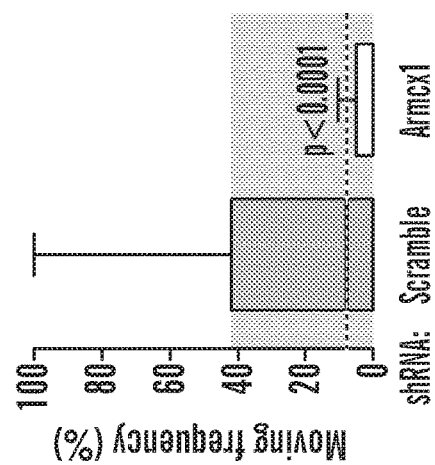
Figure 12F:
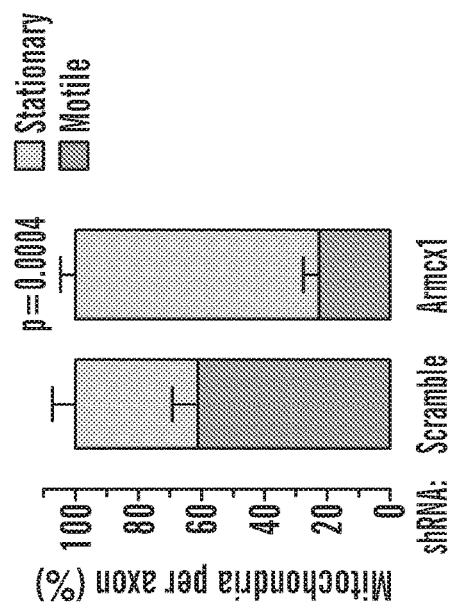
Figure 12E:
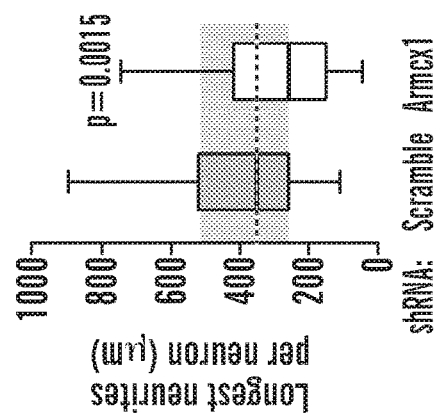
Figure 12G:
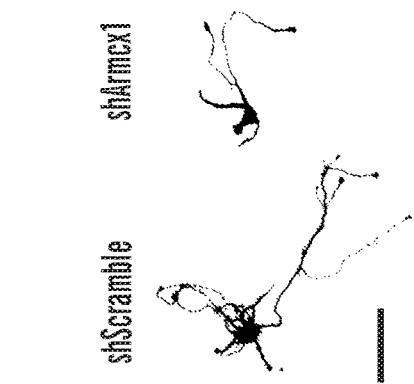
Figure 12H:
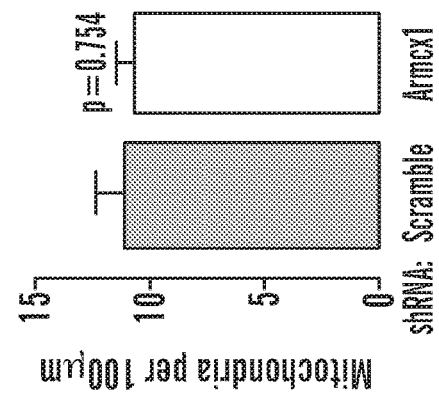

Armcx1 Knockdown Reduces Axon Regeneration and Neuronal Survival in dKO Mice The positive effect of Armcx1 overexpression on axonal regeneration and neuronal survival led us to assess the functional outcomes of silencing Armcx1 expression in both in vitro and in vivo models. We tested five shRNAs targeting different regions of Armcx1 and found two with knockdown efficiency close to 80% (FIGS. 12A and 12B). In order to maximize the knockdown efficiency a vector harboring these two different shRNAs was generated for the subsequent experiments (Song et al., 2008). The effects of Armcx1 knockdown on mitochondrial movement and other functional readouts in cultured E18 cortical neurons was assessed by co-transfecting MitoDsRed with either shRNAs against Armcx1 or shRNA Scramble as a control. To facilitate the identification of transfected neurons these shRNA constructs were designed to carry a fluorescent protein reporter. Knockdown of Armcx1 had a significant effect on mitochondrial transport in axons, decreasing the motile pool from 60% to 20% (FIGS. 12C and 12D). Armcx1 silencing also significantly decreased the moving frequency of mitochondria (FIG. 12E), without affecting mitochondrial density (FIG. 12F). Importantly, knockdown of Armcx1 also significantly reduced neurite growth from transfected neurons (FIGS. 12G and 12H). Thus, these results are consistent with our overexpression data and support a role of Armcx1 in regulating mitochondria movement and neurite growth in cultured cortical neurons.

Figure 6A:
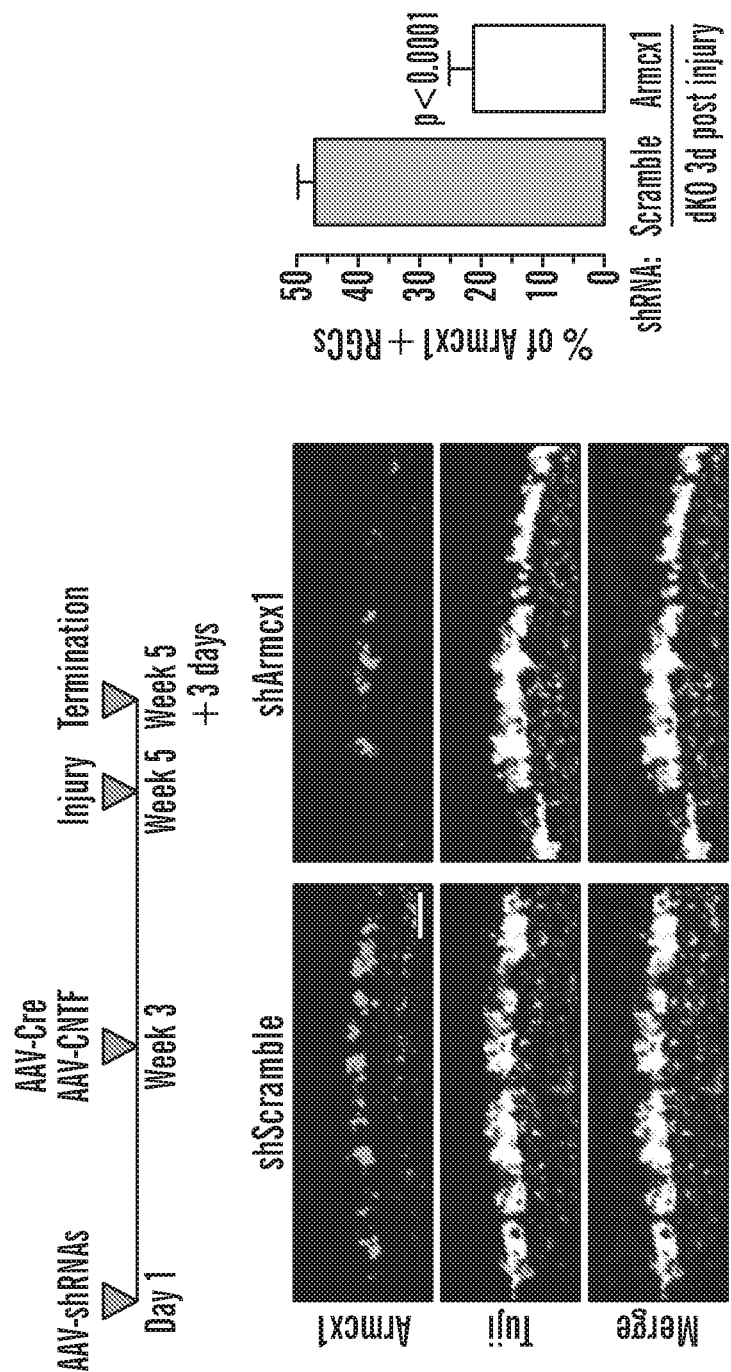
Figure 12J:
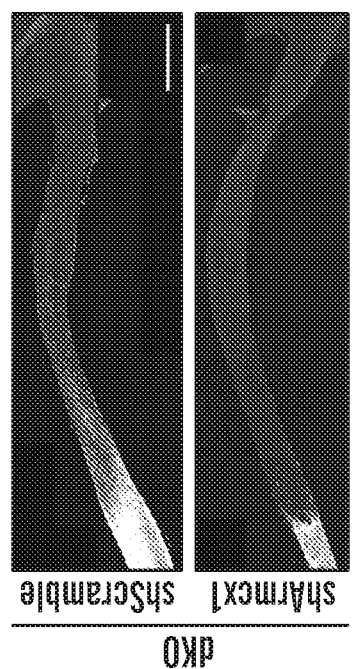
Figure 12I:
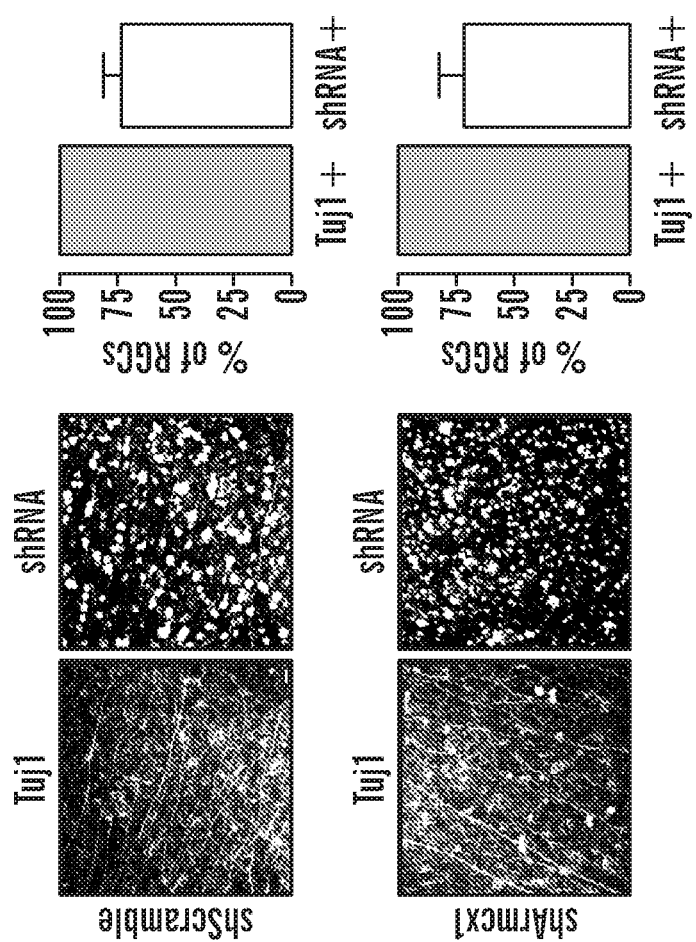

Finally, whether the up-regulation of Armcx1 in RGCs of dKO mice is necessary for their high-regeneration phenotype was tested. To directly test this hypothesis, Armcx1 was knocked down in dKO mice in which Armcx1 is up-regulated (Sun et al., 2012, FIGS. 1A-1C). AAV carrying shRNAs against Armcx1 and the control shRNA Scramble were generated. These two viruses were both able to efficiently infect RGCs (FIG. 12I). To assess the effects of shRNA Armcx1 virus on Armcx1 expression in injured dKO RGCs we injected AAV-Armcx1 shRNAs or Scramble in the retina of dKO mice. 5 weeks post injection of the shRNA AAVs, optic nerve crush was performed the animals terminated 3 days post injury. Approximately 50% of RGCs were Armcx1 positive in dKO retinas with injection of AAV expressing shRNA-Scramble (FIG. 6A), consistent with our immunohistochemistry results from FIGS. 1B and 1C. In contrast, AAV expressing Armcx1-shRNAs significantly reduced this number, bringing the percentage of Armcx1 positive RGCs to a level comparable to wild type condition, i.e. around 20% (FIG. 6A).

Figure 6B:
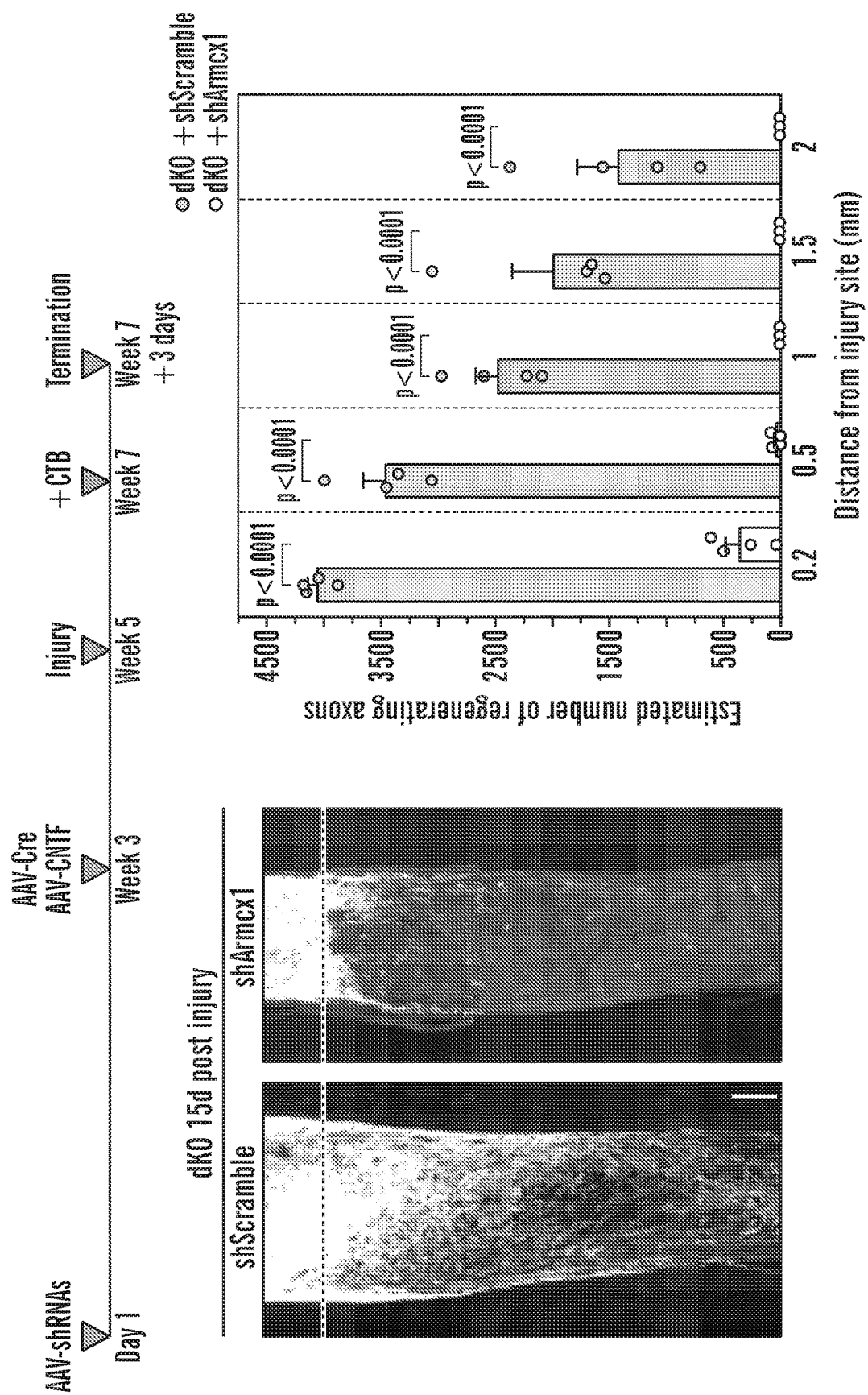
Figure 6C:
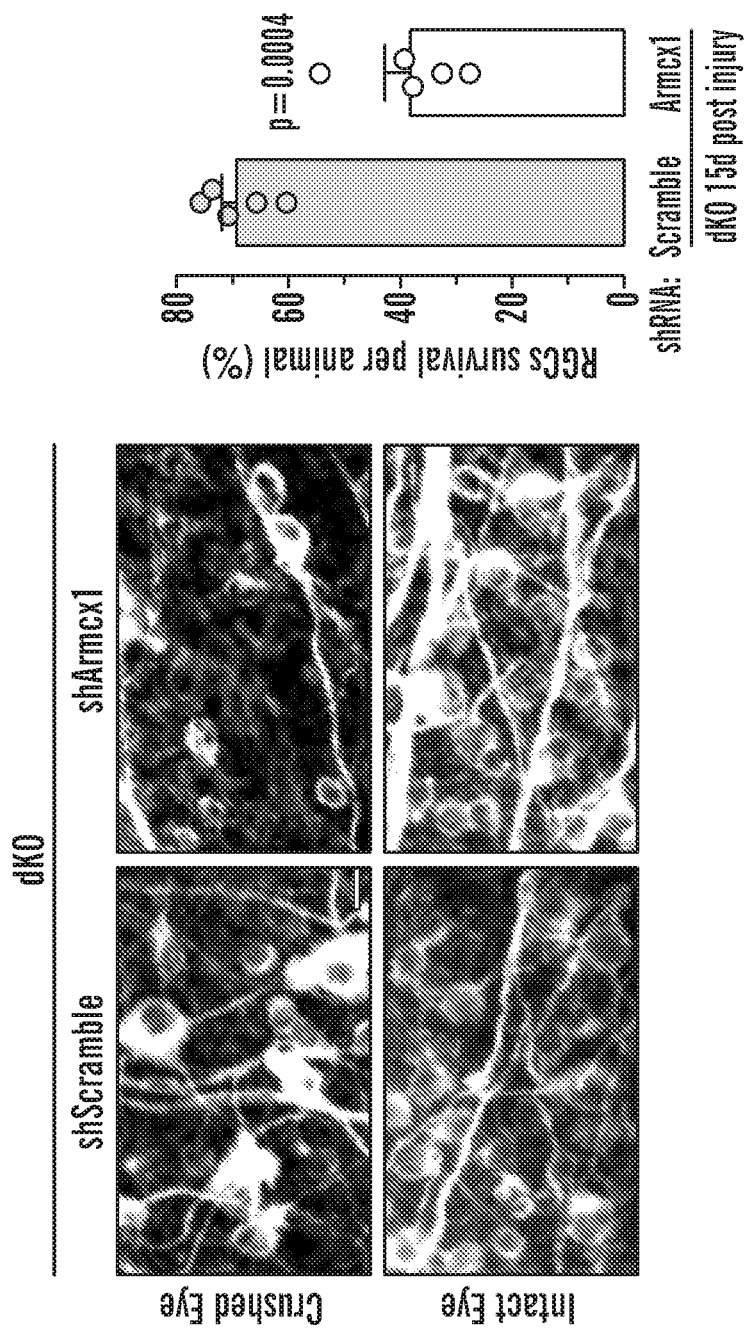
Figure 12K:
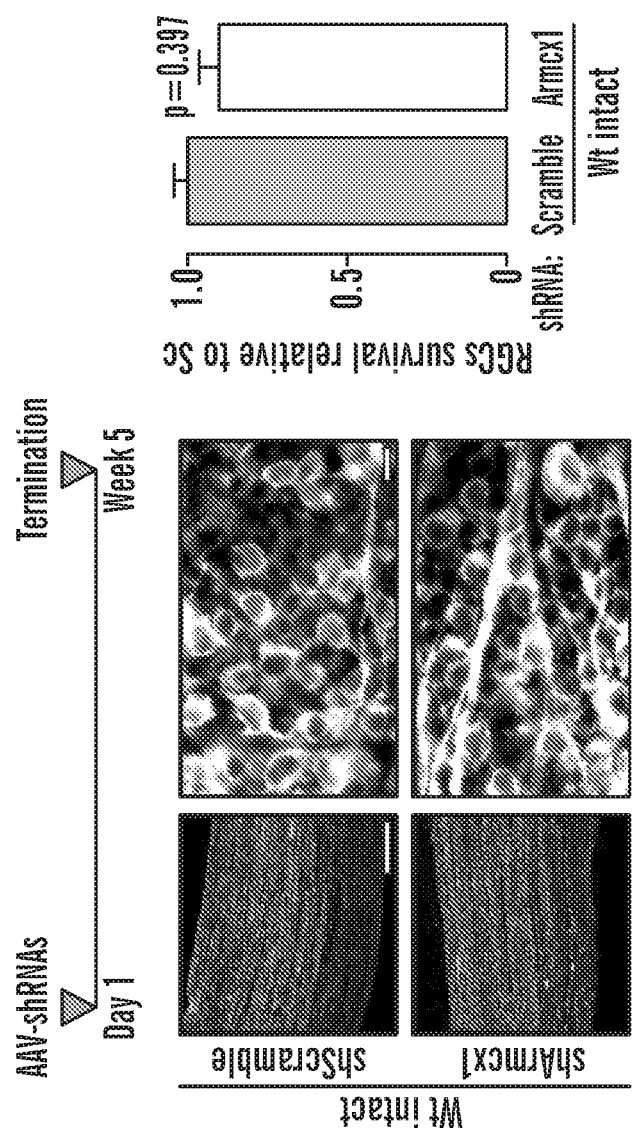

To study the effect of Armcx1 down-regulation on axon regeneration in dKO mice, mice from the same cohort described above were used but terminated 15 days post injury. As shown in FIG. 6B and FIG. 12J, knocking down Armcx1 significantly inhibited the axon regeneration phenotype. Whole mount retina analysis revealed that shRNAs of Armcx1 also significantly reduced RGC survival in dKO mice, compared to the control Scramble shRNA (FIG. 6C). In a separate control, the same AAV vectors were injected to the vitreous bodies of wild type mice and analyzed these mice at 5 weeks post injection. CTB traced optic nerve axons did not show any sign of degeneration comparing to control injected with AAV-shRNA Scramble and RGC survival was not significantly different between conditions (FIG. 12K). Together, these results suggest that injury-induced Armcx1 expression is required for the increased neuronal survival and axon regeneration phenotypes of the dKO model.

Discussion

In this study, the mitochondrial protein Armcx1 is shown sufficient to (1) increase mitochondrial transport by recruiting stationary mitochondria, (2) protect axotomized neurons from cell death, and (3) promote axon regeneration. Armcx1 is further shown necessary for the axon regeneration and neuronal survival phenotypes observed in high regenerative conditions induced by the co-deletion of PTEN and SOCS3 and an accompanying treatment of CNTF (dKO). Together with the fact that Armcx1 expression is injury-induced and correlates with high regenerative ability, our results suggest Armcx1 as a key regulator of mitochondrial transport in injured axons, which could impact neuronal survival and axon regeneration. Modulated mitochondrial transport might constitute a new strategy to promote neuronal repair of the injured CNS.

The precise mechanisms of Armcx1 in injured axons remain to be determined. Similar to Armcx3, Armcx1 is able to interact with the Miro/Trak mitochondrial transport complex. However, it remains to be determined whether Armcx1 mobilizes stationary mitochondria in a calcium dependent manner as has been proposed for Armcx3 (López Doménech et al., 2012). Like other members of the Armcx cluster, Armcx1 has a nuclear localization signal (FIG. 1D and (López-Doménech et al., 2012)). In these studies, some overexpressed Armcx1 was also found to be localized to the nuclei of transfected neurons. Thus, although other functions of Armcx1 cannot be ruled out, the results from the Armcx1ΔTM mutant suggest that the mitochondria-targeted Armcx1 protein is responsible for its function in promoting axon regeneration and RGC survival. In the same line, a recent study showed that enhancing mitochondrial transport by genetic deletion of the gene encoding the mitochondria-anchoring protein syntaphilin also facilitated axon regeneration by rescuing energy deficits in injured axons (Zhou et al., 2016). However, whether Armcx1 acts by regulating energy supply or other mechanisms, such as regulation of calcium homeostasis, signaling via reactive oxygen species, or changes in the production of metabolites, requires further studies. In addition, sustained axon regeneration likely involves the enhanced axonal transport of not only mitochondria but also other axonal building blocks. Thus, it would be interesting to identify other regulators of axonal transport in neurons with increased regenerative ability.

In the PTEN deletion background, Armcx1 overexpression further increased the number of regenerating axons (FIGS. 5A, 5B and 11). Interestingly, this is in contrast with other treatments, such as overexpression of DCLK2, a cytoskeleton regulator, which increases the length of regenerating axons without substantially affecting the number of regenerating axons induced by PTEN deletion (Nawabi et al., 2015). These results, together with our loss of function experiment where Armcx1 down-regulation inhibited dKO-induced axon regeneration (FIGS. 6A-6C), suggest that Armcx1 is more important for the initiation phase of axon regeneration. The increased regeneration observed with Armcx1 overexpression is unlikely to be merely secondary to improved neuronal survival because RGC loss is efficiently prevented by Bcl-2 expression, although Bcl-2 does not increase regeneration. Moreover, in the Bcl-2 expressing background Armcx1 enhances regeneration without an additive effect on RGC survival (FIG. 10). Finally, even though expression of Armcx1 shRNA reduced RGC regeneration in dKO mice back to a level comparable to wild type mice (FIG. 6B and FIG. 4A), RGCs survival was less drastically affected (FIG. 6C and FIG. 4E).

In a PTEN deletion background, Armcx1 overexpression was also shown to facilitate additional axon regeneration from non-αRGCs, a cell type that otherwise exhibits little regeneration. It is possible that different RGC sub-types have different needs in terms of mitochondrial function; non-αRGCs may have a greater dependency on mobilization of mitochondria by Armcx1 in order to cope with injury-induced stresses such as calcium influx and energy imbalance. However, it is unknown whether Armcx1 effects somatic mitochondria the same as axonal mitochondria; these differentially localized mitochondria may be responsible for distinct effects on neuronal survival and axon regeneration. Nevertheless, as visual functions appear to be executed by different classes of RGCs (Sanes and Masland, 2015; Wernet et al., 2014), these results might be insightful for designing more efficient neural repair strategies to target different populations of RGCs.

The Armcx-cluster specificity to Eutherian mammals might imply that it has evolved as an additional layer of mitochondrial transport regulation to match the increasing complexity of the mammalian CNS. Our results suggest that this extra layer of regulation might be especially important when stress, such as an injury, is applied to the axon. Because mitochondrial transport failure has been reported in many neurodegenerative diseases (De Vos et al., 2008), increasing mitochondrial transport has been proposed as an exciting option to counteract axonal degeneration and subsequent neuronal death (Hinckelmann et al., 2013). With this perspective, the present study suggests that Armcx1 and its homologues could be a set of important targets of therapeutic interventions for neuronal protection and repair.

REFERENCES

Abe, N., and Cavalli, V. (2008). Nerve injury signaling. Current Opinion in Neurobiology 18, 276-283.

Bei, F., Lee, H. H. C., Liu, X., Gunner, G., Jin, H., Ma, L., Wang, C., Hou, L., Hensch, T. K., Frank, E., et al. Restoration of Visual Function by Enhancing Conduction in Regenerated Axons. Cell 164, 219-232.

Belin, S., Nawabi, H., Wang, C., Tang, S., Latremoliere, A., Warren, P., Schorle, H., Uncu, C., Woolf, C. J., He, Z., et al. (2015). Injury-Induced Decline of Intrinsic Regenerative Ability Revealed by Quantitative Proteomics. Neuron 86, 1000-1014.

Bonfanti, L., Strettoi, E., Chierzi, S., Cenni, M. C., Liu, X. H., Martinou, J. C., Maffei, L., and Rabacchi, S. A. (1996). Protection of retinal ganglion cells from natural and axotomyinduced cell death in neonatal transgenic mice overexpressing bcl-2. J Neurosci 16, 4186-4194.

Bradke, F., Fawcett, J. W., and Spira, M. E. (2012). Assembly of a new growth cone after axotomy: the precursor to axon regeneration. Nature Reviews Neuroscience 13, 183-193.

Cartoni, R., Léger, B., Hock, M. B., Praz, M., Crettenand, A., Pich, S., Ziltener, J.-L., Luthi, F., Dériaz, O., Zorzano, A., et al. (2005). Mitofusins ½ and ERRalpha expression are increased in human skeletal muscle after physical exercise. The Journal of Physiology 567, 349-358.

Courchet, J., Lewis, T. L., Jr., Lee, S., Courchet, V., Liou, D.-Y., Aizawa, S., and Polleux, F. (2013). Terminal Axon Branching Is Regulated by the LKB1-NUAK1 Kinase Pathway via Presynaptic Mitochondrial Capture. Cell 153, 1510-1525.

Cregg, J. M., DePaul, M. A., Filous, A. R., Lang, B. T., Tran, A., and Silver, J. (2014). Functional regeneration beyond the glial scar. Experimental Neurology 253, 197-207.

De Vos, K. J., Grierson, A. J., Ackerley, S., and Miller, C. C. J. (2008). Role of Axonal Transport in Neurodegenerative Diseases*. Annu. Rev. Neurosci. 31, 151-173.

Duan, X., Krishnaswamy, A., la Huerta, De, I., and Sanes, J. R. (2014). Type II cadherins guide assembly of a direction-selective retinal circuit. Cell 158, 793-807.

Duan, X., Qiao, M., Bei, F., Kim, I.-J., He, Z., and Sanes, J. R. (2015). Subtype-Specific Regeneration of Retinal Ganglion Cells following Axotomy: Effects of Osteopontin and mTOR Signaling. Neuron 85, 1244-1256.

Glater, E. E., Megeath, L. J., Stowers, R. S., and Schwarz, T. L. (2006). Axonal transport of mitochondria requires milton to recruit kinesin heavy chain and is light chain independent. The Journal of Cell Biology 173, 545-557.

Goldberg, J. L., and Barres, B. A. (2000). The relationship between neuronal survival and regeneration. Annu. Rev. Neurosci. 23, 579-612.

Goldberg, J. L., Espinosa, J. S., Xu, Y., Davidson, N., Kovacs, G. T. A., and Barres, B. A. (2002). Retinal ganglion cells do not extend axons by default: promotion by neurotrophic signaling and electrical activity. Neuron 33, 689-702.

Hammarlund, M., and Jin, Y. (2014). Axon regeneration in C. elegans. Current Opinion in Neurobiology 27, 199-207.

He, Z., and Jin, Y. (2016). Intrinsic control of axon regeneration. Neuron 90, 437-451.

Hinckelmann, M.-V., Zala, D., and Saudou, F. (2013). Releasing the brake: restoring fast axonal transport in neurodegenerative disorders. Trends in Cell Biology.

Hu, Y., Park, K. K., Yang, L., Wei, X., Yang, Q., Cho, K.-S., Thielen, P., Lee, A.-H., Cartoni, R., Glimcher, L. H., et al. (2012). Differential effects of unfolded protein response pathways on axon injury-induced death of retinal ganglion cells. Neuron 73, 445-452.

López-Doménech, G., Serrat, R., Mirra, S., D'Aniello, S., Somorjai, I., Abad, A., Vitureira, N., Garcia-Arumi, E., Alonso, M. T., Rodriguez-Prados, M., et al. (2012). The Eutherian Armcx genes regulate mitochondrial trafficking in neurons and interact with Miro and Trak2. Nature Communications 3, 814.

Lu, Y., Belin, S., and He, Z. (2014). Signaling regulations of neuronal regenerative ability. Current Opinion in Neurobiology 27, 135-142.

Mar, F. M., Simões, A. R., Leite, S., Morgado, M. M., Santos, T. E., Rodrigo, I. S., Teixeira, C. A., Misgeld, T., and Sousa, M. M. (2014). CNS Axons Globally Increase Axonal Transport after Peripheral Conditioning. Journal of Neuroscience 34, 5965-5970.

Martinou, J.-C., Dubois-Dauphin, M., Staple, J. K., Rodriguez, I., Frankowski, H., Missotten, M., Albertini, P., Talabot, D., Catsicas, S., and Pietra, C. (1994). Overexpression of BCL-2 in transgenic mice protects neurons from naturally occurring cell death and experimental ischemia. Neuron 13, 1017-1030.

Misgeld, T., Kerschensteiner, M., Bareyre, F. M., Burgess, R. W., and Lichtman, J. W. (2007). Imaging axonal transport of mitochondria in vivo. Nature Publishing Group 4, 559-561.

Morris, R. L., and Hollenbeck, P. J. (1993). The regulation of bidirectional mitochondrial transport is coordinated with axonal outgrowth. J Cell Sci 104 (Pt 3), 917-927.

Mou, Z., Tapper, A. R., and Gardner, P. D. (2009). The armadillo repeat-containing protein, ARMCX3, physically and functionally interacts with the developmental regulatory factor Sox10. Journal of Biological Chemistry 284, 13629-13640.

Nawabi, H., Briancon-Marjollet, A., Clark, C., Sanyas, I., Takamatsu, H., Okuno, T., Kumanogoh, A., Bozon, M., Takeshima, K., Yoshida, Y., et al. (2010). A midline switch of receptor processing regulates commissural axon guidance in vertebrates. Genes & Development 24, 396-410.

Nawabi, H., Belin, S., Cartoni, R., Williams, P. R., Wang, C., Latremoliere, A., Wang, X., Zhu, J., Taub, D. G., Fu, X., et al. (2015). Doublecortin-Like Kinases Promote Neuronal Survival and Induce Growth Cone Reformation via Distinct Mechanisms. Neuron.

Park, K. K., Liu, K., Hu, Y., Smith, P. D., Wang, C., Cai, B., Xu, B., Connolly, L., Kramvis, I., Sahin, M., et al. (2008). Promoting axon regeneration in the adult CNS by modulation of the PTEN/mTOR pathway. Science 322, 963-966.

Pekkurnaz, G., Trinidad, J. C., Wang, X., Kong, D., and Schwarz, T. L. (2014). Glucose Regulates Mitochondrial Motility via Milton Modification by O-GlcNAc Transferase. Cell 158, 54-68.

Pernet, V., Joly, S., Jordi, N., Dalkara, D., Guzik-Kornacka, A., Flannery, J. G., and Schwab, M. E. (2013). Misguidance and modulation of axonal regeneration by Stat3 and Rho/ROCK signaling in the transparent optic nerve. Cell Death Dis 4, e734-.

Sanes, J. R., and Masland, R. H. (2015). The types of retinal ganglion cells: current status and implications for neuronal classification. Annu. Rev. Neurosci.

Schwarz, T. L. (2013). Mitochondrial trafficking in neurons. Cold Spring Harb Perspect Biol 5.

Smith, P., Sun, F., Park, K. K., Cai, B., Wang, C., Kuwako, K., Martinez-Carrasco, I., Connolly, L., and He, Z. (2009). SOCS3 deletion promotes optic nerve regeneration in vivo. Neuron 64, 617-623.

Song, J., Giang, A., Lu, Y., Pang, S., and Chiu, R. (2008). Multiple shRNA expressing vector enhances efficiency of gene silencing. BMB Rep 41, 358-362.

Sun, F., Park, K. K., Belin, S., Wang, D., Lu, T., Chen, G., Zhang, K., Yeung, C., Feng, G., Yankner, B. A., et al. (2012). Sustained axon regeneration induced by co-deletion of PTEN and SOCS3. Nature 480, 372-375.

Trushina, E., Nemutlu, E., Zhang, S., Christensen, T., Camp, J., Mesa, J., Siddiqui, A., Tamura, Y., Sesaki, H., Wengenack, T. M., et al. (2012). Defects in mitochondrial dynamics and metabolomic signatures of evolving energetic stress in mouse models of familial Alzheimer's disease. PLoS ONE 7, e32737.

Verburg, J., and Hollenbeck, P. J. (2008). Mitochondrial Membrane Potential in Axons Increases with Local Nerve Growth Factor or Semaphorin Signaling. Journal of Neuroscience 28, 8306-8315.

Wang, X., and Schwarz, T. L. (2009). The Mechanism of Ca. Cell 136, 163-174.

Wang, X., Winter, D., Ashrafi, G., Schlehe, J., Wong, Y. L., Selkoe, D., Rice, S., Steen, J., LaVoie, M. J., and Schwarz, T. L. (2011). PINK1 and Parkin Target Mirofor Phosphorylation and Degradation to Arrest Mitochondrial Motility. Cell 147, 893-906.

Wernet, M. F., Huberman, A. D., and Desplan, C. (2014). So many pieces, one puzzle: cell type specification and visual circuitry in flies and mice. Genes & Amp; Development 28, 2565-2584.

Zhang, L., Trushin, S., Christensen, T. A., Bachmeier, B. V., Gateno, B., Schroeder, A., Yao, J., Itoh, K., Sesaki, H., Poon, W. W., et al. (2016). Altered brain energetics induces mitochondrial fission arrest in Alzheimer's Disease. Sci. Rep. 6, 18725.

Zhou, B., Yu, P., Lin, M.-Y., Sun, T., Chen, Y., and Sheng, Z.-H. (2016). Facilitation of axon regeneration by enhancing mitochondrial transport and rescuing energy deficits. J Cell Biol 104, jcb.201605101.

Zukor, K., Belin, S., Wang, C., Keelan, N., Wang, X., and He, Z. (2013). Short hairpin RNA against PTEN enhances regenerative growth of corticospinal tract axons after spinal cord injury.—PubMed—NCBI. J Neurosci 33, 15350-15361.

---

The invention claimed is:

1. A method for promoting survival of, or axon regeneration in an injured mature central nervous system (CNS) neuron comprising contacting the neuron with an effective amount of an agent capable of increasing mitochondrial motility in the injured neuron, wherein the agent is:
   a) an Armadillo repeat-containing X-linked protein 1 (Armcx1) polypeptide comprising the sequence of SEQ ID NO: 1; or
   b) a vector comprising a nucleic acid sequence encoding the Armcx1 polypeptide; thereby promoting survival of, or axon regeneration in the injured neuron.

2. The method of claim 1, wherein the injured neuron results from traumatic injury, traumatic brain injury, optic nerve injury, acute spinal cord injury, stroke, restorative CNS surgery or CNS degeneration.

3. The method of claim 1, wherein the injured neuron is a sensory neuron.

4. The method of claim 1, wherein the injured neuron is in the spinal cord.

5. The method of claim 1, wherein the injured neuron is in the optic nerve.

6. The method of claim 1, wherein the agent is administered intravenously, intracortically, intracerebrally, intrathecally, intranasally, ocularly or locally at the injured neuron.

7. The method of claim 1, wherein the agent is the Armcx1 polypeptide.

8. The method of claim 7, wherein the Armcx1 polypeptide is recombinant.

9. The method of claim 7, wherein the Armxc1 polypeptide comprises a carrier peptide or lipophilic molecular group and/or is encapsulated in a liposome or a nanoparticle.

10. The method of claim 1, wherein the agent is the vector comprising a nucleic acid sequence that encodes the Armcx1 polypeptide.

11. The method of claim 10, wherein the vector is a viral vector or non-viral vector.

12. The method of claim 11, wherein the viral vector is selected from the group consisting of retrovirus, lentivirus, adenovirus, herpesvirus, poxvirus, alpha virus, vaccinia virus, and adeno-associated viruses.

13. The method of claim 11, wherein the non-viral vector is selected from the group consisting of a nanoparticle, a cationic lipid, a cationic polymer, a metallic nanoparticle, a nanorod, a liposome, microbubbles, a cell penetrating peptide and a liposphere.

14. The method of claim 1, further comprising contacting the injured neuron with a PTEN inhibitor, inhibitor of suppressor of cytokine signaling 3 (SOCS3), inosine, oncomodulin, BNDF, NGF, CNTF, or combinations thereof.

15. A method of treating a subject for neuronal injury, comprising: administering to the subject an agent that increases mitochondrial motility in injured neurons, wherein the agent is:
   a) an Armcx1 polypeptide comprising the sequence of SEQ ID NO: 1; or
   b) a vector comprising a nucleic acid sequence encoding the Armcx1 polypeptide;
wherein the administering results in contacting the injured neurons of the subject with the agent in an amount sufficient to promote survival of, or axon regeneration in the injured neurons, such that the subject is treated.

* * * * *

SEQUENCE LISTING

```
<160> NUMBER OF SEQ ID NOS: 3

<210> SEQ ID NO 1
<211> LENGTH: 453
<212> TYPE: PRT
<213> ORGANISM: Homo sapiens

<400> SEQUENCE: 1

Met Gly Arg Thr Arg Glu Ala Gly Cys Val Ala Ala Gly Val Val Ile
1               5                   10                  15

Gly Ala Gly Ala Cys Tyr Cys Val Tyr Arg Leu Ala Trp Gly Arg Asp
            20                  25                  30

Glu Asn Glu Lys Ile Trp Asp Glu Asp Glu Ser Thr Asp Thr Ser
        35                  40                  45

Glu Ile Gly Val Glu Thr Val Lys Gly Ala Lys Thr Asn Ala Gly Ala
    50                  55                  60

Gly Ser Gly Ala Lys Leu Gln Gly Asp Ser Glu Val Lys Pro Glu Val
65                  70                  75                  80

Ser Leu Gly Leu Glu Asp Cys Pro Gly Val Lys Glu Lys Ala His Ser
                85                  90                  95

Gly Ser His Ser Gly Gly Leu Glu Ala Lys Ala Lys Ala Leu Phe
            100                 105                 110

Asn Thr Leu Lys Glu Gln Ala Ser Ala Lys Ala Gly Lys Gly Ala Arg
        115                 120                 125

Val Gly Thr Ile Ser Gly Asn Arg Thr Leu Ala Pro Ser Leu Pro Cys
    130                 135                 140
```

Pro Gly Gly Arg Gly Gly Cys His Pro Thr Arg Ser Gly Ser Arg
145                 150                 155                 160

Ala Gly Gly Arg Ala Ser Gly Lys Ser Lys Gly Lys Ala Arg Ser Lys
                165                 170                 175

Ser Thr Arg Ala Pro Ala Thr Thr Trp Pro Val Arg Arg Gly Lys Phe
            180                 185                 190

Asn Phe Pro Tyr Lys Ile Asp Asp Ile Leu Ser Ala Pro Asp Leu Gln
        195                 200                 205

Lys Val Leu Asn Ile Leu Glu Arg Thr Asn Asp Pro Phe Ile Gln Glu
    210                 215                 220

Val Ala Leu Val Thr Leu Gly Asn Asn Ala Ala Tyr Ser Phe Asn Gln
225                 230                 235                 240

Asn Ala Ile Arg Glu Leu Gly Gly Val Pro Ile Ile Ala Lys Leu Ile
                245                 250                 255

Lys Thr Lys Asp Pro Ile Ile Arg Glu Lys Thr Tyr Asn Ala Leu Asn
            260                 265                 270

Asn Leu Ser Val Asn Ala Glu Asn Gln Gly Lys Ile Lys Thr Tyr Ile
        275                 280                 285

Ser Gln Val Cys Asp Asp Thr Met Val Cys Arg Leu Asp Ser Ala Val
    290                 295                 300

Gln Met Ala Gly Leu Arg Leu Leu Thr Asn Met Thr Val Thr Asn His
305                 310                 315                 320

Tyr Gln His Leu Leu Ser Tyr Ser Phe Pro Asp Phe Ala Leu Leu
                325                 330                 335

Phe Leu Gly Asn His Phe Thr Lys Ile Gln Ile Met Lys Leu Ile Ile
            340                 345                 350

Asn Phe Thr Glu Asn Pro Ala Met Thr Arg Glu Leu Val Ser Cys Lys
        355                 360                 365

Val Pro Ser Glu Leu Ile Ser Leu Phe Asn Lys Glu Trp Asp Arg Glu
    370                 375                 380

Ile Leu Leu Asn Ile Leu Thr Leu Phe Glu Asn Ile Asn Asp Asn Ile
385                 390                 395                 400

Lys Asn Glu Gly Leu Ala Ser Ser Arg Lys Glu Phe Ser Arg Ser Ser
                405                 410                 415

Leu Phe Phe Leu Phe Lys Glu Ser Gly Val Cys Val Lys Lys Ile Lys
            420                 425                 430

Ala Leu Ala Asn His Asn Asp Leu Val Val Val Lys Val Leu Lys
        435                 440                 445

Val Leu Thr Lys Leu
    450

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gagaggcaaa cctcaagatg actc                                          24

<210> SEQ ID NO 3
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 3
tcagtcaagt gtgtgacgat acc                                               23
```